US008492359B2

(12) United States Patent  (10) Patent No.: US 8,492,359 B2
Yaworski et al.  (45) Date of Patent: *Jul. 23, 2013

(54) LIPID FORMULATIONS FOR NUCLEIC ACID DELIVERY

(75) Inventors: Edward Yaworski, Maple Ridge (CA); Kieu Lam, Surrey (CA); Lloyd Jeffs, Delta (CA); Lorne Palmer, Vancouver (CA); Ian MacLachlan, Mission (CA)

(73) Assignee: Protiva Biotherapeutics, Inc., Burnaby, BC (CA)

( * ) Notice: Subject to any disclaimer, the term of this patent is extended or adjusted under 35 U.S.C. 154(b) by 59 days.

This patent is subject to a terminal disclaimer.

(21) Appl. No.: 13/253,917

(22) Filed: Oct. 5, 2011

(65) Prior Publication Data

US 2012/0183581 A1   Jul. 19, 2012

Related U.S. Application Data

(63) Continuation of application No. 12/424,367, filed on Apr. 15, 2009, now Pat. No. 8,058,069.

(60) Provisional application No. 61/045,228, filed on Apr. 15, 2008.

(51) Int. Cl.
    *C12N 15/11*  (2006.01)

(52) U.S. Cl.
    USPC ..................................................... 514/44 A

(58) Field of Classification Search
    USPC ..................................................... 514/44 A
    See application file for complete search history.

(56) References Cited

U.S. PATENT DOCUMENTS

| | | | |
|---|---|---|---|
| 4,394,448 A | 7/1983 | Szoka, Jr. et al. |
| 4,438,052 A | 3/1984 | Weder et al. |
| 4,515,736 A | 5/1985 | Deamer |
| 4,598,051 A | 7/1986 | Papahadjopoulos et al. |
| 4,897,355 A | 1/1990 | Eppstein et al. |
| 5,013,556 A | 5/1991 | Woodle et al. |
| 5,171,678 A | 12/1992 | Behr et al. |
| 5,208,036 A | 5/1993 | Eppstein et al. |
| 5,225,212 A | 7/1993 | Martin et al. |
| 5,264,618 A | 11/1993 | Felgner et al. |
| 5,279,833 A | 1/1994 | Rose |
| 5,283,185 A | 2/1994 | Epand et al. |
| 5,320,906 A | 6/1994 | Eley et al. |
| 5,334,761 A | 8/1994 | Gebeyehu et al. |
| 5,545,412 A | 8/1996 | Eppstein et al. |
| 5,578,475 A | 11/1996 | Jessee |
| 5,627,159 A | 5/1997 | Shih et al. |
| 5,641,662 A | 6/1997 | Debs et al. |
| 5,656,743 A | 8/1997 | Busch et al. |
| 5,674,908 A | 10/1997 | Haces et al. |
| 5,703,055 A | 12/1997 | Felgner et al. |
| 5,705,385 A | 1/1998 | Bally et al. |
| 5,736,392 A | 4/1998 | Hawley-Nelson et al. |
| 5,820,873 A | 10/1998 | Choi et al. |
| 5,877,220 A | 3/1999 | Schwartz et al. |
| 5,885,613 A | 3/1999 | Holland et al. |
| 5,958,901 A | 9/1999 | Dwyer et al. |
| 5,976,567 A | 11/1999 | Wheeler et al. |
| 5,981,501 A | 11/1999 | Wheeler et al. |
| 6,020,202 A | 2/2000 | Jessee |
| 6,020,526 A | 2/2000 | Schwartz et al. |
| 6,034,135 A | 3/2000 | Schwartz et al. |
| 6,051,429 A | 4/2000 | Hawley-Nelson et al. |
| 6,075,012 A | 6/2000 | Gebeyehu et al. |
| 6,165,501 A | 12/2000 | Tirosh et al. |
| 6,172,049 B1 | 1/2001 | Dwyer et al. |
| 6,251,939 B1 | 6/2001 | Schwartz et al. |
| 6,284,267 B1 | 9/2001 | Aneja |
| 6,287,591 B1 | 9/2001 | Semple et al. |
| 6,339,173 B1 | 1/2002 | Schwartz et al. |
| 6,376,248 B1 | 4/2002 | Hawley-Nelson et al. |
| 6,534,484 B1 | 3/2003 | Wheeler et al. |
| 6,586,410 B1 | 7/2003 | Wheeler et al. |
| 6,638,529 B2 | 10/2003 | Schwartz et al. |
| 6,649,780 B1 | 11/2003 | Eibl et al. |
| 6,671,393 B2 | 12/2003 | Hays et al. |
| 6,696,424 B1 | 2/2004 | Wheeler |
| 6,815,432 B2 | 11/2004 | Wheeler et al. |
| 6,858,224 B2 | 2/2005 | Wheeler et al. |

(Continued)

FOREIGN PATENT DOCUMENTS

| CA | 2309727 A1 | 4/1999 |
|---|---|---|
| CA | 2271582 A1 | 11/1999 |

(Continued)

OTHER PUBLICATIONS

Arpicco, S., et al., "Preparation and Characterization of Novel Cationic Lipids Developed for Gene Transfection," Proceed. Int'l Symp. Control. Rel. Bioact. Mater. (Controlled Release Society, Inc.), 1999, vol. 26, pp. 759-760.

Arpicco, S., et al., "Synthesis, characterization and transfection activity of new saturated and unsaturated cationic lipids," IL Farmaco, 2004, vol. 59, pp. 869-878.

Ballas, N., et al., "Liposomes bearing a quaternary ammonium detergent as an efficient vehicle for functional transfer of TMV-RNA into plant protoplasts," Biochimica et Biophysica Acta, 1988, vol. 939, pp. 8-18.

Barinaga, M., "Step Taken Toward Improved Vectors for Gene Transfer," Science, 1994, vol. 266, p. 1326.

Bass, "The Short Answer," *Nature*, 2001, 411: 428-9.

Beale, G., et al., "Gene Silencing Nucleic Acids Designed by Scanning Arrays: Anti-EGFR Activity of siRNA, Ribozyme and DNA Enzymes Targeting a Single Hybridization-accessible Region using the Same Delivery System," Journal of Drug Targeting, 2003, vol. 11, No. 7, pp. 449-456.

(Continued)

*Primary Examiner* — Brian Whiteman
(74) *Attorney, Agent, or Firm* — Kilpatrick Townsend & Stockton LLP

(57) ABSTRACT

The present invention provides novel, stable lipid particles comprising one or more active agents or therapeutic agents, methods of making the lipid particles, and methods of delivering and/or administering the lipid particles. More particularly, the present invention provides stable nucleic acid-lipid particles (SNALP) comprising a nucleic acid (such as one or more interfering RNA), methods of making the SNALP, and methods of delivering and/or administering the SNALP.

21 Claims, 24 Drawing Sheets

U.S. PATENT DOCUMENTS

| | | | |
|---|---|---|---|
| 7,166,745 B1 | 1/2007 | Chu et al. | |
| 7,422,902 B1 | 9/2008 | Wheeler et al. | |
| 7,479,573 B2 | 1/2009 | Chu et al. | |
| 7,601,872 B2 | 10/2009 | Chu et al. | |
| 7,687,070 B2 | 3/2010 | Gebeyehu et al. | |
| 7,745,651 B2 | 6/2010 | Heyes et al. | |
| 7,799,565 B2 | 9/2010 | MacLachlan et al. | |
| 7,803,397 B2 | 9/2010 | Heyes et al. | |
| 7,807,815 B2 | 10/2010 | MacLachlan et al. | |
| 7,838,658 B2 | 11/2010 | MacLachlan et al. | |
| 7,901,708 B2 | 3/2011 | MacLachlan et al. | |
| 7,915,450 B2 | 3/2011 | Chu et al. | |
| 7,982,027 B2 | 7/2011 | MacLachlan et al. | |
| 8,058,068 B2 | 11/2011 | Hawley-Nelson et al. | |
| 8,058,069 B2 * | 11/2011 | Yaworski et al. | 435/458 |
| 8,158,827 B2 | 4/2012 | Chu et al. | |
| 8,227,443 B2 | 7/2012 | MacLachlan et al. | |
| 2001/0048940 A1 | 12/2001 | Tousignant et al. | |
| 2003/0069173 A1 | 4/2003 | Hawley-Nelson et al. | |
| 2003/0077829 A1 | 4/2003 | MacLachlan | |
| 2003/0143732 A1 | 7/2003 | Fosnaugh et al. | |
| 2004/0063654 A1 | 4/2004 | Davis et al. | |
| 2004/0142892 A1 | 7/2004 | Finn et al. | |
| 2004/0253723 A1 | 12/2004 | Tachas et al. | |
| 2004/0259247 A1 | 12/2004 | Tuschl et al. | |
| 2005/0064595 A1 | 3/2005 | MacLachlan et al. | |
| 2005/0118253 A1 | 6/2005 | MacLachlan et al. | |
| 2005/0260757 A1 | 11/2005 | Gebeyehu et al. | |
| 2006/0008910 A1 | 1/2006 | MacLachlan et al. | |
| 2006/0147514 A1 | 7/2006 | Gebeyehu et al. | |
| 2006/0228406 A1 | 10/2006 | Chiou et al. | |
| 2007/0042031 A1 | 2/2007 | MacLachlan et al. | |
| 2007/0202598 A1 | 8/2007 | Chu et al. | |
| 2007/0202600 A1 | 8/2007 | Chu et al. | |
| 2009/0143583 A1 | 6/2009 | Chu et al. | |
| 2009/0291131 A1 | 11/2009 | MacLachlan et al. | |
| 2010/0159593 A1 | 6/2010 | Chu et al. | |
| 2012/0136073 A1 | 5/2012 | Yang et al. | |
| 2012/0238747 A1 | 9/2012 | Chu et al. | |

FOREIGN PATENT DOCUMENTS

| | | |
|---|---|---|
| CA | 2330741 A1 | 11/1999 |
| CA | 2397016 A1 | 7/2001 |
| JP | 03-126211 | 5/1991 |
| JP | 05-202085 | 8/1993 |
| JP | 06-080560 | 3/1994 |
| WO | WO 91/16024 A1 | 10/1991 |
| WO | WO 93/05162 A1 | 3/1993 |
| WO | WO 93/12240 A1 | 6/1993 |
| WO | WO 93/12756 A2 | 7/1993 |
| WO | WO 93/24640 A2 | 12/1993 |
| WO | WO 93/25673 A1 | 12/1993 |
| WO | WO 95/02698 A1 | 1/1995 |
| WO | WO 95/18863 A1 | 7/1995 |
| WO | WO 95/35301 A1 | 12/1995 |
| WO | WO 96/02655 A1 | 2/1996 |
| WO | WO 96/10390 A1 | 4/1996 |
| WO | WO 96/41873 A1 | 12/1996 |
| WO | WO 98/51285 A2 | 11/1998 |
| WO | WO 00/03683 A2 | 1/2000 |
| WO | WO 00/15820 A1 | 3/2000 |
| WO | WO 00/62813 A2 | 10/2000 |
| WO | WO 01/05374 A1 | 1/2001 |
| WO | WO 01/05873 A1 | 1/2001 |
| WO | WO 02/34236 A2 | 5/2002 |
| WO | WO 02/087541 A1 | 11/2002 |
| WO | WO 03/097805 A2 | 11/2003 |
| WO | WO 2004/065546 A2 | 8/2004 |
| WO | WO 2004/110499 A1 | 12/2004 |
| WO | WO 2005/007196 A2 | 1/2005 |
| WO | WO 2005/026372 A1 | 3/2005 |
| WO | WO 2005/035764 A1 | 4/2005 |
| WO | WO 2005/120152 A2 | 12/2005 |
| WO | WO 2006/002538 A1 | 1/2006 |
| WO | WO 2006/053430 A1 | 5/2006 |
| WO | WO 2007/056861 A1 | 5/2007 |
| WO | WO 2010/048228 A2 | 4/2010 |
| WO | WO 2010/088537 A2 | 8/2010 |
| WO | WO 2010/105209 A1 | 9/2010 |

OTHER PUBLICATIONS

Behr, J.-P., "Synthetic Gene-Transfer Vectors," Acc. Chem. Res., 1993, vol. 26, pp. 274-278.

Brigham, K., et al., "Rapid Communication: In vivo Transfection of Murine Lungs with a Functioning Prokaryotic Gene Using a Liposome Vehicle," The American Journal of the Medical Sciences, vol. 298, No. 4, pp. 278-281, 1989.

Brummelkamp, et al., "A System for Stable Expression of Short Interfering RNAs in Mammalian Cells," Science, 2002, V. 296. pp. 550-553.

Cevc, G., "How Membrane Chain-Melting Phase-Transition Temperature is Affected by the Lipid Chain Asymmetry and Degree of Unsaturation: An Effective Chain-Length Model," Biochemistry, 1991, vol. 30, pp. 7186-7193.

Chonn et al., "Recent advances in liposomal drug-delivery systems," Current Opinion in Biotechnology, 1995, vol. 6, pp. 698-708.

Cortesi, R., et al., "Effect of cationic liposome composition on in vitro cytotoxicity and protective effect on carried DNA," International Journal of Pharmaceutics, 1996, vol. 139, pp. 69-78.

Crystal, R., "Transfer of Genes to Humans: Early Lessons and Obstacles to Success," Science, 1995, vol. 270, pp. 404-410.

Culver K., "The First Human Gene Therapy Experiment," Gene Therapy: A Handbook for Physicians, 1994, pp. 33-40.

Duzgunes, N., "Membrane Fusion," Subcellular Biochemistry, 1985, vol. 11, pp. 195-286.

Dwarki, V.J., et al., "Cationic Liposome-Mediated RNA Transfection," Methods in Enzymology, 1993, vol. 217, pp. 644-654.

Elbashir, et a., "Duplexes of 21-nucleotide RNAs mediate RNA interference in cultured mammalian cells," Nature, May 2001, pp. 494-498, vol. 411.

Enoch, H., et al., "Formation and properties of 1000-Å-diameter, single-bilayer phospholipid vesicles," Proc. Natl. Acad. Sci. USA, 1979, vol. 76, No. 1, pp. 145-149.

Felgner, J., et al., "Cationic Lipid-Mediated Transfection in Mammalian Cells: 'Lipofection,'" J. Tiss. Cult. Meth., 1993, vol. 15, pp. 63-68.

Felgner, J., et al., "Enhanced Gene Delivery and Mechanism Studies with a Novel Series of Cationic Lipid Formulations," The Journal of Biological Chemistry, 1994, vol. 269, No. 4, pp. 2550-2561.

Felgner, P., et al., "Lipofection: A highly efficient, lipid-mediated DNA-transfection procedure," Proc. Natl. Acad. Sci. USA, 1987, vol. 84, pp. 7413-7417.

Felgner, P.L., et al., "Cationic Liposome Mediated Transfection," Proc. West. Pharmacol. Soc., 1989, vol. 32, pp. 115-121.

Gao, X., et al., "A Novel Cationic Liposome Reagent for Efficient Transfection of Mammalian Cells," Biochem. Biophys. Res. Comm., 1991, vol. 179, No. 1, pp. 280-285.

Gershon, H., et al., "Mode of Formation and Structural Feature of DNA-Cationic Liposome Complexes Used for Transfection," Biochemistry, 1993, vol. 32, pp. 7143-7151.

Global Newswire, retrieved from http://globalnewswire.com on Feb. 27, 2013, Tekmira sues Alnylam Pharmaceuticals for repeated misuse of tradesecrets and confidential information, Mar. 16, 2011, pp. 1-3.

Guy-Caffey, J., et al., "Novel Polyaminolipids Enhance the Cellular Uptake of Oligonucleotides," The Journal of Biological Chemistry, 1995, vol. 270, No. 52, pp. 31391-31396.

Hawley-Nelson, P., et al., "LipofectAmine™ Reagent: A New, Higher Efficiency Polycationic Liposome Transfection Reagent," Focus, 1993, vol. 15, No. 3, pp. 73-80.

Heyes et al., "Cationic lipid saturation influences intracellular delivery of encapsulated nucleic acids," Journal of Controlled Release, 2005, vol. 107, pp. 276-287.

Heyes et al., "Synthesis of novel cationic lipids: effect of structural modification on the efficiency of gene transfer," J. Med. Chem., 2002, vol. 45, pp. 99-114.

Hyde, S., et al., "Correction of the ion transport defect in cystic fibrosis transgenic mice by gene therapy," Nature, 1993, vol. 362, pp. 250-255.

Jiang, L., et al., "Comparison of protein precipitation methods for sample preparation prior to proteomic analysis," Journal of Chromatography A, 2004, vol. 1023, pp. 317-320.

Juliano, R., et al., "The Effect of Particle Size and Charge on the Clearance Rates of Liposomes and Liposome Encapsulated Drugs," Biochem. Biophys. Res. Commun., 1975, vol. 63, No. 3, pp. 651-658.

Keough, K., "Influence of chain unsaturation and chain position on thermotropism and intermolecular interactions in membranes," Biochem. Soc. Transactions, 1990, vol. 18, No. 5, pp. 835-837.

Lawrence et al. "The formation, characterization and stability of non-ionic surfactant vesicles," S.T.P. Pharma Sciences, 1996, vol. 6, No. 1, pp. 49-60.

Lawrence et al., "Synthesis and aggregation properties of dialkyl polyoxyethylene glycerol ethers," Chemistry and Physics of Lipids, 1996, 82(2):89-100.

Legendre, J.-Y. et al., "Delivery of Plasmid DNA into Mammalian Cell Lines Using pH-Sensitive Liposomes: Comparison with Cationic Liposomes," Pharm. Res., 1992, vol. 9, No. 10, pp. 1235-1242.

Leventis, R., et al., "Interactions of mammalian cells with lipid dispersions containing novel metabolizable cationic amphiphiles," Biochem. Biophys. Acta, 1990, vol. 1023, pp. 124-132.

Liu, et al., "Cationic Liposome-mediated Intravenous Gene Delivery", J. Biol. Chem., 1995, V. 270, pp. 24864-24870.

Marshall, E., "Gene Therapy's Growing Pains," Science, 1995, vol. 269, pp. 1050-1055.

Murahashi et al., "Synthesis and evaluation of neoglycolipid for liposome modification," Biol. Pharm. Bull., 1997, 20(6):704-707.

Orkin, S., et al., NIH Report, Report and Recommendations of the Panel to Assess the NIH Investment in Research on Gene Therapy, 1995.

Parr et al., Factors influencing the retention and chemical stability of poly(ethylene glycol)-lipid conjugates incorporated into large unilamellar vesicles, Biochimica et Biophysica Acta, 1994, 1195:21-30.

Paul, C., et al., "Effective expression of small interfering RNA in human cells," Nature Biotech., 2002, vol. 20, pp. 505-508.

Puyal, C., et al., "A new cationic liposome encapsulating genetic material: A potential delivery system for polynucleotides," Eur. J. Biochem., 1995, vol. 228, pp. 697-703.

Sawada et al., "Microemulsions in supercritical $CO_2$ utilizing the polyethyleneglycol dialkylglycerol and their use for the solubilization of hydrophiles," Dyes and Pigments, 2005, pp. 64-74, vol. 65.

Shin, et al. "Acid-triggered release via dePEGylation of DOPE liposomes containing acid-labile vinyl ether PEG-lipids," Journal of Controlled Release, 2003, vol. 91, pp. 187-200.

Song et al., "Characterization of the inhibitory effect of PEG-lipid conjugates on the intracellular delivery of plasmid and antisense DNA mediated by cationic lipid liposomes," Biochimica et Biophysica Acta, 2002, 1558:1-13.

Sorensen, et al., "Gene Silencing by Systemic Delivery of Synthetic siRNAs in Adult Mice", J. Biol. Chem., 2003, V. 327, pp. 761-766.

Spagnou, S., et al., "Lipidic Carriers of siRNA: Differences in the Formulation, Cellular Uptake, and Delivery with Plasmid DNA," Biochemistry, 2004, vol. 43, pp. 13348-13356.

Stamatatos, L., et al., "Interactions of Cationic Lipid Vesicles with Negatively Charged Phospholipid Vesicles and Biological Membranes," Biochemistry, 1988, vol. 27, pp. 3917-3925.

Szoka, F., et al., "Comparative Properties and Methods of Preparation of Lipid Vesicles (Liposomes)," Ann. Rev. Biophys. Bioeng., 1980, vol. 9, pp. 467-508.

Szoka, F., et al., "Procedure for preparation of liposomes with large internal aqueous space and high capture by reverse-phase evaporation," Proc. Natl. Acad. Sci. USA, 1978, vol. 75, No. 9, pp. 4194-4198.

Templeton, "Cationic Liposome-mediated Gene Delivery in vivo", Bioscience Reports, 2002, vol. 22, No. 2, pp. 283-295.

Van Der Woude, I., et al., "Parameters influencing the introduction of plasmid DNA into cells by the use of synthetic amphiphiles as a carrier system," Biochimica et Biophysica Acta, 1995, vol. 1240, pp. 34-40.

Wheeler, et al., "Stabilized Plasmid-lipid Particles: Constructions and Characterization," Gene Therapy, V. 6, pp. 271-281, 1999.

Wilson, R., et al., "Counterion-Induced Condensation of Deoxyribonucleic Acid," A Light-Scattering Study, Biochemistry, 1979, vol. 18, No. 11, pp. 2192-2196.

Woodle, M.C., et al., "Versatility in lipid compositions showing prolonged circulation with sterically stabilized liposomes," Biochimica et Biophysica Acta, 1992, vol. 1105, pp. 193-200.

Zhu, N., et al., "Systemic Gene Expression After Intravenous DNA Delivery into Adult Mice," Science, 1993, vol. 261, pp. 209-211.

* cited by examiner x200 mag x400 mag x200 mag x400 mag

LIPID FORMULATIONS FOR NUCLEIC ACID DELIVERY

CROSS-REFERENCES TO RELATED APPLICATIONS

The present application is a continuation of U.S. application Ser. No. 12/424,367 filed Apr. 15, 2009, now U.S. Pat. No. 8,058,069, which application claims priority to U.S. Provisional Application No. 61/045,228, filed Apr. 15, 2008, the disclosures of which are herein incorporated by reference in their entirety for all purposes.

STATEMENT REGARDING FEDERALLY SPONSORED RESEARCH OR DEVELOPMENT

Not applicable.

NAMES OF PARTIES TO A JOINT RESEARCH AGREEMENT

Not applicable.

REFERENCE TO A "SEQUENCE LISTING," A TABLE, OR A COMPUTER PROGRAM LISTING APPENDIX SUBMITTED AS AN ASCII TEXT FILE

The Sequence Listing written in file-77-2.TXT, created on Mar. 13, 2012, 8,192 bytes, machine format IBM-PC, MS-Windows operating system, is hereby incorporated by reference in its entirety for all purposes.

BACKGROUND OF THE INVENTION

RNA interference (RNAi) is an evolutionarily conserved process in which recognition of double-stranded RNA (dsRNA) ultimately leads to posttranscriptional suppression of gene expression. This suppression is mediated by short dsRNA, also called small interfering RNA (siRNA), which induces specific degradation of mRNA through complementary base pairing. In several model systems, this natural response has been developed into a powerful tool for the investigation of gene function (see, e.g., Elbashir et al., *Genes Dev.*, 15:188-200 (2001); Hammond et al., *Nat. Rev. Genet.*, 2:110-119 (2001)). More recently, it was discovered that introducing synthetic 21-nucleotide dsRNA duplexes into mammalian cells could efficiently silence gene expression.

Although the precise mechanism is still unclear, RNAi provides a potential new approach to downregulate or silence the transcription and translation of a gene of interest. For example, it is desirable to modulate (e.g., reduce) the expression of certain genes for the treatment of neoplastic disorders such as cancer. It is also desirable to silence the expression of genes associated with liver diseases and disorders such as hepatitis. It is further desirable to reduce the expression of certain genes for the treatment of atherosclerosis and its manifestations, e.g., hypercholesterolemia, myocardial infarction, and thrombosis.

A safe and effective nucleic acid delivery system is required for RNAi to be therapeutically useful. Viral vectors are relatively efficient gene delivery systems, but suffer from a variety of limitations, such as the potential for reversion to the wild-type as well as immune response concerns. As a result, nonviral gene delivery systems are receiving increasing attention (Worgall et al., *Human Gene Therapy*, 8:37 (1997); Peeters et al., *Human Gene Therapy*, 7:1693 (1996); Yei et al., *Gene Therapy*, 1:192 (1994); Hope et al., *Molecular Membrane Biology*, 15:1 (1998)). Furthermore, viral systems are rapidly cleared from the circulation, limiting transfection to "first-pass" organs such as the lungs, liver, and spleen. In addition, these systems induce immune responses that compromise delivery with subsequent injections.

Plasmid DNA-cationic liposome complexes are currently the most commonly employed nonviral gene delivery vehicles (Felgner, *Scientific American*, 276:102 (1997); Chonn et al., *Current Opinion in Biotechnology*, 6:698 (1995)). For instance, cationic liposome complexes made of an amphipathic compound, a neutral lipid, and a detergent for transfecting insect cells are disclosed in U.S. Pat. No. 6,458,382. Cationic liposome complexes are also disclosed in U.S. Patent Publication No. 20030073640.

Cationic liposome complexes are large, poorly defined systems that are not suited for systemic applications and can elicit considerable toxic side effects (Harrison et al., *Biotechniques*, 19:816 (1995); Li et al., *The Gene*, 4:891 (1997); Tam et al., *Gene Ther.*, 7:1867 (2000)). As large, positively charged aggregates, lipoplexes are rapidly cleared when administered in vivo, with highest expression levels observed in first-pass organs, particularly the lungs (Huang et al., *Nature Biotechnology*, 15:620 (1997); Templeton et al., *Nature Biotechnology*, 15:647 (1997); Hofland et al., *Pharmaceutical Research*, 14:742 (1997)).

Other liposomal delivery systems include, for example, the use of reverse micelles, anionic liposomes, and polymer liposomes. Reverse micelles are disclosed in U.S. Pat. No. 6,429,200. Anionic liposomes are disclosed in U.S. Patent Publication No. 20030026831. Polymer liposomes that incorporate dextrin or glycerol-phosphocholine polymers are disclosed in U.S. Patent Publication Nos. 20020081736 and 20030082103, respectively.

A gene delivery system containing an encapsulated nucleic acid for systemic delivery should be small (i.e., less than about 100 nm diameter) and should remain intact in the circulation for an extended period of time in order to achieve delivery to affected tissues. This requires a highly stable, serum-resistant nucleic acid-containing particle that does not interact with cells and other components of the vascular compartment. The particle should also readily interact with target cells at a disease site in order to facilitate intracellular delivery of a desired nucleic acid.

Recent work has shown that nucleic acids can be encapsulated in small (e.g., about 70 nm diameter) "stabilized plasmid-lipid particles" (SPLP) that consist of a single plasmid encapsulated within a bilayer lipid vesicle (Wheeler et al., *Gene Therapy*, 6:271 (1999)). These SPLPs typically contain the "fusogenic" lipid dioleoylphosphatidylethanolamine (DOPE), low levels of cationic lipid, and are stabilized in aqueous media by the presence of a poly(ethylene glycol) (PEG) coating. SPLPs have systemic application as they exhibit extended circulation lifetimes following intravenous (i.v.) injection, accumulate preferentially at distal tumor sites due to the enhanced vascular permeability in such regions, and can mediate transgene expression at these tumor sites. The levels of transgene expression observed at the tumor site following i.v. injection of SPLPs containing the luciferase marker gene are superior to the levels that can be achieved employing plasmid DNA-cationic liposome complexes (lipoplexes) or naked DNA.

Thus, there remains a strong need in the art for novel and more efficient methods and compositions for introducing nucleic acids such as siRNA into cells. In addition, there is a need in the art for methods of downregulating the expression of genes of interest to treat or prevent diseases and disorders such as cancer and atherosclerosis. The present invention addresses these and other needs.

BRIEF SUMMARY OF THE INVENTION

The present invention provides novel, serum-stable lipid particles comprising one or more active agents or therapeutic agents, methods of making the lipid particles, and methods of delivering and/or administering the lipid particles (e.g., for the treatment of a disease or disorder).

In preferred embodiments, the active agent or therapeutic agent is fully encapsulated within the lipid portion of the lipid particle such that the active agent or therapeutic agent in the lipid particle is resistant in aqueous solution to enzymatic degradation, e.g., by a nuclease or protease. In other preferred embodiments, the lipid particles are substantially non-toxic to mammals such as humans.

In one aspect, the present invention provides lipid particles comprising: (a) one or more active agents or therapeutic agents; (b) one or more cationic lipids comprising from about 50 mol % to about 85 mol % of the total lipid present in the particle; (c) one or more non-cationic lipids comprising from about 13 mol % to about 49.5 mol % of the total lipid present in the particle; and (d) one or more conjugated lipids that inhibit aggregation of particles comprising from about 0.5 mol % to about 2 mol % of the total lipid present in the particle.

More particularly, the present invention provides serum-stable nucleic acid-lipid particles (SNALP) comprising a nucleic acid (e.g., one or more interfering RNA molecules such as siRNA, aiRNA, and/or miRNA), methods of making the SNALP, and methods of delivering and/or administering the SNALP (e.g., for the treatment of a disease or disorder).

In certain embodiments, the nucleic acid-lipid particle (e.g., SNALP) comprises: (a) a nucleic acid (e.g., an interfering RNA); (b) a cationic lipid comprising from about 50 mol % to about 85 mol % of the total lipid present in the particle; (c) a non-cationic lipid comprising from about 13 mol % to about 49.5 mol % of the total lipid present in the particle; and (d) a conjugated lipid that inhibits aggregation of particles comprising from about 0.5 mol % to about 2 mol % of the total lipid present in the particle.

In one preferred embodiment, the nucleic acid-lipid particle (e.g., SNALP) comprises: (a) an siRNA; (b) a cationic lipid comprising from about 56.5 mol % to about 66.5 mol % of the total lipid present in the particle; (c) cholesterol or a derivative thereof comprising from about 31.5 mol % to about 42.5 mol % of the total lipid present in the particle; and (d) a PEG-lipid conjugate comprising from about 1 mol % to about 2 mol % of the total lipid present in the particle. This preferred embodiment of nucleic acid-lipid particle is generally referred to herein as the "1:62" formulation.

In another preferred embodiment, the nucleic acid-lipid particle (e.g., SNALP) comprises: (a) an siRNA; (b) a cationic lipid comprising from about 52 mol % to about 62 mol % of the total lipid present in the particle; (c) a mixture of a phospholipid and cholesterol or a derivative thereof comprising from about 36 mol % to about 47 mol % of the total lipid present in the particle; and (d) a PEG-lipid conjugate comprising from about 1 mol % to about 2 mol % of the total lipid present in the particle. This preferred embodiment of nucleic acid-lipid particle is generally referred to herein as the "1:57" formulation.

The present invention also provides pharmaceutical compositions comprising a lipid particle described herein (e.g., SNALP) and a pharmaceutically acceptable carrier.

In another aspect, the present invention provides methods for introducing an active agent or therapeutic agent (e.g., nucleic acid) into a cell, the method comprising contacting the cell with a lipid particle described herein such as a nucleic acid-lipid particle (e.g., SNALP).

In yet another aspect, the present invention provides methods for the in vivo delivery of an active agent or therapeutic agent (e.g., nucleic acid), the method comprising administering to a mammalian subject a lipid particle described herein such as a nucleic acid-lipid particle (e.g., SNALP).

In a further aspect, the present invention provides methods for treating a disease or disorder in a mammalian subject in need thereof, the method comprising administering to the mammalian subject a therapeutically effective amount of a lipid particle described herein such as a nucleic acid-lipid particle (e.g., SNALP).

Other objects, features, and advantages of the present invention will be apparent to one of skill in the art from the following detailed description and figures.

DETAILED DESCRIPTION OF THE INVENTION

I. Introduction

Figure 1A:
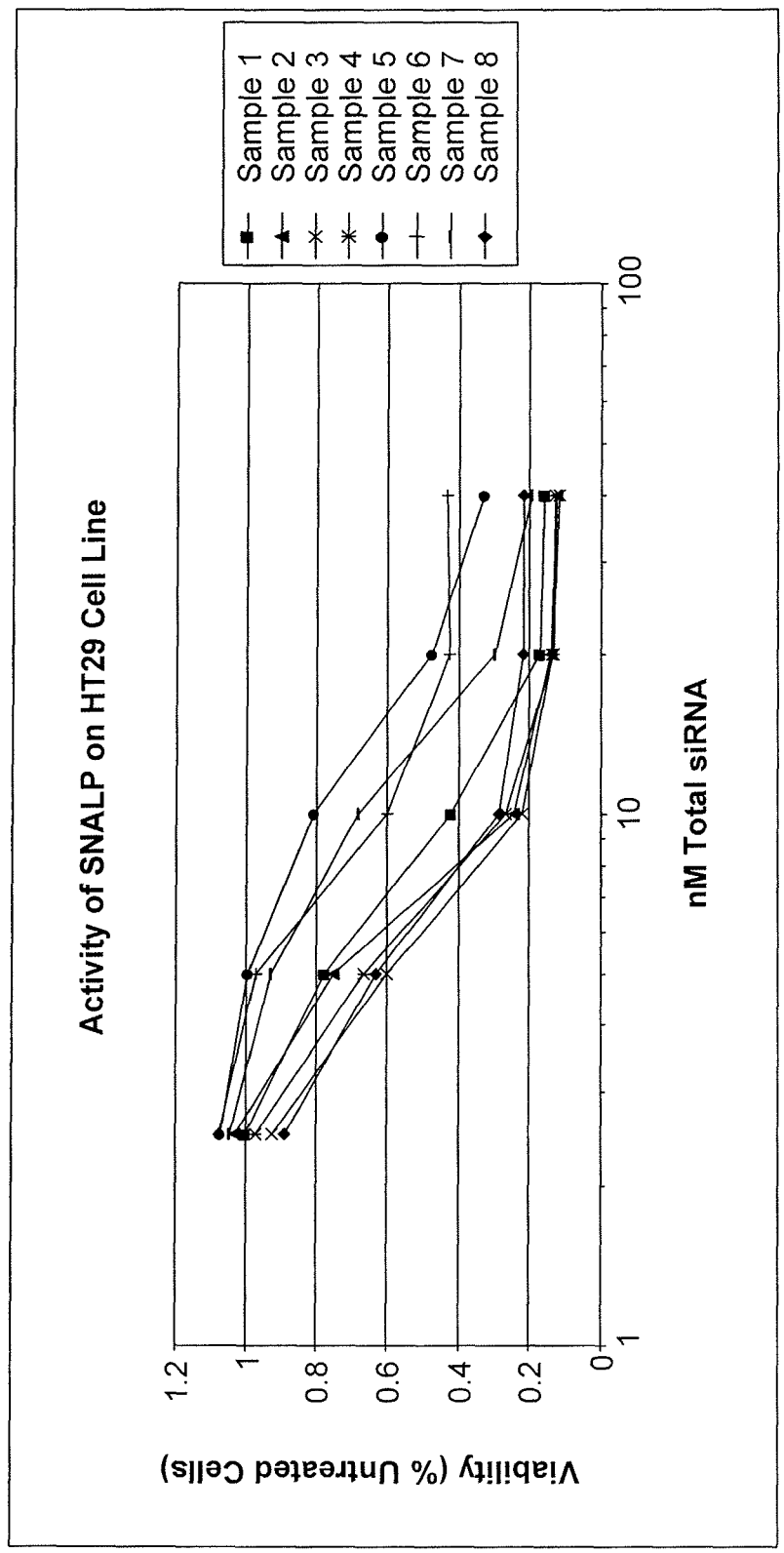
FIG. 1A (Samples 1-8) and FIG. 1B (Samples 9-16 illustrate data demonstrating the activity of 1:57 SNALP containing Eg5 siRNA in a human colon cancer cell line.

The present invention is based, in part, upon the surprising discovery that lipid particles comprising from about 50 mol % to about 85 mol % of a cationic lipid, from about 13 mol % to about 49.5 mol % of a non-cationic lipid, and from about 0.5 mol % to about 2 mol % of a lipid conjugate provide advantages when used for the in vitro or in vivo delivery of an active agent, such as a therapeutic nucleic acid (e.g., an interfering RNA). In particular, as illustrated by the Examples herein, the present invention provides stable nucleic acid-lipid particles (SNALP) that advantageously impart increased activity of the encapsulated nucleic acid (e.g., an interfering RNA such as siRNA) and improved tolerability of the formulations in vivo, resulting in a significant increase in the therapeutic index as compared to nucleic acid-lipid particle compositions previously described. Additionally, the SNALP of the invention are stable in circulation, e.g., resistant to degradation by nucleases in serum, and are substantially non-toxic to mammals such as humans. As a non-limiting example, FIG. 3 of Example 4 shows that one SNALP embodiment of the invention ("1:57 SNALP") was more than 10 times as efficacious as compared to a nucleic acid-lipid particle previously described ("2:30 SNALP") in mediating target gene silencing at a 10-fold lower dose. Similarly, FIG. 2 of Example 3 shows that the "1:57 SNALP" formulation was substantially more effective at silencing the expression of a target gene as compared to nucleic acid-lipid particles previously described ("2:40 SNALP").

In certain embodiments, the present invention provides improved compositions for the delivery of interfering RNA such as siRNA molecules. In particular, the Examples herein illustrate that the improved lipid particle formulations of the invention are highly effective in downregulating the mRNA and/or protein levels of target genes. Furthermore, the Examples herein illustrate that the presence of certain molar ratios of lipid components results in improved or enhanced activity of these lipid particle formulations of the present invention. For instance, the "1:57 SNALP" and "1:62 SNALP" formulations described herein are exemplary formulations of the present invention that are particularly advantageous because they provide improved efficacy and tolerability in vivo, are serum-stable, are substantially non-toxic, are capable of accessing extravascular sites, and are capable of reaching target cell populations.

The lipid particles and compositions of the present invention may be used for a variety of purposes, including the delivery of associated or encapsulated therapeutic agents to cells, both in vitro and in vivo. Accordingly, the present invention provides methods for treating diseases or disorders in a subject in need thereof, by contacting the subject with a lipid particle described herein comprising one or more suitable therapeutic agents.

Various exemplary embodiments of the lipid particles of the invention, as well as compositions and formulations comprising the same, and their use to deliver therapeutic agents and modulate target gene and protein expression, are described in further detail below.

II. Definitions

As used herein, the following terms have the meanings ascribed to them unless specified otherwise.

The term "interfering RNA" or "RNAi" or "interfering RNA sequence" refers to single-stranded RNA (e.g., mature miRNA) or double-stranded RNA (i.e., duplex RNA such as siRNA, aiRNA, or pre-miRNA) that is capable of reducing or inhibiting the expression of a target gene or sequence (e.g., by mediating the degradation or inhibiting the translation of mRNAs which are complementary to the interfering RNA sequence) when the interfering RNA is in the same cell as the target gene or sequence. Interfering RNA thus refers to the single-stranded RNA that is complementary to a target mRNA sequence or to the double-stranded RNA formed by two complementary strands or by a single, self-complementary strand. Interfering RNA may have substantial or complete identity to the target gene or sequence, or may comprise a region of mismatch (i.e., a mismatch motif). The sequence of the interfering RNA can correspond to the full-length target gene, or a subsequence thereof.

Interfering RNA includes "small-interfering RNA" or "siRNA," e.g., interfering RNA of about 15-60, 15-50, or 15-40 (duplex) nucleotides in length, more typically about 15-30, 15-25, or 19-25 (duplex) nucleotides in length, and is preferably about 20-24, 21-22, or 21-23 (duplex) nucleotides in length (e.g., each complementary sequence of the double-stranded siRNA is 15-60, 15-50, 15-40, 15-30, 15-25, or 19-25 nucleotides in length, preferably about 20-24, 21-22, or 21-23 nucleotides in length, and the double-stranded siRNA is about 15-60, 15-50, 15-40, 15-30, 15-25, or 19-25 base pairs in length, preferably about 18-22, 19-20, or 19-21 base pairs in length). siRNA duplexes may comprise 3' overhangs of about 1 to about 4 nucleotides or about 2 to about 3 nucleotides and 5' phosphate termini. Examples of siRNA include, without limitation, a double-stranded polynucleotide molecule assembled from two separate stranded molecules, wherein one strand is the sense strand and the other is the complementary antisense strand; a double-stranded polynucleotide molecule assembled from a single stranded molecule, where the sense and antisense regions are linked by a nucleic acid-based or non-nucleic acid-based linker; a double-stranded polynucleotide molecule with a hairpin secondary structure having self-complementary sense and antisense regions; and a circular single-stranded polynucleotide molecule with two or more loop structures and a stem having self-complementary sense and antisense regions, where the circular polynucleotide can be processed in vivo or in vitro to generate an active double-stranded siRNA molecule.

Preferably, siRNA are chemically synthesized. siRNA can also be generated by cleavage of longer dsRNA (e.g., dsRNA greater than about 25 nucleotides in length) with the *E. coli* RNase III or Dicer. These enzymes process the dsRNA into biologically active siRNA (see, e.g., Yang et al., *Proc. Natl. Acad. Sci. USA*, 99:9942-9947 (2002); Calegari et al., *Proc. Natl. Acad. Sci. USA*, 99:14236 (2002); Byrom et al., *Ambion TechNotes*, 10(1):4-6 (2003); Kawasaki et al., *Nucleic Acids Res.*, 31:981-987 (2003); Knight et al., *Science*, 293:2269-2271 (2001); and Robertson et al., *J. Biol. Chem.*, 243:82 (1968)). Preferably, dsRNA are at least 50 nucleotides to about 100, 200, 300, 400, or 500 nucleotides in length. A dsRNA may be as long as 1000, 1500, 2000, 5000 nucleotides in length, or longer. The dsRNA can encode for an entire gene transcript or a partial gene transcript. In certain instances, siRNA may be encoded by a plasmid (e.g., transcribed as sequences that automatically fold into duplexes with hairpin loops).

As used herein, the term "mismatch motif" or "mismatch region" refers to a portion of an interfering RNA (e.g., siRNA, aiRNA, miRNA) sequence that does not have 100% complementarity to its target sequence. An interfering RNA may have at least one, two, three, four, five, six, or more mismatch regions. The mismatch regions may be contiguous or may be separated by 1, 2, 3, 4, 5, 6, 7, 8, 9, 10, 11, 12, or more nucleotides. The mismatch motifs or regions may comprise a single nucleotide or may comprise two, three, four, five, or more nucleotides.

An "effective amount" or "therapeutically effective amount" of an active agent or therapeutic agent such as an interfering RNA is an amount sufficient to produce the desired effect, e.g., an inhibition of expression of a target sequence in comparison to the normal expression level detected in the absence of an interfering RNA. Inhibition of expression of a target gene or target sequence is achieved when the value obtained with an interfering RNA relative to the control is about 90%, 85%, 80%, 75%, 70%, 65%, 60%, 55%, 50%, 45%, 40%, 35%, 30%, 25%, 20%, 15%, 10%, 5%, or 0%. Suitable assays for measuring expression of a target gene or target sequence include, e.g., examination of protein or RNA levels using techniques known to those of skill in the art such as dot blots, northern blots, in situ hybridization, ELISA, immunoprecipitation, enzyme function, as well as phenotypic assays known to those of skill in the art.

By "decrease," "decreasing," "reduce," or "reducing" of an immune response by an interfering RNA is intended to mean a detectable decrease of an immune response to a given interfering RNA (e.g., a modified interfering RNA). The amount of decrease of an immune response by a modified interfering RNA may be determined relative to the level of an immune response in the presence of an unmodified interfering RNA. A detectable decrease can be about 5%, 10%, 15%, 20%, 25%, 30%, 35%, 40%, 45%, 50%, 55%, 60%, 65%, 70%, 75%, 80%, 85%, 90%, 95%, 100%, or more lower than the immune response detected in the presence of the unmodified interfering RNA. A decrease in the immune response to interfering RNA is typically measured by a decrease in cytokine production (e.g., IFNγ, IFNα, TNFα, IL-6, or IL-12) by a responder cell in vitro or a decrease in cytokine production in the sera of a mammalian subject after administration of the interfering RNA.

As used herein, the term "responder cell" refers to a cell, preferably a mammalian cell, that produces a detectable immune response when contacted with an immunostimulatory interfering RNA such as an unmodified siRNA. Exemplary responder cells include, e.g., dendritic cells, macrophages, peripheral blood mononuclear cells (PBMCs), splenocytes, and the like. Detectable immune responses include, e.g., production of cytokines or growth factors such as TNF-α, IFN-α, IFN-β, IFN-γ, IL-1, IL-2, IL-3, IL-4, IL-5, IL-6, IL-10, IL-12, IL-13, TGF, and combinations thereof.

"Substantial identity" refers to a sequence that hybridizes to a reference sequence under stringent conditions, or to a sequence that has a specified percent identity over a specified region of a reference sequence.

The phrase "stringent hybridization conditions" refers to conditions under which a nucleic acid will hybridize to its target sequence, typically in a complex mixture of nucleic acids, but to no other sequences. Stringent conditions are sequence-dependent and will be different in different circumstances. Longer sequences hybridize specifically at higher temperatures. An extensive guide to the hybridization of nucleic acids is found in Tijssen, *Techniques in Biochemistry and Molecular Biology—Hybridization with Nucleic Probes*, "Overview of principles of hybridization and the strategy of nucleic acid assays" (1993). Generally, stringent conditions are selected to be about 5-10° C. lower than the thermal melting point ($T_m$) for the specific sequence at a defined ionic strength pH. The $T_m$ is the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions may also be achieved with the addition of destabilizing agents such as formamide. For selective or specific hybridization, a positive signal is at least two times background, preferably 10 times background hybridization.

Exemplary stringent hybridization conditions can be as follows: 50% formamide, 5×SSC, and 1% SDS, incubating at 42° C., or, 5×SSC, 1% SDS, incubating at 65° C., with wash in 0.2×SSC, and 0.1% SDS at 65° C. For PCR, a temperature of about 36° C. is typical for low stringency amplification, although annealing temperatures may vary between about 32° C. and 48° C. depending on primer length. For high stringency PCR amplification, a temperature of about 62° C. is typical, although high stringency annealing temperatures can range from about 50° C. to about 65° C., depending on the primer length and specificity. Typical cycle conditions for both high and low stringency amplifications include a denaturation phase of 90° C.-95° C. for 30 sec.-2 min., an annealing phase lasting 30 sec.-2 min., and an extension phase of about 72° C. for 1-2 min. Protocols and guidelines for low and high stringency amplification reactions are provided, e.g., in Innis et al., *PCR Protocols, A Guide to Methods and Applications*, Academic Press, Inc. N.Y. (1990).

Nucleic acids that do not hybridize to each other under stringent conditions are still substantially identical if the polypeptides which they encode are substantially identical. This occurs, for example, when a copy of a nucleic acid is created using the maximum codon degeneracy permitted by the genetic code. In such cases, the nucleic acids typically hybridize under moderately stringent hybridization conditions. Exemplary "moderately stringent hybridization conditions" include a hybridization in a buffer of 40% formamide, 1 M NaCl, 1% SDS at 37° C., and a wash in 1×SSC at 45° C. A positive hybridization is at least twice background. Those of ordinary skill will readily recognize that alternative hybridization and wash conditions can be utilized to provide conditions of similar stringency. Additional guidelines for determining hybridization parameters are provided in numerous references, e.g., Current Protocols in Molecular Biology, Ausubel et al., eds.

The terms "substantially identical" or "substantial identity," in the context of two or more nucleic acids, refer to two or more sequences or subsequences that are the same or have a specified percentage of nucleotides that are the same (i.e., at least about 60%, preferably at least about 65%, 70%, 75%, 80%, 85%, 90%, or 95% identity over a specified region), when compared and aligned for maximum correspondence over a comparison window, or designated region as measured using one of the following sequence comparison algorithms or by manual alignment and visual inspection. This definition, when the context indicates, also refers analogously to the complement of a sequence. Preferably, the substantial identity exists over a region that is at least about 5, 10, 15, 20, 25, 30, 35, 40, 45, 50, 55, or 60 nucleotides in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window," as used herein, includes reference to a segment of any one of a number of contiguous positions selected from the group consisting of from about 5 to about 60, usually about 10 to about 45, more usually about 15 to about 30, in which a sequence may be compared to a reference sequence of the same number of contiguous positions after the two sequences are optimally aligned. Methods of alignment of sequences for comparison are well known in the art. Optimal alignment of sequences for comparison can be conducted, e.g., by the local homology algorithm of Smith and Waterman, *Adv. Appl. Math.*, 2:482 (1981), by the homology alignment algorithm of Needleman and Wunsch, *J. Mol. Biol.*, 48:443 (1970), by the search for similarity method of Pearson and Lipman, *Proc. Natl. Acad. Sci. USA*, 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., *Current Protocols in Molecular Biology*, Ausubel et al., eds. (1995 supplement)).

A preferred example of algorithms that are suitable for determining percent sequence identity and sequence similarity are the BLAST and BLAST 2.0 algorithms, which are described in Altschul et al., *Nuc. Acids Res.*, 25:3389-3402 (1977) and Altschul et al., *J. Mol. Biol.*, 215:403-410 (1990), respectively. BLAST and BLAST 2.0 are used, with the parameters described herein, to determine percent sequence identity for the nucleic acids of the invention. Software for performing BLAST analyses is publicly available through the National Center for Biotechnology Information (www.ncbi.nlm.nih.gov/).

The BLAST algorithm also performs a statistical analysis of the similarity between two sequences (see, e.g., Karlin and Altschul, *Proc. Natl. Acad. Sci. USA*, 90:5873-5787 (1993)). One measure of similarity provided by the BLAST algorithm is the smallest sum probability (P(N)), which provides an indication of the probability by which a match between two nucleotide sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

The term "nucleic acid" as used herein refers to a polymer containing at least two deoxyribonucleotides or ribonucleotides in either single- or double-stranded form and includes DNA and RNA. DNA may be in the form of, e.g., antisense molecules, plasmid DNA, pre-condensed DNA, a PCR product, vectors (P1, PAC, BAC, YAC, artificial chromosomes), expression cassettes, chimeric sequences, chromosomal DNA, or derivatives and combinations of these groups. RNA may be in the form of siRNA, asymmetrical interfering RNA (aiRNA), microRNA (miRNA), mRNA, tRNA, rRNA, tRNA, viral RNA (vRNA), and combinations thereof. Nucleic acids include nucleic acids containing known nucleotide analogs or modified backbone residues or linkages, which are synthetic, naturally occurring, and non-naturally occurring, and which have similar binding properties as the reference nucleic acid. Examples of such analogs include, without limitation, phosphorothioates, phosphoramidates, methyl phosphonates, chiral-methyl phosphonates, 2'-O-methyl ribonucleotides, and peptide-nucleic acids (PNAs). Unless specifically limited, the term encompasses nucleic acids containing known analogues of natural nucleotides that have similar binding properties as the reference nucleic acid. Unless otherwise indicated, a particular nucleic acid sequence also implicitly encompasses conservatively modified variants thereof (e.g., degenerate codon substitutions), alleles, orthologs, SNPs, and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.*, 19:5081 (1991); Ohtsuka et al., *J. Biol. Chem.*, 260:2605-2608 (1985); Rossolini et al., *Mol. Cell. Probes*, 8:91-98 (1994)). "Nucleotides" contain a sugar deoxyribose (DNA) or ribose (RNA), a base, and a phosphate group. Nucleotides are linked together through the phosphate groups. "Bases" include purines and pyrimidines, which further include natural compounds adenine, thymine, guanine, cytosine, uracil, inosine, and natural analogs, and synthetic derivatives of purines and pyrimidines, which include, but are not limited to, modifications which place new reactive groups such as, but not limited to, amines, alcohols, thiols, carboxylates, and alkylhalides.

The term "gene" refers to a nucleic acid (e.g., DNA or RNA) sequence that comprises partial length or entire length coding sequences necessary for the production of a polypeptide or precursor polypeptide.

"Gene product," as used herein, refers to a product of a gene such as an RNA transcript or a polypeptide.

The term "lipid" refers to a group of organic compounds that include, but are not limited to, esters of fatty acids and are characterized by being insoluble in water, but soluble in many organic solvents. They are usually divided into at least three classes: (1) "simple lipids," which include fats and oils as well as waxes; (2) "compound lipids," which include phospholipids and glycolipids; and (3) "derived lipids" such as steroids.

A "lipid particle" is used herein to refer to a lipid formulation that can be used to deliver an active agent or therapeutic agent, such as a nucleic acid (e.g., an interfering RNA), to a target site of interest. In the lipid particle of the invention, which is typically formed from a cationic lipid, a non-cationic lipid, and a conjugated lipid that prevents aggregation of the particle, the active agent or therapeutic agent may be encapsulated in the lipid, thereby protecting the agent from enzymatic degradation.

As used herein, the term "SNALP" refers to a stable nucleic acid-lipid particle. A SNALP represents a particle made from lipids (e.g., a cationic lipid, a non-cationic lipid, and a conjugated lipid that prevents aggregation of the particle), wherein the nucleic acid (e.g., siRNA, aiRNA, miRNA, ssDNA, dsDNA, ssRNA, short hairpin RNA (shRNA), dsRNA, or a plasmid, including plasmids from which an interfering RNA is transcribed) is fully encapsulated within the lipid. As used herein, the term "SNALP" includes an SPLP, which is the term used to refer to a nucleic acid-lipid particle comprising a nucleic acid (e.g., a plasmid) encapsulated within the lipid. SNALP and SPLP typically contain a cationic lipid, a non-cationic lipid, and a lipid conjugate (e.g., a PEG-lipid conjugate). SNALP and SPLP are extremely useful for systemic applications, as they can exhibit extended circulation lifetimes following intravenous (i.v.) injection, they can accumulate at distal sites (e.g., sites physically separated from the administration site), and they can mediate expression of the transfected gene or silencing of target gene expression at these distal sites. SPLP include "pSPLP," which comprise an encapsulated condensing agent-nucleic acid complex as set forth in PCT Publication No. WO 00/03683, the disclosure of which is herein incorporated by reference in its entirety for all purposes.

The lipid particles of the invention (e.g., SNALP) typically have a mean diameter of from about 40 nm to about 150 nm, from about 50 nm to about 150 nm, from about 60 nm to about 130 nm, from about 70 nm to about 110 nm, or from about 70 to about 90 nm, and are substantially non-toxic. In addition, nucleic acids, when present in the lipid particles of the invention, are resistant in aqueous solution to degradation with a nuclease. Nucleic acid-lipid particles and their method of preparation are disclosed in, e.g., U.S. Patent Publication Nos. 20040142025 and 20070042031, the disclosures of which are herein incorporated by reference in their entirety for all purposes.

As used herein, "lipid encapsulated" can refer to a lipid particle that provides an active agent or therapeutic agent, such as a nucleic acid (e.g., an interfering RNA), with full encapsulation, partial encapsulation, or both. In a preferred embodiment, the nucleic acid is fully encapsulated in the lipid particle (e.g., to form an SPLP, pSPLP, SNALP, or other nucleic acid-lipid particle).

The term "lipid conjugate" refers to a conjugated lipid that inhibits aggregation of lipid particles. Such lipid conjugates include, but are not limited to, polyamide oligomers (e.g., ATTA-lipid conjugates), PEG-lipid conjugates, such as PEG coupled to dialkyloxypropyls, PEG coupled to diacylglycerols, PEG coupled to cholesterol, PEG coupled to phosphatidylethanolamines, PEG conjugated to ceramides (see, e.g., U.S. Pat. No. 5,885,613, the disclosure of which is herein incorporated by reference in its entirety for all purposes), cationic PEG lipids, and mixtures thereof. PEG can be conjugated directly to the lipid or may be linked to the lipid via a linker moiety. Any linker moiety suitable for coupling the PEG to a lipid can be used including, e.g., non-ester containing linker moieties and ester-containing linker moieties. In preferred embodiments, non-ester containing linker moieties are used.

The term "amphipathic lipid" refers, in part, to any suitable material wherein the hydrophobic portion of the lipid material orients into a hydrophobic phase, while the hydrophilic portion orients toward the aqueous phase. Hydrophilic characteristics derive from the presence of polar or charged groups such as carbohydrates, phosphate, carboxylic, sulfato, amino, sulfhydryl, nitro, hydroxyl, and other like groups. Hydrophobicity can be conferred by the inclusion of apolar groups that include, but are not limited to, long-chain saturated and unsaturated aliphatic hydrocarbon groups and such groups substituted by one or more aromatic, cycloaliphatic, or heterocyclic group(s). Examples of amphipathic compounds include, but are not limited to, phospholipids, aminolipids, and sphingolipids.

Representative examples of phospholipids include, but are not limited to, phosphatidylcholine, phosphatidylethanolamine, phosphatidylserine, phosphatidylinositol, phosphatidic acid, palmitoyloleoyl phosphatidylcholine, lysophosphatidylcholine, lysophosphatidylethanolamine, dipalmitoylphosphatidylcholine, dioleoylphosphatidylcholine, distearoylphosphatidylcholine, and dilinoleoylphosphatidylcholine. Other compounds lacking in phosphorus, such as sphingolipid, glycosphingolipid families, diacylglycerols, and β-acyloxyacids, are also within the group designated as amphipathic lipids. Additionally, the amphipathic lipids described above can be mixed with other lipids including triglycerides and sterols.

The term "neutral lipid" refers to any of a number of lipid species that exist either in an uncharged or neutral zwitterionic form at a selected pH. At physiological pH, such lipids include, for example, diacylphosphatidylcholine, diacylphosphatidylethanolamine, ceramide, sphingomyelin, cephalin, cholesterol, cerebrosides, and diacylglycerols.

The term "non-cationic lipid" refers to any amphipathic lipid as well as any other neutral lipid or anionic lipid.

The term "anionic lipid" refers to any lipid that is negatively charged at physiological pH. These lipids include, but are not limited to, phosphatidylglycerols, cardiolipins, diacylphosphatidylserines, diacylphosphatidic acids, N-dodecanoyl phosphatidylethanolamines, N-succinyl phosphatidylethanolamines, N-glutarylphosphatidylethanolamines, lysylphosphatidylglycerols, palmitoyloleyolphosphatidylglycerol (POPG), and other anionic modifying groups joined to neutral lipids.

The term "cationic lipid" refers to any of a number of lipid species that carry a net positive charge at a selected pH, such as physiological pH (e.g., pH of about 7.0). It has been surprisingly found that cationic lipids comprising alkyl chains with multiple sites of unsaturation, e.g., at least two or three sites of unsaturation, are particularly useful for forming lipid particles with increased membrane fluidity. A number of cationic lipids and related analogs, which are also useful in the present invention, have been described in U.S. Patent Publication Nos. 20060083780 and 20060240554; U.S. Pat. Nos. 5,208,036; 5,264,618; 5,279,833; 5,283,185; 5,753,613; and 5,785,992; and PCT Publication No. WO 96/10390, the disclosures of which are herein incorporated by reference in their entirety for all purposes. Non-limiting examples of cationic lipids are described in detail herein. In some cases, the cationic lipids comprise a protonatable tertiary amine (e.g., pH titratable) head group, C18 alkyl chains, ether linkages between the head group and alkyl chains, and 0 to 3 double bonds. Such lipids include, e.g., DSDMA, DLinDMA, DLenDMA, and DODMA.

The term "hydrophobic lipid" refers to compounds having apolar groups that include, but are not limited to, long-chain saturated and unsaturated aliphatic hydrocarbon groups and such groups optionally substituted by one or more aromatic, cycloaliphatic, or heterocyclic group(s). Suitable examples include, but are not limited to, diacylglycerol, dialkylglycerol, N-N-dialkylamino, 1,2-diacyloxy-3-aminopropane, and 1,2-dialkyl-3-aminopropane.

The term "fusogenic" refers to the ability of a lipid particle, such as a SNALP, to fuse with the membranes of a cell. The membranes can be either the plasma membrane or membranes surrounding organelles, e.g., endosome, nucleus, etc.

As used herein, the term "aqueous solution" refers to a composition comprising in whole, or in part, water.

As used herein, the term "organic lipid solution" refers to a composition comprising in whole, or in part, an organic solvent having a lipid.

"Distal site," as used herein, refers to a physically separated site, which is not limited to an adjacent capillary bed, but includes sites broadly distributed throughout an organism.

"Serum-stable" in relation to nucleic acid-lipid particles such as SNALP means that the particle is not significantly degraded after exposure to a serum or nuclease assay that would significantly degrade free DNA or RNA. Suitable assays include, for example, a standard serum assay, a DNAse assay, or an RNAse assay.

"Systemic delivery," as used herein, refers to delivery of lipid particles that leads to a broad biodistribution of an active agent or therapeutic agent such as an interfering RNA within an organism. Some techniques of administration can lead to the systemic delivery of certain agents, but not others. Systemic delivery means that a useful, preferably therapeutic, amount of an agent is exposed to most parts of the body. To obtain broad biodistribution generally requires a blood lifetime such that the agent is not rapidly degraded or cleared (such as by first pass organs (liver, lung, etc.) or by rapid, nonspecific cell binding) before reaching a disease site distal to the site of administration. Systemic delivery of lipid particles can be by any means known in the art including, for example, intravenous, subcutaneous, and intraperitoneal. In a preferred embodiment, systemic delivery of lipid particles is by intravenous delivery.

"Local delivery," as used herein, refers to delivery of an active agent or therapeutic agent such as an interfering RNA directly to a target site within an organism. For example, an agent can be locally delivered by direct injection into a disease site such as a tumor or other target site such as a site of inflammation or a target organ such as the liver, heart, pancreas, kidney, and the like.

The term "mammal" refers to any mammalian species such as a human, mouse, rat, dog, cat, hamster, guinea pig, rabbit, livestock, and the like.

The term "cancer" refers to any member of a class of diseases characterized by the uncontrolled growth of aberrant cells. The term includes all known cancers and neoplastic conditions, whether characterized as malignant, benign, soft tissue, or solid, and cancers of all stages and grades including pre- and post-metastatic cancers. Examples of different types of cancer include, but are not limited to, lung cancer, colon cancer, rectal cancer, anal cancer, bile duct cancer, small intestine cancer, stomach (gastric) cancer, esophageal cancer; gallbladder cancer, liver cancer, pancreatic cancer, appendix cancer, breast cancer, ovarian cancer; cervical cancer, prostate cancer, renal cancer (e.g., renal cell carcinoma), cancer of the central nervous system, glioblastoma, skin cancer, lymphomas, choriocarcinomas, head and neck cancers, osteogenic sarcomas, and blood cancers. Non-limiting examples of specific types of liver cancer include hepatocellular carcinoma (HCC), secondary liver cancer (e.g., caused by metastasis of some other non-liver cancer cell type), and hepatoblastoma. As used herein, a "tumor" comprises one or more cancerous cells.

III. Description of the Embodiments

The present invention provides novel, serum-stable lipid particles comprising one or more active agents or therapeutic agents, methods of making the lipid particles, and methods of delivering and/or administering the lipid particles (e.g., for the treatment of a disease or disorder).

In one aspect, the present invention provides lipid particles comprising: (a) one or more active agents or therapeutic agents; (b) one or more cationic lipids comprising from about 50 mol % to about 85 mol % of the total lipid present in the particle; (c) one or more non-cationic lipids comprising from about 13 mol % to about 49.5 mol % of the total lipid present in the particle; and (d) one or more conjugated lipids that inhibit aggregation of particles comprising from about 0.5 mol % to about 2 mol % of the total lipid present in the particle.

In certain embodiments, the active agent or therapeutic agent is fully encapsulated within the lipid portion of the lipid particle such that the active agent or therapeutic agent in the lipid particle is resistant in aqueous solution to enzymatic degradation, e.g., by a nuclease or protease. In certain other embodiments, the lipid particles are substantially non-toxic to mammals such as humans.

In some embodiments, the active agent or therapeutic agent comprises a nucleic acid. In certain instances, the nucleic acid comprises an interfering RNA molecule such as, e.g., an siRNA, aiRNA, miRNA, or mixtures thereof. In certain other instances, the nucleic acid comprises single-stranded or double-stranded DNA, RNA, or a DNA/RNA hybrid such as, e.g., an antisense oligonucleotide, a ribozyme, a plasmid, an immunostimulatory oligonucleotide, or mixtures thereof.

In other embodiments, the active agent or therapeutic agent comprises a peptide or polypeptide. In certain instances, the peptide or polypeptide comprises an antibody such as, e.g., a polyclonal antibody, a monoclonal antibody, an antibody fragment; a humanized antibody, a recombinant antibody, a recombinant human antibody, a Primatized™ antibody, or mixtures thereof. In certain other instances, the peptide or polypeptide comprises a cytokine, a growth factor, an apoptotic factor, a differentiation-inducing factor, a cell-surface receptor, a ligand, a hormone, a small molecule (e.g., small organic molecule or compound), or mixtures thereof.

In preferred embodiments, the active agent or therapeutic agent comprises an siRNA. In one embodiment, the siRNA molecule comprises a double-stranded region of about 15 to about 60 nucleotides in length (e.g., about 15-60, 15-50, 15-40, 15-30, 15-25, or 19-25 nucleotides in length, or 15, 16, 17, 18, 19, 20, 21, 22, 23, 24, or 25 nucleotides in length). The siRNA molecules of the invention are capable of silencing the expression of a target sequence in vitro and/or in vivo.

In some embodiments, the siRNA molecule comprises at least one modified nucleotide. In certain preferred embodiments, the siRNA molecule comprises one, two, three, four, five, six, seven, eight, nine, ten, or more modified nucleotides in the double-stranded region. In certain instances, the siRNA comprises from about 1% to about 100% (e.g., about 1%, 5%, 10%, 15%, 20%, 25%, 30%, 35%, 40%, 45%, 50%, 55%, 60%, 65%, 70%, 75%, 80%, 85%, 90%, 95%, or 100%) modified nucleotides in the double-stranded region. In preferred embodiments, less than about 25% (e.g., less than about 25%, 20%, 15%, 10%, or 5%) or from about 1% to about 25% (e.g., from about 1%-25%, 5%-25%, 10%-25%, 15%-25%, 20%-25%, or 10%-20%) of the nucleotides in the double-stranded region comprise modified nucleotides.

In other embodiments, the siRNA molecule comprises modified nucleotides including, but not limited to, 2'-O-methyl (2'OMe) nucleotides, 2'-deoxy-2'-fluoro(2'F) nucleotides, 2'-deoxy nucleotides, 2'-O-(2-methoxyethyl) (MOE) nucleotides, locked nucleic acid (LNA) nucleotides, and mixtures thereof. In preferred embodiments, the siRNA comprises 2'OMe nucleotides (e.g., 2'OMe purine and/or pyrimidine nucleotides) such as, for example, 2'OMe-guanosine nucleotides, 2'OMe-uridine nucleotides, 2'OMe-adenosine nucleotides, 2'OMe-cytosine nucleotides, and mixtures thereof. In certain instances, the siRNA does not comprise 2'OMe-cytosine nucleotides. In other embodiments, the siRNA comprises a hairpin loop structure.

The siRNA may comprise modified nucleotides in one strand (i.e., sense or antisense) or both strands of the double-stranded region of the siRNA molecule. Preferably, uridine and/or guanosine nucleotides are modified at selective positions in the double-stranded region of the siRNA duplex. With regard to uridine nucleotide modifications, at least one, two, three, four, five, six, or more of the uridine nucleotides in the sense and/or antisense strand can be a modified uridine nucleotide such as a 2'OMe-uridine nucleotide. In some embodiments, every uridine nucleotide in the sense and/or antisense strand is a 2'OMe-uridine nucleotide. With regard to guanosine nucleotide modifications, at least one, two, three, four, five, six, or more of the guanosine nucleotides in the sense and/or antisense strand can be a modified guanosine nucleotide such as a 2'OMe-guanosine nucleotide. In some embodiments, every guanosine nucleotide in the sense and/or antisense strand is a 2'OMe-guanosine nucleotide.

In certain embodiments, at least one, two, three, four, five, six, seven, or more 5'-GU-3' motifs in an siRNA sequence may be modified, e.g., by introducing mismatches to eliminate the 5'-GU-3' motifs and/or by introducing modified nucleotides such as 2'OMe nucleotides. The 5'-GU-3' motif can be in the sense strand, the antisense strand, or both strands of the siRNA sequence. The 5'-GU-3' motifs may be adjacent to each other or, alternatively, they may be separated by 1, 2, 3, 4, 5, 6, 7, 8, 9, 10, 11, 12, or more nucleotides.

In some preferred embodiments, a modified siRNA molecule is less immunostimulatory than a corresponding unmodified siRNA sequence. In such embodiments, the modified siRNA molecule with reduced immunostimulatory properties advantageously retains RNAi activity against the target sequence. In another embodiment, the immunostimulatory properties of the modified siRNA molecule and its ability to silence target gene expression can be balanced or optimized by the introduction of minimal and selective 2'OMe modifications within the siRNA sequence such as, e.g., within the double-stranded region of the siRNA duplex. In certain instances, the modified siRNA is at least about 5%, 10%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99%, or 100% less immunostimulatory than the corresponding unmodified siRNA. It will be readily apparent to those of skill in the art that the immunostimulatory properties of the modified siRNA molecule and the corresponding unmodified siRNA molecule can be determined by, for example, measuring INF-α and/or IL-6 levels from about two to about twelve hours after systemic administration in a mammal or transfection of a mammalian responder cell using an appropriate lipid-based delivery system (such as the SNALP delivery system disclosed herein).

In certain embodiments, a modified siRNA molecule has an $IC_{50}$ (i.e., half-maximal inhibitory concentration) less than or equal to ten-fold that of the corresponding unmodified siRNA (i.e., the modified siRNA has an $IC_{50}$ that is less than or equal to ten-times the $IC_{50}$ of the corresponding unmodified siRNA). In other embodiments, the modified siRNA has an $IC_{50}$ less than or equal to three-fold that of the corresponding unmodified siRNA sequence. In yet other embodiments, the modified siRNA has an $IC_{50}$ less than or equal to two-fold that of the corresponding unmodified siRNA. It will be readily apparent to those of skill in the art that a dose-response curve can be generated and the $IC_{50}$ values for the modified siRNA and the corresponding unmodified siRNA can be readily determined using methods known to those of skill in the art.

In yet another embodiment, a modified siRNA molecule is capable of silencing at least about 5%, 10%, 15%, 20%, 25%, 30%, 35%, 40%, 45%, 50%, 55%, 60%, 65%, 70%, 75%, 80%, 85%, 90%, 95%, or 100% of the expression of the target sequence relative to the corresponding unmodified siRNA sequence.

In some embodiments, the siRNA molecule does not comprise phosphate backbone modifications, e.g., in the sense and/or antisense strand of the double-stranded region. In other embodiments, the siRNA comprises one, two, three, four, or more phosphate backbone modifications, e.g., in the sense and/or antisense strand of the double-stranded region. In preferred embodiments, the siRNA does not comprise phosphate backbone modifications.

In further embodiments, the siRNA does not comprise 2'-deoxy nucleotides, e.g., in the sense and/or antisense strand of the double-stranded region. In yet further embodiments, the siRNA comprises one, two, three, four, or more 2'-deoxy nucleotides, e.g., in the sense and/or antisense strand of the double-stranded region. In preferred embodiments, the siRNA does not comprise 2'-deoxy nucleotides.

In certain instances, the nucleotide at the 3'-end of the double-stranded region in the sense and/or antisense strand is not a modified nucleotide. In certain other instances, the nucleotides near the 3'-end (e.g., within one, two, three, or four nucleotides of the 3'-end) of the double-stranded region in the sense and/or antisense strand are not modified nucleotides.

The siRNA molecules described herein may have 3' overhangs of one, two, three, four, or more nucleotides on one or both sides of the double-stranded region, or may lack overhangs (i.e., have blunt ends) on one or both sides of the double-stranded region. Preferably, the siRNA has 3' overhangs of two nucleotides on each side of the double-stranded region. In certain instances, the 3' overhang on the antisense strand has complementarity to the target sequence and the 3' overhang on the sense strand has complementarity to a complementary strand of the target sequence. Alternatively, the 3' overhangs do not have complementarity to the target sequence or the complementary strand thereof. In some embodiments, the 3' overhangs comprise one, two, three, four, or more nucleotides such as 2'-deoxy(2'H) nucleotides. In certain preferred embodiments, the 3' overhangs comprise deoxythymidine (dT) and/or uridine nucleotides. In other embodiments, one or more of the nucleotides in the 3' overhangs on one or both sides of the double-stranded region comprise modified nucleotides. Non-limiting examples of modified nucleotides are described above and include 2'OMe nucleotides, 2'-deoxy-2'F nucleotides, 2'-deoxy nucleotides, 2'-O-2-MOE nucleotides, LNA nucleotides, and mixtures thereof. In preferred embodiments, one, two, three, four, or more nucleotides in the 3' overhangs present on the sense and/or antisense strand of the siRNA comprise 2'OMe nucleotides (e.g., 2'OMe purine and/or pyrimidine nucleotides) such as, for example, 2'OMe-guanosine nucleotides, 2'OMe-uridine nucleotides, 2'OMe-adenosine nucleotides, 2'OMe-cytosine nucleotides, and mixtures thereof.

The siRNA may comprise at least one or a cocktail (e.g., at least two, three, four, five, six, seven, eight, nine, ten, or more) of unmodified and/or modified siRNA sequences that silence target gene expression. The cocktail of siRNA may comprise sequences which are directed to the same region or domain (e.g., a "hot spot") and/or to different regions or domains of one or more target genes. In certain instances, one or more (e.g., at least two, three, four, five, six, seven, eight, nine, ten, or more) modified siRNA that silence target gene expression are present in a cocktail. In certain other instances, one or more (e.g., at least two, three, four, five, six, seven, eight, nine, ten, or more) unmodified siRNA sequences that silence target gene expression are present in a cocktail.

In some embodiments, the antisense strand of the siRNA molecule comprises or consists of a sequence that is at least about 80%, 85%, 90%, 95%, 96%, 97%, 98%, or 99% complementary to the target sequence or a portion thereof. In other embodiments, the antisense strand of the siRNA molecule comprises or consists of a sequence that is 100% complementary to the target sequence or a portion thereof. In further embodiments, the antisense strand of the siRNA molecule comprises or consists of a sequence that specifically hybridizes to the target sequence or a portion thereof.

In further embodiments, the sense strand of the siRNA molecule comprises or consists of a sequence that is at least about 80%, 85%, 90%, 95%, 96%, 97%, 98%, or 99% identical to the target sequence or a portion thereof. In additional embodiments, the sense strand of the siRNA molecule comprises or consists of a sequence that is 100% identical to the target sequence or a portion thereof.

In the lipid particles of the invention (e.g., SNALP comprising an interfering RNA such as siRNA), the cationic lipid may comprise, e.g., one or more of the following: 1,2-dilinoleyloxy-N,N-dimethylaminopropane (DLinDMA), 1,2-dilinolenyloxy-N,N-dimethylaminopropane (DLenDMA), 2,2-dilinoleyl-4-(2-dimethylaminoethyl)-[1,3]-dioxolane (DLin-K-C2-DMA; "XTC2"), 2,2-dilinoleyl-4-(3-dimethylaminopropyl)-[1,3]-dioxolane (DLin-K-C3-DMA), 2,2-dilinoleyl-4-(4-dimethylaminobutyl)-[1,3]-dioxolane (DLin-K-C4-DMA), 2,2-dilinoleyl-5-dimethylaminomethyl-[1,3]-dioxane (DLin-K6-DMA), 2,2-dilinoleyl-4-N-methylpepiazino-[1,3]-dioxolane (DLin-K-MPZ), 2,2-dilinoleyl-4-dimethylaminomethyl-[1,3]-dioxolane (DLin-K-DMA), 1,2-dilinoleylcarbamoyloxy-3-dimethylaminopropane (DLin-C-DAP), 1,2-dilinoleyoxy-3-(dimethylamino)acetoxypropane (DLin-DAC), 1,2-dilinoleyoxy-3-morpholinopropane (DLin-MA), 1,2-dilinoleoyl-3-dimethylaminopropane (DLinDAP), 1,2-dilinoleylthio-3-dimethylaminopropane (DLin-S-DMA), 1-linoleoyl-2-linoleyloxy-3-dimethylaminopropane (DLin-2-DMAP), 1,2-dilinoleyloxy-3-trimethylaminopropane chloride salt (DLin-TMA.Cl), 1,2-dilinoleoyl-3-trimethylaminopropane chloride salt (DLin-TAP.Cl), 1,2-dilinoleyloxy-3-(N-methylpiperazino)propane (DLin-MPZ), 3-(N,N-dilinoleylamino)-1,2-propanediol (DLinAP), 3-(N,N-dioleylamino)-1,2-propanedio (DOAP), 1,2-dilinoleyloxo-3-(2-N,N-dimethylamino)ethoxypropane (DLin-EG-DMA), N,N-dioleyl-N,N-dimethylammonium chloride (DODAC), 1,2-dioleyloxy-N,N-dimethylaminopropane (DODMA), 1,2-distearyloxy-N,N-dimethylaminopropane (DSDMA), N-(1-(2,3-dioleyloxy)propyl)-N,N,N-trimethylammonium chloride (DOTMA), N,N-distearyl-N,N-dimethylammonium bromide (DDAB), N-(1-(2,3-dioleoyloxy)propyl)-N,N, N-trimethylammonium chloride (DOTAP), 3-(N-(N',N'-dimethylaminoethane)-carbamoyl)cholesterol (DC-Chol), N-(1, 2-dimyristyloxyprop-3-yl)-N,N-dimethyl-N-hydroxyethyl ammonium bromide (DMRIE), 2,3-dioleyloxy-N-[2(spermine-carboxamido)ethyl]-N,N-dimethyl-1-propanaminiumtrifluoroacetate (DOSPA), dioctadecylamidoglycyl spermine (DOGS), 3-dimethylamino-2-(cholest-5-en-3-beta-oxybutan-4-oxy)-1-(cis,cis-9,12-octadecadienoxy)propane (CLinDMA), 2-[5'-(cholest-5-en-3-beta-oxy)-3'-oxapentoxy)-3-dimethyl-1-(cis,cis-9',1-2'-octadecadienoxy)propane (CpLinDMA), N,N-dimethyl-3,4-dioleyloxybenzylamine (DMOBA), 1,2-N,N'-dioleylcarbamyl-3-dimethylaminopropane (DOcarbDAP), 1,2-N,N'-dilinoleylcarbamyl-3-dimethylaminopropane (DLincarbDAP), or mixtures thereof. In certain preferred embodiments, the cationic lipid is DLinDMA, DLin-K-C2-DMA ("XTC2"), or mixtures thereof.

The synthesis of cationic lipids such as DLin-K-C2-DMA ("XTC2"), DLin-K-C3-DMA, DLin-K-C4-DMA, DLin-K6-DMA, and DLin-K-MPZ, as well as additional cationic lipids, is described in U.S. Provisional Application No. 61/104, 212, filed Oct. 9, 2008, the disclosure of which is herein incorporated by reference in its entirety for all purposes. The synthesis of cationic lipids such as DLin-K-DMA, DLin-C-DAP, DLin-DAC, DLin-MA, DLinDAP, DLin-S-DMA, DLin-2-DMAP, DLin-TMA.Cl, DLin-TAP.Cl, DLin-MPZ, DLinAP, DOAP, and DLin-EG-DMA, as well as additional cationic lipids, is described in PCT Application No. PCT/US08/88676, filed Dec. 31, 2008, the disclosure of which is herein incorporated by reference in its entirety for all purposes. The synthesis of cationic lipids such as CLinDMA, as well as additional cationic lipids, is described in U.S. Patent Publication No. 20060240554, the disclosure of which is herein incorporated by reference in its entirety for all purposes.

In some embodiments, the cationic lipid may comprise from about 50 mol % to about 90 mol %, from about 50 mol % to about 85 mol %, from about 50 mol % to about 80 mol %, from about 50 mol % to about 75 mol %, from about 50 mol % to about 70 mol %, from about 50 mol % to about 65 mol %, or from about 50 mol % to about 60 mol % of the total lipid present in the particle.

In other embodiments, the cationic lipid may comprise from about 55 mol % to about 90 mol %, from about 55 mol % to about 85 mol %, from about 55 mol % to about 80 mol %, from about 55 mol % to about 75 mol %, from about 55 mol % to about 70 mol %, or from about 55 mol % to about 65 mol % of the total lipid present in the particle.

In yet other embodiments, the cationic lipid may comprise from about 60 mol % to about 90 mol %, from about 60 mol % to about 85 mol %, from about 60 mol % to about 80 mol %, from about 60 mol % to about 75 mol %, or from about 60 mol % to about 70 mol % of the total lipid present in the particle.

In still yet other embodiments, the cationic lipid may comprise from about 65 mol % to about 90 mol %, from about 65 mol % to about 85 mol %, from about 65 mol % to about 80 mol %, or from about 65 mol % to about 75 mol % of the total lipid present in the particle.

In further embodiments, the cationic lipid may comprise from about 70 mol % to about 90 mol %, from about 70 mol % to about 85 mol %, from about 70 mol % to about 80 mol %, from about 75 mol % to about 90 mol %, from about 75 mol % to about 85 mol %, or from about 80 mol % to about 90 mol % of the total lipid present in the particle.

In additional embodiments, the cationic lipid may comprise (at least) about 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, or 90 mol % (or any fraction thereof or range therein) of the total lipid present in the particle.

In the lipid particles of the invention (e.g., SNALP comprising an interfering RNA such as siRNA), the non-cationic lipid may comprise, e.g., one or more anionic lipids and/or neutral lipids. In preferred embodiments, the non-cationic lipid comprises one of the following neutral lipid components: (1) cholesterol or a derivative thereof; (2) a phospholipid; or (3) a mixture of a phospholipid and cholesterol or a derivative thereof.

Examples of cholesterol derivatives include, but are not limited to, cholestanol, cholestanone, cholestenone, coprostanol, cholesteryl-2'-hydroxyethyl ether, cholesteryl-4'-hydroxybutyl ether, and mixtures thereof. The synthesis of cholesteryl-2'-hydroxyethyl ether is described herein.

The phospholipid may be a neutral lipid including, but not limited to, dipalmitoylphosphatidylcholine (DPPC), distearoylphosphatidylcholine (DSPC), dioleoylphosphatidylethanolamine (DOPE), palmitoyloleoyl-phosphatidylcholine (POPC), palmitoyloleoyl-phosphatidylethanolamine (POPE), palmitoyloleyol-phosphatidylglycerol (POPG), dipalmitoyl-phosphatidylethanolamine (DPPE), dimyristoyl-phosphatidylethanolamine (DMPE), distearoyl-phosphatidylethanolamine (DSPE), monomethyl-phosphatidylethanolamine, dimethyl-phosphatidylethanolamine, dielaidoyl-phosphatidylethanolamine (DEPE), stearoyloleoyl-phosphatidylethanolamine (SOPE), egg phosphatidylcholine (EPC), and mixtures thereof. In certain preferred embodiments, the phospholipid is DPPC, DSPC, or mixtures thereof.

In some embodiments, the non-cationic lipid (e.g., one or more phospholipids and/or cholesterol) may comprise from about 10 mol % to about 60 mol %, from about 15 mol % to about 60 mol %, from about 20 mol % to about 60 mol %, from about 25 mol % to about 60 mol %, from about 30 mol % to about 60 mol %, from about 10 mol % to about 55 mol %, from about 15 mol % to about 55 mol %, from about 20 mol % to about 55 mol %, from about 25 mol % to about 55 mol %, from about 30 mol % to about 55 mol %, from about 13 mol % to about 50 mol %, from about 15 mol % to about 50 mol % or from about 20 mol % to about 50 mol % of the total lipid present in the particle. When the non-cationic lipid is a mixture of a phospholipid and cholesterol or a cholesterol derivative, the mixture may comprise up to about 40, 50, or 60 mol % of the total lipid present in the particle.

In other embodiments, the non-cationic lipid (e.g., one or more phospholipids and/or cholesterol) may comprise from about 10 mol % to about 49.5 mol %, from about 13 mol % to about 49.5 mol %, from about 15 mol % to about 49.5 mol %, from about 20 mol % to about 49.5 mol %, from about 25 mol % to about 49.5 mol %, from about 30 mol % to about 49.5 mol %, from about 35 mol % to about 49.5 mol %, or from about 40 mol % to about 49.5 mol % of the total lipid present in the particle.

In yet other embodiments, the non-cationic lipid (e.g., one or more phospholipids and/or cholesterol) may comprise from about 10 mol % to about 45 mol %, from about 13 mol % to about 45 mol %, from about 15 mol % to about 45 mol %, from about 20 mol % to about 45 mol %, from about 25 mol % to about 45 mol %, from about 30 mol % to about 45 mol %, or from about 35 mol % to about 45 mol % of the total lipid present in the particle.

In still yet other embodiments, the non-cationic lipid (e.g., one or more phospholipids and/or cholesterol) may comprise from about 10 mol % to about 40 mol %, from about 13 mol % to about 40 mol %, from about 15 mol % to about 40 mol %, from about 20 mol % to about 40 mol %, from about 25 mol % to about 40 mol %, or from about 30 mol % to about 40 mol % of the total lipid present in the particle.

In further embodiments, the non-cationic lipid (e.g., one or more phospholipids and/or cholesterol) may comprise from about 10 mol % to about 35 mol %, from about 13 mol % to about 35 mol %, from about 15 mol % to about 35 mol %, from about 20 mol % to about 35 mol %, or from about 25 mol % to about 35 mol % of the total lipid present in the particle.

In yet further embodiments, the non-cationic lipid (e.g., one or more phospholipids and/or cholesterol) may comprise from about 10 mol % to about 30 mol %, from about 13 mol % to about 30 mol %, from about 15 mol % to about 30 mol %, from about 20 mol % to about 30 mol %, from about 10 mol % to about 25 mol %, from about 13 mol % to about 25 mol %, or from about 15 mol % to about 25 mol % of the total lipid present in the particle.

In additional embodiments, the non-cationic lipid (e.g., one or more phospholipids and/or cholesterol) may comprise (at least) about 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, or 60 mol % (or any fraction thereof or range therein) of the total lipid present in the particle.

In certain preferred embodiments, the non-cationic lipid comprises cholesterol or a derivative thereof of from about 31.5 mol % to about 42.5 mol % of the total lipid present in the particle. As a non-limiting example, a phospholipid-free lipid particle of the invention may comprise cholesterol or a derivative thereof at about 37 mol % of the total lipid present in the particle. In other preferred embodiments, a phospholipid-free lipid particle of the invention may comprise cholesterol or a derivative thereof of from about 30 mol % to about 45 mol %, from about 30 mol % to about 40 mol %, from about 30 mol % to about 35 mol %, from about 35 mol % to about 45 mol %, from about 40 mol % to about 45 mol %, from about 32 mol % to about 45 mol %, from about 32 mol % to about 42 mol %, from about 32 mol % to about 40 mol %, from about 34 mol % to about 45 mol %, from about 34 mol % to about 42 mol %, from about 34 mol % to about 40 mol %, or about 30, 31, 32, 33, 34, 35, 36, 37, 38, 39, 40, 41, 42, 43, 44, or 45 mol % (or any fraction thereof or range therein) of the total lipid present in the particle.

In certain other preferred embodiments, the non-cationic lipid comprises a mixture of: (i) a phospholipid of from about 4 mol % to about 10 mol % of the total lipid present in the particle; and (ii) cholesterol or a derivative thereof of from about 30 mol % to about 40 mol % of the total lipid present in the particle. As a non-limiting example, a lipid particle comprising a mixture of a phospholipid and cholesterol may comprise DPPC at about 7 mol % and cholesterol at about 34 mol % of the total lipid present in the particle. In other embodiments, the non-cationic lipid comprises a mixture of: (i) a phospholipid of from about 3 mol % to about 15 mol %, from about 4 mol % to about 15 mol %, from about 4 mol % to about 12 mol %, from about 4 mol % to about 10 mol %, from about 4 mol % to about 8 mol %, from about 5 mol % to about 12 mol %, from about 5 mol % to about 9 mol %, from about 6 mol % to about 12 mol %, from about 6 mol % to about 10 mol %, or about 3, 4, 5, 6, 7, 8, 9, 10, 11, 12, 13, 14, or 15 mol % (or any fraction thereof or range therein) of the total lipid present in the particle; and (ii) cholesterol or a derivative thereof of from about 25 mol % to about 45 mol %, from about 30 mol % to about 45 mol %, from about 25 mol % to about 40 mol %, from about 30 mol % to about 40 mol %, from about 25 mol % to about 35 mol %, from about 30 mol % to about 35 mol %, from about 35 mol % to about 45 mol %, from about 40 mol % to about 45 mol %, from about 28 mol % to about 40 mol %, from about 28 mol % to about 38 mol %, from about 30 mol % to about 38 mol %, from about 32 mol % to about 36 mol %, or about 25, 26, 27, 28, 29, 30, 31, 32, 33, 34, 35, 36, 37, 38, 39, 40, 41, 42, 43, 44, or 45 mol % (or any fraction thereof or range therein) of the total lipid present in the particle.

In further preferred embodiments, the non-cationic lipid comprises a mixture of: (i) a phospholipid of from about 10 mol % to about 30 mol % of the total lipid present in the particle; and (ii) cholesterol or a derivative thereof of from about 10 mol % to about 30 mol % of the total lipid present in the particle. As a non-limiting example, a lipid particle comprising a mixture of a phospholipid and cholesterol may comprise DPPC at about 20 mol % and cholesterol at about 20 mol % of the total lipid present in the particle. In other embodiments, the non-cationic lipid comprises a mixture of: (i) a phospholipid of from about 10 mol % to about 30 mol %, from about 10 mol % to about 25 mol %, from about 10 mol % to about 20 mol %, from about 15 mol % to about 30 mol %, from about 20 mol % to about 30 mol %, from about 15 mol % to about 25 mol %, from about 12 mol % to about 28 mol %, from about 14 mol % to about 26 mol %, or about 10, 11, 12, 13, 14, 15, 16, 17, 18, 19, 20, 21, 22, 23, 24, 25, 26, 27, 28, 29, or 30 mol % (or any fraction thereof or range therein) of the total lipid present in the particle; and (ii) cholesterol or a derivative thereof of from about 10 mol % to about 30 mol %, from about 10 mol % to about 25 mol %, from about 10 mol % to about 20 mol %, from about 15 mol % to about 30 mol %, from about 20 mol % to about 30 mol %, from about 15 mol % to about 25 mol %, from about 12 mol % to about 28 mol %, from about 14 mol % to about 26 mol %, or about 10, 11, 12, 13, 14, 15, 16, 17, 18, 19, 20, 21, 22, 23, 24, 25, 26, 27, 28, 29, or 30 mol % (or any fraction thereof or range therein) of the total lipid present in the particle.

In the lipid particles of the invention (e.g., SNALP comprising an interfering RNA such as siRNA), the conjugated lipid that inhibits aggregation of particles may comprise, e.g., one or more of the following: a polyethyleneglycol (PEG)-lipid conjugate, a polyamide (ATTA)-lipid conjugate, a cationic-polymer-lipid conjugates (CPLs), or mixtures thereof. In one preferred embodiment, the nucleic acid-lipid particles comprise either a PEG-lipid conjugate or an ATTA-lipid conjugate. In certain embodiments, the PEG-lipid conjugate or ATTA-lipid conjugate is used together with a CPL. The conjugated lipid that inhibits aggregation of particles may comprise a PEG-lipid including, e.g., a PEG-diacylglycerol (DAG), a PEG dialkyloxypropyl (DAA), a PEG-phospholipid, a PEG-ceramide (Cer), or mixtures thereof. The PEG-DAA conjugate may be PEG-dilauryloxypropyl (C12), a PEG-dimyristyloxypropyl (C14), a PEG-dipalmityloxypropyl (C16), a PEG-distearyloxypropyl (C18), or mixtures thereof.

Additional PEG-lipid conjugates suitable for use in the invention include, but are not limited to, mPEG2000-1,2-di-O-alkyl-sn3-carbomoylglyceride (PEG-C-DOMG). The synthesis of PEG-C-DOMG is described in PCT Application No. PCT/US08/88676, filed Dec. 31, 2008, the disclosure of which is herein incorporated by reference in its entirety for all purposes. Yet additional PEG-lipid conjugates suitable for use in the invention include, without limitation, 1-[8'-(1,2-dimyristoyl-3-propanoxy)-carboxamido-3',6'-dioxaoctanyl] carbamoyl-ω-methyl-poly(ethylene glycol) (2 KPEG-DMG). The synthesis of 2 KPEG-DMG is described in U.S. Pat. No. 7,404,969, the disclosure of which is herein incorporated by reference in its entirety for all purposes.

The PEG moiety of the PEG-lipid conjugates described herein may comprise an average molecular weight ranging from about 550 daltons to about 10,000 daltons. In certain instances, the PEG moiety has an average molecular weight of from about 750 daltons to about 5,000 daltons (e.g., from about 1,000 daltons to about 5,000 daltons, from about 1,500 daltons to about 3,000 daltons, from about 750 daltons to about 3,000 daltons, from about 750 daltons to about 2,000 daltons, etc.). In preferred embodiments, the PEG moiety has an average molecular weight of about 2,000 daltons or about 750 daltons.

In some embodiments, the conjugated lipid that inhibits aggregation of particles is a CPL that has the formula: A-W-Y, wherein A is a lipid moiety, W is a hydrophilic polymer, and Y is a polycationic moiety. W may be a polymer selected from the group consisting of polyethyleneglycol (PEG), polyamide, polylactic acid, polyglycolic acid, polylactic acid/polyglycolic acid copolymers, or combinations thereof, the polymer having a molecular weight of from about 250 to about 7000 daltons. In some embodiments, Y has at least 4 positive charges at a selected pH. In some embodiments, Y may be lysine, arginine, asparagine, glutamine, derivatives thereof, or combinations thereof.

In certain instances, the conjugated lipid that inhibits aggregation of particles (e.g., PEG-lipid conjugate) may comprise from about 0.1 mol % to about 2 mol %, from about 0.5 mol % to about 2 mol %, from about 1 mol % to about 2 mol %, from about 0.6 mol % to about 1.9 mol %, from about 0.7 mol % to about 1.8 mol %, from about 0.8 mol % to about 1.7 mol %, from about 1 mol % to about 1.8 mol %, from about 1.2 mol % to about 1.8 mol %, from about 1.2 mol % to about 1.7 mol %, from about 1.3 mol % to about 1.6 mol %, from about 1.4 mol % to about 1.5 mol %, or about 1, 1.1, 1.2, 1.3, 1.4, 1.5, 1.6, 1.7, 1.8, 1.9, or 2 mol % (or any fraction thereof or range therein) of the total lipid present in the particle.

In the lipid particles of the invention, the active agent or therapeutic agent may be fully encapsulated within the lipid portion of the particle, thereby protecting the active agent or therapeutic agent from enzymatic degradation. In preferred embodiments, a SNALP comprising a nucleic acid such as an interfering RNA (e.g., siRNA) is fully encapsulated within the lipid portion of the particle, thereby protecting the nucleic acid from nuclease degradation. In certain instances, the nucleic acid in the SNALP is not substantially degraded after exposure of the particle to a nuclease at 37° C. for at least about 20, 30, 45, or 60 minutes. In certain other instances, the nucleic acid in the SNALP is not substantially degraded after incubation of the particle in serum at 37° C. for at least about 30, 45, or 60 minutes or at least about 2, 3, 4, 5, 6, 7, 8, 9, 10, 12, 14, 16, 18, 20, 22, 24, 26, 28, 30, 32, 34, or 36 hours. In other embodiments, the active agent or therapeutic agent (e.g., nucleic acid such as siRNA) is complexed with the lipid portion of the particle. One of the benefits of the formulations of the present invention is that the lipid particle compositions are substantially non-toxic to mammals such as humans.

The term "fully encapsulated" indicates that the active agent or therapeutic agent in the lipid particle is not significantly degraded after exposure to serum or a nuclease or protease assay that would significantly degrade free DNA, RNA, or protein. In a fully encapsulated system, preferably less than about 25% of the active agent or therapeutic agent in the particle is degraded in a treatment that would normally degrade 100% of free active agent or therapeutic agent, more preferably less than about 10%, and most preferably less than about 5% of the active agent or therapeutic agent in the particle is degraded. In the context of nucleic acid therapeutic agents, full encapsulation may be determined by an Oligreen® assay. Oligreen® is an ultra-sensitive fluorescent nucleic acid stain for quantitating oligonucleotides and single-stranded DNA or RNA in solution (available from Invitrogen Corporation; Carlsbad, Calif.). "Fully encapsulated" also indicates that the lipid particles are serum-stable, that is, that they do not rapidly decompose into their component parts upon in vivo administration.

In another aspect, the present invention provides a lipid particle (e.g., SNALP) composition comprising a plurality of lipid particles. In preferred embodiments, the active agent or therapeutic agent (e.g., nucleic acid) is fully encapsulated within the lipid portion of the lipid particles (e.g., SNALP), such that from about 30% to about 100%, from about 40% to about 100%, from about 50% to about 100%, from about 60% to about 100%, from about 70% to about 100%, from about 80% to about 100%, from about 90% to about 100%, from about 30% to about 95%, from about 40% to about 95%, from about 50% to about 95%, from about 60% to about 95%, %, from about 70% to about 95%, from about 80% to about 95%, from about 85% to about 95%, from about 90% to about 95%, from about 30% to about 90%, from about 40% to about 90%, from about 50% to about 90%, from about 60% to about 90%, from about 70% to about 90%, from about 80% to about 90%, or at least about 30%, 35%, 40%, 45%, 50%, 55%, 60%, 65%, 70%, 75%, 80%, 85%, 90%, 91%, 92%, 93%, 94%, 95%, 96%, 97%, 98%, or 99% (or any fraction thereof or range therein) of the lipid particles (e.g., SNALP) have the active agent or therapeutic agent encapsulated therein.

Typically, the lipid particles (e.g., SNALP) of the invention have a lipid:active agent (e.g., lipid:nucleic acid) ratio (mass/mass ratio) of from about 1 to about 100. In some instances, the lipid:active agent (e.g., lipid:nucleic acid) ratio (mass/mass ratio) ranges from about 1 to about 50, from about 2 to about 25, from about 3 to about 20, from about 4 to about 15, or from about 5 to about 10. In preferred embodiments, the lipid particles of the invention have a lipid:active agent (e.g., lipid:nucleic acid) ratio (mass/mass ratio) of from about 5 to about 15, e.g., about 5, 6, 7, 8, 9, 10, 11, 12, 13, 14, or 15 (or any fraction thereof or range therein).

Typically, the lipid particles (e.g., SNALP) of the invention have a mean diameter of from about 40 nm to about 150 nm. In preferred embodiments, the lipid particles (e.g., SNALP) of the invention have a mean diameter of from about 40 nm to about 130 nm, from about 40 nm to about 120 nm, from about 40 nm to about 100 nm, from about 50 nm to about 120 nm, from about 50 nm to about 100 nm, from about 60 nm to about 120 nm, from about 60 nm to about 110 nm, from about 60 nm to about 100 nm, from about 60 nm to about 90 nm, from about 60 nm to about 80 nm, from about 70 nm to about 120 nm, from about 70 nm to about 110 nm, from about 70 nm to about 100 nm, from about 70 nm to about 90 nm, from about 70 nm to about 80 nm, or less than about 120 nm, 110 nm, 100 nm, 90 nm, or 80 nm (or any fraction thereof or range therein).

In one specific embodiment of the invention, the SNALP comprises: (a) one or more unmodified and/or modified interfering RNA (e.g., siRNA, aiRNA, miRNA) that silence target gene expression; (b) a cationic lipid comprising from about 56.5 mol % to about 66.5 mol % of the total lipid present in the particle; (c) a non-cationic lipid comprising from about 31.5 mol % to about 42.5 mol % of the total lipid present in the particle; and (d) a conjugated lipid that inhibits aggregation of particles comprising from about 1 mol % to about 2 mol % of the total lipid present in the particle. This specific embodiment of SNALP is generally referred to herein as the "1:62" formulation. In a preferred embodiment, the cationic lipid is DLinDMA or DLin-K-C2-DMA ("XTC2"), the non-cationic lipid is cholesterol, and the conjugated lipid is a PEG-DAA conjugate. Although these are preferred embodiments of the 1:62 formulation, those of skill in the art will appreciate that other cationic lipids, non-cationic lipids (including other cholesterol derivatives), and conjugated lipids can be used in the 1:62 formulation as described herein.

In another specific embodiment of the invention, the SNALP comprises: (a) one or more unmodified and/or modified interfering RNA (e.g., siRNA, aiRNA, miRNA) that silence target gene expression; (b) a cationic lipid comprising from about 52 mol % to about 62 mol % of the total lipid present in the particle; (c) a non-cationic lipid comprising from about 36 mol % to about 47 mol % of the total lipid present in the particle; and (d) a conjugated lipid that inhibits aggregation of particles comprising from about 1 mol % to about 2 mol % of the total lipid present in the particle. This specific embodiment of SNALP is generally referred to herein as the "1:57" formulation. In one preferred embodiment, the cationic lipid is DLinDMA or DLin-K-C2-DMA ("XTC2"), the non-cationic lipid is a mixture of a phospholipid (such as DPPC) and cholesterol, wherein the phospholipid comprises from about 5 mol % to about 9 mol % of the total lipid present in the particle (e.g., about 7.1 mol %) and the cholesterol (or cholesterol derivative) comprises from about 32 mol % to about 37 mol % of the total lipid present in the particle (e.g., about 34.3 mol %), and the PEG-lipid is a PEG-DAA (e.g., PEG-cDMA). In another preferred embodiment, the cationic lipid is DLinDMA or DLin-K-C2-DMA ("XTC2"), the non-cationic lipid is a mixture of a phospholipid (such as DPPC) and cholesterol, wherein the phospholipid comprises from about 15 mol % to about 25 mol % of the total lipid present in the particle (e.g., about 20 mol %) and the cholesterol (or cholesterol derivative) comprises from about 15 mol % to about 25 mol % of the total lipid present in the particle (e.g., about 20 mol %), and the PEG-lipid is a PEG-DAA (e.g., PEG-cDMA). Although these are preferred embodiments of the 1:57 formulation, those of skill in the art will appreciate that other cationic lipids, non-cationic lipids (including other phospholipids and other cholesterol derivatives), and conjugated lipids can be used in the 1:57 formulation as described herein.

In preferred embodiments, the 1:62 SNALP formulation is a three-component system which is phospholipid-free and comprises about 1.5 mol % PEG-cDMA (or PEG-cDSA), about 61.5 mol % DLinDMA (or XTC2), and about 36.9 mol % cholesterol (or derivative thereof). In other preferred embodiments, the 1:57 SNALP formulation is a four-component system which comprises about 1.4 mol % PEG-cDMA (or PEG-cDSA), about 57.1 mol % DLinDMA (or XTC2), about 7.1 mol % DPPC, and about 34.3 mol % cholesterol (or derivative thereof). In yet other preferred embodiments, the 1:57 SNALP formulation is a four-component system which comprises about 1.4 mol % PEG-cDMA (or PEG-cDSA), about 57.1 mol % DLinDMA (or XTC2), about 20 mol % DPPC, and about 20 mol % cholesterol (or derivative thereof). It should be understood that these SNALP formulations are target formulations, and that the amount of lipid (both cationic and non-cationic) present and the amount of lipid conjugate present in the SNALP formulations may vary.

The present invention also provides a pharmaceutical composition comprising a lipid particle (e.g., SNALP) described herein and a pharmaceutically acceptable carrier.

In a further aspect, the present invention provides a method for introducing one or more active agents or therapeutic agents (e.g., nucleic acid) into a cell, comprising contacting the cell with a lipid particle (e.g., SNALP) described herein. In one embodiment, the cell is in a mammal and the mammal is a human. In another embodiment, the present invention provides a method for the in vivo delivery of one or more active agents or therapeutic agents (e.g., nucleic acid), comprising administering to a mammalian subject a lipid particle (e.g., SNALP) described herein. In a preferred embodiment, the mode of administration includes, but is not limited to, oral, intranasal, intravenous, intraperitoneal, intramuscular, intra-articular, intralesional, intratracheal, subcutaneous, and intradermal. Preferably, the mammalian subject is a human.

In one embodiment, at least about 5%, 10%, 15%, 20%, or 25% of the total injected dose of the lipid particles (e.g., SNALP) is present in plasma about 8, 12, 24, 36, or 48 hours after injection. In other embodiments, more than about 20%, 30%, 40% and as much as about 60%, 70% or 80% of the total injected dose of the lipid particles (e.g., SNALP) is present in plasma about 8, 12, 24, 36, or 48 hours after injection. In certain instances, more than about 10% of a plurality of the particles is present in the plasma of a mammal about 1 hour after administration. In certain other instances, the presence of the lipid particles (e.g., SNALP) is detectable at least about 1 hour after administration of the particle. In certain embodiments, the presence of an active agent or therapeutic agent such as an interfering RNA (e.g., siRNA) is detectable in cells of the lung, liver, tumor, or at a site of inflammation at about 8, 12, 24, 36, 48, 60, 72 or 96 hours after administration. In other embodiments, downregulation of expression of a target sequence by an active agent or therapeutic agent such as an interfering RNA (e.g., siRNA) is detectable at about 8, 12, 24, 36, 48, 60, 72 or 96 hours after administration. In yet other embodiments, downregulation of expression of a target sequence by an active agent or therapeutic agent such as an interfering RNA (e.g., siRNA) occurs preferentially in tumor cells or in cells at a site of inflammation. In further embodiments, the presence or effect of an active agent or therapeutic agent such as an interfering RNA (e.g., siRNA) in cells at a site proximal or distal to the site of administration or in cells of the lung, liver, or a tumor is detectable at about 12, 24, 48, 72, or 96 hours, or at about 6, 8, 10, 12, 14, 16, 18, 19, 20, 22, 24, 26, or 28 days after administration. In additional embodiments, the lipid particles (e.g., SNALP) of the invention are administered parenterally or intraperitoneally.

In some embodiments, the lipid particles (e.g., SNALP) of the invention are particularly useful in methods for the therapeutic delivery of one or more nucleic acids comprising an interfering RNA sequence (e.g., siRNA). In particular, it is an object of this invention to provide in vitro and in vivo methods for treatment of a disease or disorder in a mammal (e.g., a rodent such as a mouse or a primate such as a human, chimpanzee, or monkey) by downregulating or silencing the transcription and/or translation of one or more target nucleic acid sequences or genes of interest. As a non-limiting example, the methods of the invention are useful for in vivo delivery of interfering RNA (e.g., siRNA) to the liver and/or tumor of a mammalian subject. In certain embodiments, the disease or disorder is associated with expression and/or overexpression of a gene and expression or overexpression of the gene is reduced by the interfering RNA (e.g., siRNA). In certain other embodiments, a therapeutically effective amount of the lipid particle (e.g., SNALP) may be administered to the mammal. In some instances, an interfering RNA (e.g., siRNA) is formulated into a SNALP, and the particles are administered to patients requiring such treatment. In other instances, cells are removed from a patient, the interfering RNA (e.g., siRNA) is delivered in vitro (e.g., using a SNALP described herein), and the cells are reinjected into the patient.

In an additional aspect, the present invention provides lipid particles (e.g., SNALP) comprising asymmetrical interfering RNA (aiRNA) molecules that silence the expression of a target gene and methods of using such particles to silence target gene expression.

In one embodiment, the aiRNA molecule comprises a double-stranded (duplex) region of about 10 to about 25 (base paired) nucleotides in length, wherein the aiRNA molecule comprises an antisense strand comprising 5' and 3' overhangs, and wherein the aiRNA molecule is capable of silencing target gene expression.

In certain instances, the aiRNA molecule comprises a double-stranded (duplex) region of about 12-20, 12-19, 12-18, 13-17, or 14-17 (base paired) nucleotides in length, more typically 12, 13, 14, 15, 16, 17, 18, 19, or 20 (base paired) nucleotides in length. In certain other instances, the 5' and 3' overhangs on the antisense strand comprise sequences that are complementary to the target RNA sequence, and may optionally further comprise nontargeting sequences. In some embodiments, each of the 5' and 3' overhangs on the antisense strand comprises or consists of one, two, three, four, five, six, seven, or more nucleotides.

In other embodiments, the aiRNA molecule comprises modified nucleotides selected from the group consisting of 2'OMe nucleotides, 2'F nucleotides, 2'-deoxy nucleotides, 2'-O-MOE nucleotides, LNA nucleotides, and mixtures thereof. In a preferred embodiment, the aiRNA molecule comprises 2'OMe nucleotides. As a non-limiting example, the 2'OMe nucleotides may be selected from the group consisting of 2'OMe-guanosine nucleotides, 2'OMe-uridine nucleotides, and mixtures thereof.

In a related aspect, the present invention provides lipid particles (e.g., SNALP) comprising microRNA (miRNA) molecules that silence the expression of a target gene and methods of using such compositions to silence target gene expression.

In one embodiment, the miRNA molecule comprises about 15 to about 60 nucleotides in length, wherein the miRNA molecule is capable of silencing target gene expression.

In certain instances, the miRNA molecule comprises about 15-50, 15-40, or 15-30 nucleotides in length, more typically about 15-25 or 19-25 nucleotides in length, and are preferably about 20-24, 21-22, or 21-23 nucleotides in length. In a preferred embodiment, the miRNA molecule is a mature miRNA molecule targeting an RNA sequence of interest.

In some embodiments, the miRNA molecule comprises modified nucleotides selected from the group consisting of 2'OMe nucleotides, 2'F nucleotides, 2'-deoxy nucleotides, 2'-O-MOE nucleotides, LNA nucleotides, and mixtures thereof. In a preferred embodiment, the miRNA molecule comprises 2'OMe nucleotides. As a non-limiting example, the 2'OMe nucleotides may be selected from the group consisting of 2'OMe-guanosine nucleotides, 2'OMe-uridine nucleotides, and mixtures thereof.

As such, the lipid particles of the invention (e.g., SNALP) are advantageous and suitable for use in the administration of active agents or therapeutic agents such as nucleic acid (e.g., interfering RNA such as siRNA, aiRNA, and/or miRNA) to a subject (e.g., a mammal such as a human) because they are stable in circulation, of a size required for pharmacodynamic behavior resulting in access to extravascular sites, and are capable of reaching target cell populations.

IV. Active Agents

Active agents (e.g., therapeutic agents) include any molecule or compound capable of exerting a desired effect on a cell, tissue, organ, or subject. Such effects may be, e.g., biological, physiological, and/or cosmetic. Active agents may be any type of molecule or compound including, but not limited to, nucleic acids, peptides, polypeptides, small molecules, and mixtures thereof. Non-limiting examples of nucleic acids include interfering RNA molecules (e.g., siRNA, aiRNA, miRNA), antisense oligonucleotides, plasmids, ribozymes, immunostimulatory oligonucleotides, and mixtures thereof. Examples of peptides or polypeptides include, without limitation, antibodies (e.g., polyclonal antibodies, monoclonal antibodies, antibody fragments; humanized antibodies, recombinant antibodies, recombinant human antibodies, Primatized™ antibodies), cytokines, growth factors, apoptotic factors, differentiation-inducing factors, cell-surface receptors and their ligands, hormones, and mixtures thereof. Examples of small molecules include, but are not limited to, small organic molecules or compounds such as any conventional agent or drug known to those of skill in the art.

In some embodiments, the active agent is a therapeutic agent, or a salt or derivative thereof. Therapeutic agent derivatives may be therapeutically active themselves or they may be prodrugs, which become active upon further modification. Thus, in one embodiment, a therapeutic agent derivative retains some or all of the therapeutic activity as compared to the unmodified agent, while in another embodiment, a therapeutic agent derivative is a prodrug that lacks therapeutic activity, but becomes active upon further modification.

A. Nucleic Acids

In certain embodiments, lipid particles of the present invention are associated with a nucleic acid, resulting in a nucleic acid-lipid particle (e.g., SNALP). In some embodiments, the nucleic acid is fully encapsulated in the lipid particle. As used herein, the term "nucleic acid" includes any oligonucleotide or polynucleotide, with fragments containing up to 60 nucleotides generally termed oligonucleotides, and longer fragments termed polynucleotides. In particular embodiments, oligonucleotides of the invention are from about 15 to about 60 nucleotides in length. Nucleic acid may be administered alone in the lipid particles of the invention, or in combination (e.g., co-administered) with lipid particles of the invention comprising peptides, polypeptides, or small molecules such as conventional drugs.

In the context of this invention, the terms "polynucleotide" and "oligonucleotide" refer to a polymer or oligomer of nucleotide or nucleoside monomers consisting of naturally-occurring bases, sugars and intersugar (backbone) linkages. The terms "polynucleotide" and "oligonucleotide" also include polymers or oligomers comprising non-naturally occurring monomers, or portions thereof, which function similarly. Such modified or substituted oligonucleotides are often preferred over native forms because of properties such as, for example, enhanced cellular uptake, reduced immunogenicity, and increased stability in the presence of nucleases.

Oligonucleotides are generally classified as deoxyribooligonucleotides or ribooligonucleotides. A deoxyribooligonucleotide consists of a 5-carbon sugar called deoxyribose joined covalently to phosphate at the 5' and 3' carbons of this sugar to form an alternating, unbranched polymer. A ribooligonucleotide consists of a similar repeating structure where the 5-carbon sugar is ribose.

The nucleic acid that is present in a lipid-nucleic acid particle according to this invention includes any form of nucleic acid that is known. The nucleic acids used herein can be single-stranded DNA or RNA, or double-stranded DNA or RNA, or DNA-RNA hybrids. Examples of double-stranded DNA are described herein and include, e.g., structural genes, genes including control and termination regions, and self-replicating systems such as viral or plasmid DNA. Examples of double-stranded RNA are described herein and include, e.g., siRNA and other RNAi agents such as aiRNA and pre-miRNA. Single-stranded nucleic acids include, e.g., antisense oligonucleotides, ribozymes, mature miRNA, and triplex-forming oligonucleotides.

Nucleic acids of the invention may be of various lengths, generally dependent upon the particular form of nucleic acid. For example, in particular embodiments, plasmids or genes may be from about 1,000 to about 100,000 nucleotide residues in length. In particular embodiments, oligonucleotides may range from about 10 to about 100 nucleotides in length. In various related embodiments, oligonucleotides, both single-stranded, double-stranded, and triple-stranded, may range in length from about 10 to about 60 nucleotides, from about 15 to about 60 nucleotides, from about 20 to about 50 nucleotides, from about 15 to about 30 nucleotides, or from about 20 to about 30 nucleotides in length.

In particular embodiments, an oligonucleotide (or a strand thereof) of the invention specifically hybridizes to or is complementary to a target polynucleotide sequence. The terms "specifically hybridizable" and "complementary" as used herein indicate a sufficient degree of complementarity such that stable and specific binding occurs between the DNA or RNA target and the oligonucleotide. It is understood that an oligonucleotide need not be 100% complementary to its target nucleic acid sequence to be specifically hybridizable. In preferred embodiments, an oligonucleotide is specifically hybridizable when binding of the oligonucleotide to the target sequence interferes with the normal function of the target sequence to cause a loss of utility or expression therefrom, and there is a sufficient degree of complementarity to avoid non-specific binding of the oligonucleotide to non-target sequences under conditions in which specific binding is desired, i.e., under physiological conditions in the case of in vivo assays or therapeutic treatment, or, in the case of in vitro assays, under conditions in which the assays are conducted. Thus, the oligonucleotide may include 1, 2, 3, or more base substitutions as compared to the region of a gene or mRNA sequence that it is targeting or to which it specifically hybridizes.

1. siRNA

The siRNA component of the nucleic acid-lipid particles of the present invention is capable of silencing the expression of a target gene of interest. Each strand of the siRNA duplex is typically about 15 to about 60 nucleotides in length, preferably about 15 to about 30 nucleotides in length. In certain embodiments, the siRNA comprises at least one modified nucleotide. The modified siRNA is generally less immunostimulatory than a corresponding unmodified siRNA sequence and retains RNAi activity against the target gene of interest. In some embodiments, the modified siRNA contains at least one 2'OMe purine or pyrimidine nucleotide such as a 2'OMe-guanosine, 2'OMe-uridine, 2'OMe-adenosine, and/or 2'OMe-cytosine nucleotide. In preferred embodiments, one or more of the uridine and/or guanosine nucleotides are modified. The modified nucleotides can be present in one strand (i.e., sense or antisense) or both strands of the siRNA. The siRNA sequences may have overhangs (e.g., 3' or 5' overhangs as described in Elbashir et al., *Genes Dev.*, 15:188 (2001) or Nykanen et al., *Cell*, 107:309 (2001)), or may lack overhangs (i.e., have blunt ends).

The modified siRNA generally comprises from about 1% to about 100% (e.g., about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 35%, 40%, 45%, 50%, 55%, 60%, 65%, 70%, 75%, 80%, 85%, 90%, 95%, or 100%) modified nucleotides in the double-stranded region of the siRNA duplex. In certain embodiments, one, two, three, four, five, six, seven, eight, nine, ten, or more of the nucleotides in the double-stranded region of the siRNA comprise modified nucleotides.

In some embodiments, less than about 25% (e.g., less than about 25%, 24%, 23%, 22%, 21%, 20%, 19%, 18%, 17%, 16%, 15%, 14%, 13%, 12%, 11%, 10%, 9%, 8%, 7%, 6%, 5%, 4%, 3%, 2%, or 1%) of the nucleotides in the double-stranded region of the siRNA comprise modified nucleotides.

In other embodiments, from about 1% to about 25% (e.g., from about 1%-25%, 2%-25%, 3%-25%, 4%-25%, 5%-25%, 6%-25%, 7%-25%, 8%-25%, 9%-25%, 10%-25%, 11%-25%, 12%-25%, 13%-25%, 14%-25%, 15%-25%, 16%-25%, 17%-25%, 18%-25%, 19%-25%, 20%-25%, 21%-25%, 22%-25%, 23%-25%, 24%-25%, etc.) or from about 1% to about 20% (e.g., from about 1%-20%, 2%-20%, 3%-20%, 4%-20%, 5%-20%, 6%-20%, 7%-20%, 8%-20%, 9%-20%, 10%-20%, 11%-20%, 12%-20%, 13%-20%, 14%-20%, 15%-20%, 16%-20%, 17%-20%, 18%-20%, 19%-20%, 1%-19%, 2%-19%, 3%-19%, 4%-19%, 5%-19%, 6%-19%, 7%-19%, 8%-19%, 9%-19%, 10%-19%, 11%-19%, 12%-19%, 13%-19%, 14%-19%, 15%-19%, 16%-19%, 17%-19%, 18%-19%, 1%-18%, 2%-18%, 3%-18%, 4%-18%, 5%-18%, 6%-18%, 7%-18%, 8%-18%, 9%-18%, 10%-18%, 11%-18%, 12%-18%, 13%-18%, 14%-18%, 15%-18%, 16%-18%, 17%-18%, 1%-17%, 2%-17%, 3%-17%, 4%-17%, 5%-17%, 6%-17%, 7%-17%, 8%-17%, 9%-17%, 10%-17%, 11%-17%, 12%-17%, 13%-17%, 14%-17%, 15%-17%, 16%-17%, 1%-16%, 2%-16%, 3%-16%, 4%-16%, 5%-16%, 6%-16%, 7%-16%, 8%-16%, 9%-16%, 10%-16%, 11%-16%, 12%-16%, 13%-16%, 14%-16%, 15%-16%, 1%-15%, 2%-15%, 3%-15%, 4%-15%, 5%-15%, 6%-15%, 7%-15%, 8%-15%, 9%-15%, 10%-15%, 11%-15%, 12%-15%, 13%-15%, 14%-15%, etc.) of the nucleotides in the double-stranded region of the siRNA comprise modified nucleotides.

In further embodiments, e.g., when one or both strands of the siRNA are selectively modified at uridine and/or guanosine nucleotides, the resulting modified siRNA can comprise less than about 30% modified nucleotides (e.g., less than about 30%, 29%, 28%, 27%, 26%, 25%, 24%, 23%, 22%, 21%, 20%, 19%, 18%, 17%, 16%, 15%, 14%, 13%, 12%, 11%, 10%, 9%, 8%, 7%, 6%, 5%, 4%, 3%, 2%, or 1% modified nucleotides) or from about 1% to about 30% modified nucleotides (e.g., from about 1%-30%, 2%-30%, 3%-30%, 4%-30%, 5%-30%, 6%-30%, 7%-30%, 8%-30%, 9%-30%, 10%-30%, 11%-30%, 12%-30%, 13%-30%, 14%-30%, 15%-30%, 16%-30%, 17%-30%, 18%-30%, 19%-30%, 20%-30%, 21%-30%, 22%-30%, 23%-30%, 24%-30%, 25%-30%, 26%-30%, 27%-30%, 28%-30%, or 29%-30% modified nucleotides).

a. Selection of siRNA Sequences

Suitable siRNA sequences can be identified using any means known in the art. Typically, the methods described in Elbashir et al., *Nature*, 411:494-498 (2001) and Elbashir et al., *EMBO J.*, 20:6877-6888 (2001) are combined with rational design rules set forth in Reynolds et al., *Nature Biotech.*, 22(3):326-330 (2004).

Generally, the nucleotide sequence 3' of the AUG start codon of a transcript from the target gene of interest is scanned for dinucleotide sequences (e.g., AA, NA, CC, GG, or UU, wherein N=C, G, or U) (see, e.g., Elbashir et al., *EMBO J.*, 20:6877-6888 (2001)). The nucleotides immediately 3' to the dinucleotide sequences are identified as potential siRNA sequences (i.e., a target sequence or a sense strand sequence). Typically, the 19, 21, 23, 25, 27, 29, 31, 33, 35, or more nucleotides immediately 3' to the dinucleotide sequences are identified as potential siRNA sequences. In some embodiments, the dinucleotide sequence is an AA or NA sequence and the 19 nucleotides immediately 3' to the AA or NA dinucleotide are identified as potential siRNA sequences. siRNA sequences are usually spaced at different positions along the length of the target gene. To further enhance silencing efficiency of the siRNA sequences, potential siRNA sequences may be analyzed to identify sites that do not contain regions of homology to other coding sequences, e.g., in the target cell or organism. For example, a suitable siRNA sequence of about 21 base pairs typically will not have more than 16-17 contiguous base pairs of homology to coding sequences in the target cell or organism. If the siRNA sequences are to be expressed from an RNA Pol III promoter, siRNA sequences lacking more than 4 contiguous A's or T's are selected.

Once a potential siRNA sequence has been identified, a complementary sequence (i.e., an antisense strand sequence) can be designed. A potential siRNA sequence can also be analyzed using a variety of criteria known in the art. For example, to enhance their silencing efficiency, the siRNA sequences may be analyzed by a rational design algorithm to identify sequences that have one or more of the following features: (1) G/C content of about 25% to about 60% G/C; (2) at least 3 A/Us at positions 15-19 of the sense strand; (3) no internal repeats; (4) an A at position 19 of the sense strand; (5) an A at position 3 of the sense strand; (6) a U at position 10 of the sense strand; (7) no G/C at position 19 of the sense strand; and (8) no G at position 13 of the sense strand. siRNA design tools that incorporate algorithms that assign suitable values of each of these features and are useful for selection of siRNA can be found at, e.g., boz094.ust.hk/RNAi/siRNA. One of skill in the art will appreciate that sequences with one or more of the foregoing characteristics may be selected for further analysis and testing as potential siRNA sequences.

Additionally, potential siRNA sequences with one or more of the following criteria can often be eliminated as siRNA: (1) sequences comprising a stretch of 4 or more of the same base in a row; (2) sequences comprising homopolymers of Gs (i.e., to reduce possible non-specific effects due to structural characteristics of these polymers; (3) sequences comprising triple base motifs (e.g., GGG, CCC, AAA, or TTT); (4) sequences comprising stretches of 7 or more G/Cs in a row; and (5) sequences comprising direct repeats of 4 or more bases within the candidates resulting in internal fold-back structures. However, one of skill in the art will appreciate that sequences with one or more of the foregoing characteristics may still be selected for further analysis and testing as potential siRNA sequences.

In some embodiments, potential siRNA sequences may be further analyzed based on siRNA duplex asymmetry as described in, e.g., Khvorova et al., *Cell*, 115:209-216 (2003); and Schwarz et al., *Cell*, 115:199-208 (2003). In other embodiments, potential siRNA sequences may be further analyzed based on secondary structure at the target site as described in, e.g., Luo et al., *Biophys. Res. Commun.*, 318: 303-310 (2004). For example, secondary structure at the target site can be modeled using the Mfold algorithm (available at www.bioinfo.rpi.edu/applications/mfold/rna/form1.cgi) to select siRNA sequences which favor accessibility at the target site where less secondary structure in the form of base-pairing and stem-loops is present.

Once a potential siRNA sequence has been identified, the sequence can be analyzed for the presence of any immunostimulatory properties, e.g., using an in vitro cytokine assay or an in vivo animal model. Motifs in the sense and/or antisense strand of the siRNA sequence such as GU-rich motifs (e.g., 5'-GU-3',5'-UGU-3',5'-GUGU-3',5'-UGUGU-3', etc.) can also provide an indication of whether the sequence may be immunostimulatory. Once an siRNA molecule is found to be immunostimulatory, it can then be modified to decrease its immunostimulatory properties as described herein. As a non-limiting example, an siRNA sequence can be contacted with a mammalian responder cell under conditions such that the cell produces a detectable immune response to determine whether the siRNA is an immunostimulatory or a non-immunostimulatory siRNA. The mammalian responder cell may be from a naïve mammal (i.e., a mammal that has not previously been in contact with the gene product of the siRNA sequence). The mammalian responder cell may be, e.g., a peripheral blood mononuclear cell (PBMC), a macrophage, and the like. The detectable immune response may comprise production of a cytokine or growth factor such as, e.g., TNF-α, IFN-α, IFN-β, IFN-γ, IL-6, IL-12, or a combination thereof. An siRNA molecule identified as being immunostimulatory can then be modified to decrease its immunostimulatory properties by replacing at least one of the nucleotides on the sense and/or antisense strand with modified nucleotides. For example, less than about 30% (e.g., less than about 30%, 25%, 20%, 15%, 10%, or 5%) of the nucleotides in the double-stranded region of the siRNA duplex can be replaced with modified nucleotides such as 2'OMe nucleotides. The modified siRNA can then be contacted with a mammalian responder cell as described above to confirm that its immunostimulatory properties have been reduced or abrogated.

Suitable in vitro assays for detecting an immune response include, but are not limited to, the double monoclonal antibody sandwich immunoassay technique of David et al. (U.S. Pat. No. 4,376,110); monoclonal-polyclonal antibody sandwich assays (Wide et al., in Kirkham and Hunter, eds., *Radioimmunoassay Methods*, E. and S. Livingstone, Edinburgh (1970)); the "Western blot" method of Gordon et al. (U.S. Pat. No. 4,452,901); immunoprecipitation of labeled ligand (Brown et al., *J. Biol. Chem.*, 255:4980-4983 (1980)); enzyme-linked immunosorbent assays (ELISA) as described, for example, by Raines et al., *J. Biol. Chem.*, 257:5154-5160 (1982); immunocytochemical techniques, including the use of fluorochromes (Brooks et al., *Clin. Exp. Immunol.*, 39:477 (1980)); and neutralization of activity (Bowen-Pope et al., *Proc. Natl. Acad. Sci. USA*, 81:2396-2400 (1984)). In addition to the immunoassays described above, a number of other immunoassays are available, including those described in U.S. Pat. Nos. 3,817,827; 3,850,752; 3,901,654; 3,935,074; 3,984,533; 3,996,345; 4,034,074; and 4,098,876. The disclosures of these references are herein incorporated by reference in their entirety for all purposes.

A non-limiting example of an in vivo model for detecting an immune response includes an in vivo mouse cytokine induction assay as described in, e.g., Judge et al., *Mol. Ther.*, 13:494-505 (2006). In certain embodiments, the assay that can be performed as follows: (1) siRNA can be administered by standard intravenous injection in the lateral tail vein; (2) blood can be collected by cardiac puncture about 6 hours after administration and processed as plasma for cytokine analysis; and (3) cytokines can be quantified using sandwich ELISA kits according to the manufacturer's instructions (e.g., mouse and human IFN-α (PBL Biomedical; Piscataway, N.J.); human IL-6 and TNF-α (eBioscience; San Diego, Calif.); and mouse IL-6, TNF-α, and IFN-γ (BD Biosciences; San Diego, Calif.)).

Monoclonal antibodies that specifically bind cytokines and growth factors are commercially available from multiple sources and can be generated using methods known in the art (see, e.g., Kohler et al., *Nature*, 256: 495-497 (1975) and Harlow and Lane, ANTIBODIES, A LABORATORY MANUAL, Cold Spring Harbor Publication, New York (1999)). Generation of monoclonal antibodies has been previously described and can be accomplished by any means known in the art (Buhring et al., in Hybridoma, Vol. 10, No. 1, pp. 77-78 (1991)). In some methods, the monoclonal antibody is labeled (e.g., with any composition detectable by spectroscopic, photochemical, biochemical, electrical, optical, or chemical means) to facilitate detection.

b. Generating siRNA Molecules siRNA can be provided in several forms including, e.g., as one or more isolated small-interfering RNA (siRNA) duplexes, as longer double-stranded RNA (dsRNA), or as siRNA or dsRNA transcribed from a transcriptional cassette in a DNA plasmid. The siRNA sequences may have overhangs (e.g., 3' or 5' overhangs as described in Elbashir et al., *Genes Dev.*, 15:188 (2001) or Nykänen et al., *Cell*, 107:309 (2001), or may lack overhangs (i.e., to have blunt ends).

An RNA population can be used to provide long precursor RNAs, or long precursor RNAs that have substantial or complete identity to a selected target sequence can be used to make the siRNA. The RNAs can be isolated from cells or tissue, synthesized, and/or cloned according to methods well known to those of skill in the art. The RNA can be a mixed population (obtained from cells or tissue, transcribed from cDNA, subtracted, selected, etc.), or can represent a single target sequence. RNA can be naturally occurring (e.g., isolated from tissue or cell samples), synthesized in vitro (e.g., using T7 or SP6 polymerase and PCR products or a cloned cDNA), or chemically synthesized.

To form a long dsRNA, for synthetic RNAs, the complement is also transcribed in vitro and hybridized to form a dsRNA. If a naturally occurring RNA population is used, the RNA complements are also provided (e.g., to form dsRNA for digestion by *E. coli* RNAse III or Dicer), e.g., by transcribing cDNAs corresponding to the RNA population, or by using RNA polymerases. The precursor RNAs are then hybridized to form double stranded RNAs for digestion. The dsRNAs can be directly administered to a subject or can be digested in vitro prior to administration.

Methods for isolating RNA, synthesizing RNA, hybridizing nucleic acids, making and screening cDNA libraries, and performing PCR are well known in the art (see, e.g., Gubler and Hoffman, *Gene*, 25:263-269 (1983); Sambrook et al., supra; Ausubel et al., supra), as are PCR methods (see, U.S.

Pat. Nos. 4,683,195 and 4,683,202; *PCR Protocols: A Guide to Methods and Applications* (Innis et al., eds, 1990)). Expression libraries are also well known to those of skill in the art. Additional basic texts disclosing the general methods of use in this invention include Sambrook et al., *Molecular Cloning, A Laboratory Manual* (2nd ed. 1989); Kriegler, *Gene Transfer and Expression: A Laboratory Manual* (1990); and *Current Protocols in Molecular Biology* (Ausubel et al., eds., 1994). The disclosures of these references are herein incorporated by reference in their entirety for all purposes.

Preferably, siRNA are chemically synthesized. The oligonucleotides that comprise the siRNA molecules of the invention can be synthesized using any of a variety of techniques known in the art, such as those described in Usman et al., *J. Am. Chem. Soc.,* 109:7845 (1987); Scaringe et al., *Nucl. Acids Res.,* 18:5433 (1990); Wincott et al., *Nucl. Acids Res.,* 23:2677-2684 (1995); and Wincott et al., *Methods Mol. Bio.,* 74:59 (1997). The synthesis of oligonucleotides makes use of common nucleic acid protecting and coupling groups, such as dimethoxytrityl at the 5'-end and phosphoramidites at the 3'-end. As a non-limiting example, small scale syntheses can be conducted on an Applied Biosystems synthesizer using a 0.2 µmol scale protocol. Alternatively, syntheses at the 0.2 µmol scale can be performed on a 96-well plate synthesizer from Protogene (Palo Alto, Calif.). However, a larger or smaller scale of synthesis is also within the scope of this invention. Suitable reagents for oligonucleotide synthesis, methods for RNA deprotection, and methods for RNA purification are known to those of skill in the art.

siRNA molecules can also be synthesized via a tandem synthesis technique, wherein both strands are synthesized as a single continuous oligonucleotide fragment or strand separated by a cleavable linker that is subsequently cleaved to provide separate fragments or strands that hybridize to form the siRNA duplex. The linker can be a polynucleotide linker or a non-nucleotide linker. The tandem synthesis of siRNA can be readily adapted to both multiwell/multiplate synthesis platforms as well as large scale synthesis platforms employing batch reactors, synthesis columns, and the like. Alternatively, siRNA molecules can be assembled from two distinct oligonucleotides, wherein one oligonucleotide comprises the sense strand and the other comprises the antisense strand of the siRNA. For example, each strand can be synthesized separately and joined together by hybridization or ligation following synthesis and/or deprotection. In certain other instances, siRNA molecules can be synthesized as a single continuous oligonucleotide fragment, where the self-complementary sense and antisense regions hybridize to form an siRNA duplex having hairpin secondary structure.

c. Modifying siRNA Sequences

In certain aspects, siRNA molecules comprise a duplex having two strands and at least one modified nucleotide in the double-stranded region, wherein each strand is about 15 to about 60 nucleotides in length. Advantageously, the modified siRNA is less immunostimulatory than a corresponding unmodified siRNA sequence, but retains the capability of silencing the expression of a target sequence. In preferred embodiments, the degree of chemical modifications introduced into the siRNA molecule strikes a balance between reduction or abrogation of the immunostimulatory properties of the siRNA and retention of RNAi activity. As a non-limiting example, an siRNA molecule that targets a gene of interest can be minimally modified (e.g., less than about 30%, 25%, 20%, 15%, 10%, or 5% modified) at selective uridine and/or guanosine nucleotides within the siRNA duplex to eliminate the immune response generated by the siRNA while retaining its capability to silence target gene expression.

Examples of modified nucleotides suitable for use in the invention include, but are not limited to, ribonucleotides having a 2'-O-methyl (2'OMe), 2'-deoxy-2'-fluoro(2'F), 2'-deoxy, 5-C-methyl, 2'-O-(2-methoxyethyl) (MOE), 4'-thio, 2'-amino, or 2'-C-allyl group. Modified nucleotides having a Northern conformation such as those described in, e.g., Saenger, *Principles of Nucleic Acid Structure*, Springer-Verlag Ed. (1984), are also suitable for use in siRNA molecules. Such modified nucleotides include, without limitation, locked nucleic acid (LNA) nucleotides (e.g., 2'-O, 4'-C-methylene-(D-ribofuranosyl) nucleotides), 2'-O-(2-methoxyethyl) (MOE) nucleotides, 2'-methyl-thio-ethyl nucleotides, 2'-deoxy-2'-fluoro(2'F) nucleotides, 2'-deoxy-2'-chloro(2'Cl) nucleotides, and 2'-azido nucleotides. In certain instances, the siRNA molecules described herein include one or more G-clamp nucleotides. A G-clamp nucleotide refers to a modified cytosine analog wherein the modifications confer the ability to hydrogen bond both Watson-Crick and Hoogsteen faces of a complementary guanine nucleotide within a duplex (see, e.g., Lin et al., *J. Am. Chem. Soc.,* 120:8531-8532 (1998)). In addition, nucleotides having a nucleotide base analog such as, for example, C-phenyl, C-naphthyl, other aromatic derivatives, inosine, azole carboxamides, and nitroazole derivatives such as 3-nitropyrrole, 4-nitroindole, 5-nitroindole, and 6-nitroindole (see, e.g., Loakes, *Nucl. Acids Res.,* 29:2437-2447 (2001)) can be incorporated into siRNA molecules.

In certain embodiments, siRNA molecules may further comprise one or more chemical modifications such as terminal cap moieties, phosphate backbone modifications, and the like. Examples of terminal cap moieties include, without limitation, inverted deoxy abasic residues, glyceryl modifications, 4',5'-methylene nucleotides, 1-(β-D-erythrofuranosyl) nucleotides, 4'-thio nucleotides, carbocyclic nucleotides, 1,5-anhydrohexitol nucleotides, L-nucleotides, α-nucleotides, modified base nucleotides, threo-pentofuranosyl nucleotides, acyclic 3',4'-seco nucleotides, acyclic 3,4-dihydroxybutyl nucleotides, acyclic 3,5-dihydroxypentyl nucleotides, 3'-3'-inverted nucleotide moieties, 3'-3'-inverted abasic moieties, 3'-2'-inverted nucleotide moieties, 3'-2'-inverted abasic moieties, 5'-5'-inverted nucleotide moieties, 5'-5'-inverted abasic moieties, 3'-5'-inverted deoxy abasic moieties, 5'-amino-alkyl phosphate, 1,3-diamino-2-propyl phosphate, 3-aminopropyl phosphate, 6-aminohexyl phosphate, 1,2-aminododecyl phosphate, hydroxypropyl phosphate, 1,4-butanediol phosphate, 3'-phosphoramidate, 5'-phosphoramidate, hexylphosphate, aminohexyl phosphate, 3'-phosphate, 5'-amino, 3'-phosphorothioate, 5'-phosphorothioate, phosphorodithioate, and bridging or non-bridging methylphosphonate or 5'-mercapto moieties (see, e.g., U.S. Pat. No. 5,998,203; Beaucage et al., *Tetrahedron* 49:1925 (1993)). Non-limiting examples of phosphate backbone modifications (i.e., resulting in modified internucleotide linkages) include phosphorothioate, phosphorodithioate, methylphosphonate, phosphotriester, morpholino, amidate, carbamate, carboxymethyl, acetamidate, polyamide, sulfonate, sulfonamide, sulfamate, formacetal, thioformacetal, and alkylsilyl substitutions (see, e.g., Hunziker et al., *Nucleic Acid Analogues: Synthesis and Properties, in Modern Synthetic Methods*, VCH, 331-417 (1995); Mesmaeker et al., *Novel Backbone Replacements for Oligonucleotides, in Carbohydrate Modifications in Antisense Research*, ACS, 24-39 (1994)). Such chemical modifications can occur at the 5'-end and/or 3'-end of the sense strand, antisense strand, or both strands of the siRNA. The disclosures of these references are herein incorporated by reference in their entirety for all purposes.

In some embodiments, the sense and/or antisense strand of the siRNA molecule can further comprise a 3'-terminal overhang having about 1 to about 4 (e.g., 1, 2, 3, or 4) 2'-deoxy ribonucleotides and/or any combination of modified and unmodified nucleotides. Additional examples of modified nucleotides and types of chemical modifications that can be introduced into siRNA molecules are described, e.g., in UK Patent No. GB 2,397,818 B and U.S. Patent Publication Nos. 20040192626, 20050282188, and 20070135372, the disclosures of which are herein incorporated by reference in their entirety for all purposes.

The siRNA molecules described herein can optionally comprise one or more non-nucleotides in one or both strands of the siRNA. As used herein, the term "non-nucleotide" refers to any group or compound that can be incorporated into a nucleic acid chain in the place of one or more nucleotide units, including sugar and/or phosphate substitutions, and allows the remaining bases to exhibit their activity. The group or compound is abasic in that it does not contain a commonly recognized nucleotide base such as adenosine, guanine, cytosine, uracil, or thymine and therefore lacks a base at the 1'-position.

In other embodiments, chemical modification of the siRNA comprises attaching a conjugate to the siRNA molecule. The conjugate can be attached at the 5' and/or 3'-end of the sense and/or antisense strand of the siRNA via a covalent attachment such as, e.g., a biodegradable linker. The conjugate can also be attached to the siRNA, e.g., through a carbamate group or other linking group (see, e.g., U.S. Patent Publication Nos. 20050074771, 20050043219, and 20050158727). In certain instances, the conjugate is a molecule that facilitates the delivery of the siRNA into a cell. Examples of conjugate molecules suitable for attachment to siRNA include, without limitation, steroids such as cholesterol, glycols such as polyethylene glycol (PEG), human serum albumin (HSA), fatty acids, carotenoids, terpenes, bile acids, folates (e.g., folic acid, folate analogs and derivatives thereof), sugars (e.g., galactose, galactosamine, N-acetyl galactosamine, glucose, mannose, fructose, fucose, etc.), phospholipids, peptides, ligands for cellular receptors capable of mediating cellular uptake, and combinations thereof (see, e.g., U.S. Patent Publication Nos. 20030130186, 20040110296, and 20040249178; U.S. Pat. No. 6,753,423). Other examples include the lipophilic moiety, vitamin, polymer, peptide, protein, nucleic acid, small molecule, oligosaccharide, carbohydrate cluster, intercalator, minor groove binder, cleaving agent, and cross-linking agent conjugate molecules described in U.S. Patent Publication Nos. 20050119470 and 20050107325. Yet other examples include the 2'-O-alkyl amine, 2'-O-alkoxyalkyl amine, polyamine, C5-cationic modified pyrimidine, cationic peptide, guanidinium group, amidininium group, cationic amino acid conjugate molecules described in U.S. Patent Publication No. 20050153337. Additional examples include the hydrophobic group, membrane active compound, cell penetrating compound, cell targeting signal, interaction modifier, and steric stabilizer conjugate molecules described in U.S. Patent Publication No. 20040167090. Further examples include the conjugate molecules described in U.S. Patent Publication No. 20050239739. The type of conjugate used and the extent of conjugation to the siRNA molecule can be evaluated for improved pharmacokinetic profiles, bioavailability, and/or stability of the siRNA while retaining RNAi activity. As such, one skilled in the art can screen siRNA molecules having various conjugates attached thereto to identify ones having improved properties and full RNAi activity using any of a variety of well-known in vitro cell culture or in vivo animal models. The disclosures of the above-described patent documents are herein incorporated by reference in their entirety for all purposes.

d. Target Genes

The siRNA component of the nucleic acid-lipid particles described herein can be used to downregulate or silence the translation (i.e., expression) of a gene of interest. Genes of interest include, but are not limited to, genes associated with viral infection and survival, genes associated with metabolic diseases and disorders (e.g., liver diseases and disorders), genes associated with tumorigenesis and cell transformation (e.g., cancer), angiogenic genes, immunomodulator genes such as those associated with inflammatory and autoimmune responses, ligand receptor genes, and genes associated with neurodegenerative disorders.

Genes associated with viral infection and survival include those expressed by a virus in order to bind, enter, and replicate in a cell. Of particular interest are viral sequences associated with chronic viral diseases. Viral sequences of particular interest include sequences of Filoviruses such as Ebola virus and Marburg virus (see, e.g., Geisbert et al., *J. Infect. Dis.,* 193:1650-1657 (2006)); Arenaviruses such as Lassa virus, Junin virus, Machupo virus, Guanarito virus, and Sabia virus (Buchmeier et al., *Arenaviridae*: the viruses and their replication, In: FIELDS VIROLOGY, Knipe et al. (eds.), 4th ed., Lippincott-Raven, Philadelphia, (2001)); Influenza viruses such as Influenza A, B, and C viruses, (see, e.g., Steinhauer et al., *Annu Rev Genet.,* 36:305-332 (2002); and Neumann et al., *J Gen Virol.,* 83:2635-2662 (2002)); Hepatitis viruses (see, e.g., Hamasaki et al., *FEBS Lett.,* 543:51 (2003); Yokota et al., *EMBO Rep.,* 4:602 (2003); Schlomai et al., *Hepatology,* 37:764 (2003); Wilson et al., *Proc. Natl. Acad. Sci. USA,* 100:2783 (2003); Kapadia et al., *Proc. Natl. Acad. Sci. USA,* 100:2014 (2003); and FIELDS VIROLOGY, Knipe et al. (eds.), 4th ed., Lippincott-Raven, Philadelphia (2001)); Human Immunodeficiency Virus (HIV) (Banerjea et al., *Mol. Ther.,* 8:62 (2003); Song et al., *J. Virol.,* 77:7174 (2003); Stephenson, *JAMA,* 289:1494 (2003); Qin et al., *Proc. Natl. Acad. Sci. USA,* 100:183 (2003)); Herpes viruses (Jia et al., *J. Virol.,* 77:3301 (2003)); and Human Papilloma Viruses (HPV) (Hall et al., *J. Virol.,* 77:6066 (2003); Jiang et al., *Oncogene,* 21:6041 (2002)).

Exemplary Filovirus nucleic acid sequences that can be silenced include, but are not limited to, nucleic acid sequences encoding structural proteins (e.g., VP30, VP35, nucleoprotein (NP), polymerase protein (L-pol)) and membrane-associated proteins (e.g., VP40, glycoprotein (GP), VP24). Complete genome sequences for Ebola virus are set forth in, e.g., Genbank Accession Nos. NC_002549; AY769362; NC_006432; NC_004161; AY729654; AY354458; AY142960; AB050936; AF522874; AF499101; AF272001; and AF086833. Ebola virus VP24 sequences are set forth in, e.g., Genbank Accession Nos. U77385 and AY058897. Ebola virus L-pol sequences are set forth in, e.g., Genbank Accession No. X67110. Ebola virus VP40 sequences are set forth in, e.g., Genbank Accession No. AY058896. Ebola virus NP sequences are set forth in, e.g., Genbank Accession No. AY058895. Ebola virus GP sequences are set forth in, e.g., Genbank Accession No. AY058898; Sanchez et al., *Virus Res.,* 29:215-240 (1993); Will et al., *J. Virol.,* 67:1203-1210 (1993); Volchkov et al., *FEBS Lett.,* 305:181-184 (1992); and U.S. Pat. No. 6,713, 069. Additional Ebola virus sequences are set forth in, e.g., Genbank Accession Nos. L11365 and X61274. Complete genome sequences for Marburg virus are set forth in, e.g., Genbank Accession Nos. NC_001608; AY430365; AY430366; and AY358025. Marburg virus GP sequences are set forth in, e.g., Genbank Accession Nos. AF005734; AF005733; and AF005732. Marburg virus VP35 sequences are set forth in, e.g., Genbank Accession Nos. AF005731 and AF005730. Additional Marburg virus sequences are set forth in, e.g., Genbank Accession Nos. X64406; Z29337; AF005735; and Z12132. Non-limiting examples of siRNA molecules targeting Ebola virus and Marburg virus nucleic acid sequences include those described in U.S. Patent Publication No. 20070135370, the disclosure of which is herein incorporated by reference in its entirety for all purposes.

Exemplary Influenza virus nucleic acid sequences that can be silenced include, but are not limited to, nucleic acid sequences encoding nucleoprotein (NP), matrix proteins (M1 and M2), nonstructural proteins (NS1 and NS2), RNA polymerase (PA, PB1, PB2), neuraminidase (NA), and haemagglutinin (HA). Influenza A NP sequences are set forth in, e.g., Genbank Accession Nos. NC_004522; AY818138; AB166863; AB188817; AB189046; AB189054; AB189062; AY646169; AY646177; AY651486; AY651493; AY651494; AY651495; AY651496; AY651497; AY651498; AY651499; AY651500; AY651501; AY651502; AY651503; AY651504; AY651505; AY651506; AY651507; AY651509; AY651528; AY770996; AY790308; AY818138; and AY818140. Influenza A PA sequences are set forth in, e.g., Genbank Accession Nos. AY818132; AY790280; AY646171; AY818132; AY818133; AY646179; AY818134; AY551934; AY651613; AY651610; AY651620; AY651617; AY651600; AY651611; AY651606; AY651618; AY651608; AY651607; AY651605; AY651609; AY651615; AY651616; AY651640; AY651614; AY651612; AY651621; AY651619; AY770995; and AY724786. Non-limiting examples of siRNA molecules targeting Influenza virus nucleic acid sequences include those described in U.S. Patent Publication No. 20070218122, the disclosure of which is herein incorporated by reference in its entirety for all purposes.

Exemplary hepatitis virus nucleic acid sequences that can be silenced include, but are not limited to, nucleic acid sequences involved in transcription and translation (e.g., En1, En2, X, P) and nucleic acid sequences encoding structural proteins (e.g., core proteins including C and C-related proteins, capsid and envelope proteins including S, M, and/or L proteins, or fragments thereof) (see, e.g., FIELDS VIROLOGY, supra). Exemplary Hepatits C virus (HCV) nucleic acid sequences that can be silenced include, but are not limited to, the 5'-untranslated region (5'-UTR), the 3'-untranslated region (3'-UTR), the polyprotein translation initiation codon region, the internal ribosome entry site (IRES) sequence, and/or nucleic acid sequences encoding the core protein, the E1 protein, the E2 protein, the p7 protein, the NS2 protein, the NS3 protease/helicase, the NS4A protein, the NS4B protein, the NS5A protein, and/or the NS5B RNA-dependent RNA polymerase. HCV genome sequences are set forth in, e.g., Genbank Accession Nos. NC_004102 (HCV genotype 1a), AJ238799 (HCV genotype 1b), NC_009823 (HCV genotype 2), NC_009824 (HCV genotype 3), NC_009825 (HCV genotype 4), NC_009826 (HCV genotype 5), and NC_009827 (HCV genotype 6). Hepatitis A virus nucleic acid sequences are set forth in, e.g., Genbank Accession No. NC_001489; Hepatitis B virus nucleic acid sequences are set forth in, e.g., Genbank Accession No. NC_003977; Hepatitis D virus nucleic acid sequence are set forth in, e.g., Genbank Accession No. NC_001653; Hepatitis E virus nucleic acid sequences are set forth in, e.g., Genbank Accession No. NC_001434; and Hepatitis G virus nucleic acid sequences are set forth in, e.g., Genbank Accession No. NC_001710. Silencing of sequences that encode genes associated with viral infection and survival can conveniently be used in combination with the administration of conventional agents used to treat the viral condition. Non-limiting examples of siRNA molecules targeting hepatitis virus nucleic acid sequences include those described in U.S. Patent Publication Nos. 20060281175, 20050058982, and 20070149470; U.S. Pat. No. 7,348,314; and U.S. Provisional Application No. 61/162,127, filed Mar. 20, 2009, the disclosures of which are herein incorporated by reference in their entirety for all purposes.

Genes associated with metabolic diseases and disorders (e.g., disorders in which the liver is the target and liver diseases and disorders) include, for example, genes expressed in dyslipidemia (e.g., liver X receptors such as LXRα and LXRβ (Genback Accession No. NM_007121), farnesoid X receptors (FXR) (Genbank Accession No. NM_005123), sterol-regulatory element binding protein (SREBP), site-1 protease (SIP), 3-hydroxy-3-methylglutaryl coenzyme-A reductase (HMG coenzyme-A reductase), apolipoprotein B (ApoB) (Genbank Accession No. NM_000384), apolipoprotein CIII (ApoC3) (Genbank Accession Nos. NM_000040 and NG_008949 REGION: 5001.8164), and apolipoprotein E (ApoE) (Genbank Accession Nos. NM_000041 and NG_007084 REGION: 5001.8612)); and diabetes (e.g., glucose 6-phosphatase) (see, e.g., Forman et al., *Cell*, 81:687 (1995); Seol et al., *Mol. Endocrinol.*, 9:72 (1995), Zavacki et al., *Proc. Natl. Acad. Sci. USA*, 94:7909 (1997); Sakai et al., *Cell*, 85:1037-1046 (1996); Duncan et al., *J. Biol. Chem.*, 272:12778-12785 (1997); Willy et al., *Genes Dev.*, 9:1033-1045 (1995); Lehmann et al., *J. Biol. Chem.*, 272:3137-3140 (1997); Janowski et al., *Nature*, 383:728-731 (1996); and Peet et al., *Cell*, 93:693-704 (1998)). One of skill in the art will appreciate that genes associated with metabolic diseases and disorders (e.g., diseases and disorders in which the liver is a target and liver diseases and disorders) include genes that are expressed in the liver itself as well as and genes expressed in other organs and tissues. Silencing of sequences that encode genes associated with metabolic diseases and disorders can conveniently be used in combination with the administration of conventional agents used to treat the disease or disorder. Non-limiting examples of siRNA molecules targeting the ApoB gene include those described in U.S. Patent Publication No. 20060134189, the disclosure of which is herein incorporated by reference in its entirety for all purposes. Non-limiting examples of siRNA molecules targeting the ApoC3 gene include those described in U.S. Provisional Application No. 61/147,235, filed Jan. 26, 2009, the disclosure of which is herein incorporated by reference in its entirety for all purposes.

Examples of gene sequences associated with tumorigenesis and cell transformation (e.g., cancer or other neoplasia) include mitotic kinesins such as Eg5 (KSP, KIF11; Genbank Accession No. NM_004523); serine/threonine kinases such as polo-like kinase 1 (PLK-1) (Genbank Accession No. NM_005030; Barr et al., *Nat. Rev. Mol. Cell Biol.*, 5:429-440 (2004)); tyrosine kinases such as WEE1 (Genbank Accession Nos. NM_003390 and NM_001143976); inhibitors of apoptosis such as XIAP (Genbank Accession No. NM_001167); COPS signalosome subunits such as CSN1, CSN2, CSN3, CSN4, CSN5 (JAB1; Genbank Accession No. NM_006837); CSN6, CSN7A, CSN7B, and CSN8; ubiquitin ligases such as COPT (RFWD2; Genbank Accession Nos. NM_022457 and NM_001001740); and histone deacetylases such as HDAC1, HDAC2 (Genbank Accession No. NM_001527), HDAC3, HDAC4, HDAC5, HDAC6, HDAC7, HDAC8, HDAC9, etc. Non-limiting examples of siRNA molecules targeting the Eg5 and XIAP genes include those described in U.S. patent application Ser. No. 11/807,872, filed May 29, 2007, the disclosure of which is herein incorporated by reference in its entirety for all purposes. Non-limiting examples of siRNA molecules targeting the PLK-1 gene include those described in U.S. Patent Publication Nos. 20050107316 and 20070265438; and U.S. patent application Ser. No. 12/343,342, filed Dec. 23, 2008, the disclosures of which are herein incorporated by reference in their entirety for all purposes. Non-limiting examples of siRNA molecules targeting the CSN5 gene include those described in U.S. Provisional Application No. 61/045,251, filed Apr. 15, 2008, the disclosure of which is herein incorporated by reference in its entirety for all purposes.

Additional examples of gene sequences associated with tumorigenesis and cell transformation include translocation sequences such as MLL fusion genes, BCR-ABL (Wilda et al., *Oncogene*, 21:5716 (2002); Scherr et al., *Blood*, 101:1566 (2003)), TEL-AML1, EWS-FLI1, TLS-FUS, PAX3-FKHR, BCL-2, AML1-ETO, and AML1-MTG8 (Heidenreich et al., *Blood*, 101:3157 (2003)); overexpressed sequences such as multidrug resistance genes (Nieth et al., *FEBS Lett.*, 545:144 (2003); Wu et al, *Cancer Res.* 63:1515 (2003)), cyclins (Li et al., *Cancer Res.*, 63:3593 (2003); Zou et al., *Genes Dev.*, 16:2923 (2002)), beta-catenin (Verma et al., *Clin Cancer Res.*, 9:1291 (2003)), telomerase genes (Kosciolek et al., *Mol Cancer Ther.*, 2:209 (2003)), c-MYC, N-MYC, BCL-2, growth factor receptors (e.g., EGFR/ErbB1 (Genbank Accession Nos. NM_005228, NM_201282, NM_201283, and NM_201284; see also, Nagy et al. *Exp. Cell Res.*, 285:39-49 (2003), ErbB2/HER-2 (Genbank Accession Nos. NM_004448 and NM_001005862), ErbB3 (Genbank Accession Nos. NM_001982 and NM_001005915), and ErbB4 (Genbank Accession Nos. NM_005235 and NM_001042599); and mutated sequences such as RAS (reviewed in Tuschl and Borkhardt, *Mol. Interventions*, 2:158 (2002)). Non-limiting examples of siRNA molecules targeting the EGFR gene include those described in U.S. patent application Ser. No. 11/807,872, filed May 29, 2007, the disclosure of which is herein incorporated by reference in its entirety for all purposes.

Silencing of sequences that encode DNA repair enzymes find use in combination with the administration of chemotherapeutic agents (Collis et al., *Cancer Res.*, 63:1550 (2003)). Genes encoding proteins associated with tumor migration are also target sequences of interest, for example, integrins, selectins, and metalloproteinases. The foregoing examples are not exclusive. Those of skill in the art will understand that any whole or partial gene sequence that facilitates or promotes tumorigenesis or cell transformation, tumor growth, or tumor migration can be included as a template sequence.

Angiogenic genes are able to promote the formation of new vessels. Of particular interest is vascular endothelial growth factor (VEGF) (Reich et al., *Mol. Vis.*, 9:210 (2003)) or VEGFR. siRNA sequences that target VEGFR are set forth in, e.g., GB 2396864; U.S. Patent Publication No. 20040142895; and CA 2456444, the disclosures of which are herein incorporated by reference in their entirety for all purposes.

Anti-angiogenic genes are able to inhibit neovascularization. These genes are particularly useful for treating those cancers in which angiogenesis plays a role in the pathological development of the disease. Examples of anti-angiogenic genes include, but are not limited to, endostatin (see, e.g., U.S. Pat. No. 6,174,861), angiostatin (see, e.g., U.S. Pat. No. 5,639,725), and VEGFR2 (see, e.g., Decaussin et al., *J. Pathol.*, 188: 369-377 (1999)), the disclosures of which are herein incorporated by reference in their entirety for all purposes.

Immunomodulator genes are genes that modulate one or more immune responses. Examples of immunomodulator genes include, without limitation, cytokines such as growth factors (e.g., TGF-α, TFG-β, EGF, FGF, IGF, NGF, PDGF, CGF, GM-CSF, SCF, etc.), interleukins (e.g., IL-2, IL-4, IL-12 (Hill et al., *J. Immunol.*, 171:691 (2003)), IL-15, IL-18, IL-20, etc.), interferons (e.g., IFN-α, IFN-β, IFN-γ, etc.) and TNF. Fas and Fas ligand genes are also immunomodulator target sequences of interest (Song et al., *Nat. Med.*, 9:347 (2003)). Genes encoding secondary signaling molecules in hematopoietic and lymphoid cells are also included in the present invention, for example, Tec family kinases such as Bruton's tyrosine kinase (Btk) (Heinonen et al., *FEBS Lett.*, 527:274 (2002)).

Cell receptor ligands include ligands that are able to bind to cell surface receptors (e.g., insulin receptor, EPO receptor, G-protein coupled receptors, receptors with tyrosine kinase activity, cytokine receptors, growth factor receptors, etc.), to modulate (e.g., inhibit, activate, etc.) the physiological pathway that the receptor is involved in (e.g., glucose level modulation, blood cell development, mitogenesis, etc.). Examples of cell receptor ligands include, but are not limited to, cytokines, growth factors, interleukins, interferons, erythropoietin (EPO), insulin, glucagon, G-protein coupled receptor ligands, etc. Templates coding for an expansion of trinucleotide repeats (e.g., CAG repeats) find use in silencing pathogenic sequences in neurodegenerative disorders caused by the expansion of trinucleotide repeats, such as spinobulbular muscular atrophy and Huntington's Disease (Caplen et al., *Hum. Mol. Genet.*, 11:175 (2002)).

In addition to its utility in silencing the expression of any of the above-described genes for therapeutic purposes, the siRNA described herein are also useful in research and development applications as well as diagnostic, prophylactic, prognostic, clinical, and other healthcare applications. As a non-limiting example, the siRNA can be used in target validation studies directed at testing whether a gene of interest has the potential to be a therapeutic target. The siRNA can also be used in target identification studies aimed at discovering genes as potential therapeutic targets.

2. aiRNA

Like siRNA, asymmetrical interfering RNA (aiRNA) can recruit the RNA-induced silencing complex (RISC) and lead to effective silencing of a variety of genes in mammalian cells by mediating sequence-specific cleavage of the target sequence between nucleotide 10 and 11 relative to the 5' end of the antisense strand (Sun et al., *Nat. Biotech.*, 26:1379-1382 (2008)). Typically, an aiRNA molecule comprises a short RNA duplex having a sense strand and an antisense strand, wherein the duplex contains overhangs at the 3' and 5' ends of the antisense strand. The aiRNA is generally asymmetric because the sense strand is shorter on both ends when compared to the complementary antisense strand. In some aspects, aiRNA molecules may be designed, synthesized, and annealed under conditions similar to those used for siRNA molecules. As a non-limiting example, aiRNA sequences may be selected and generated using the methods described above for selecting siRNA sequences.

In another embodiment, aiRNA duplexes of various lengths (e.g., about 10-25, 12-20, 12-19, 12-18, 13-17, or 14-17 base pairs, more typically 12, 13, 14, 15, 16, 17, 18, 19, or base pairs) may be designed with overhangs at the 3' and 5' ends of the antisense strand to target an mRNA of interest. In certain instances, the sense strand of the aiRNA molecule is about 10-25, 12-20, 12-19, 12-18, 13-17, or 14-17 nucleotides in length, more typically 12, 13, 14, 15, 16, 17, 18, 19, or 20 nucleotides in length. In certain other instances, the antisense strand of the aiRNA molecule is about 15-60, 15-50, or 15-40 nucleotides in length, more typically about 15-30, 15-25, or 19-25 nucleotides in length, and is preferably about 20-24, 21-22, or 21-23 nucleotides in length.

In some embodiments, the 5' antisense overhang contains one, two, three, four, or more nontargeting nucleotides (e.g., "AA", "UU", "dTdT", etc.). In other embodiments, the 3' antisense overhang contains one, two, three, four, or more nontargeting nucleotides (e.g., "AA", "UU", "dTdT", etc.). In certain aspects, the aiRNA molecules described herein may comprise one or more modified nucleotides, e.g., in the double-stranded (duplex) region and/or in the antisense overhangs. As a non-limiting example, aiRNA sequences may comprise one or more of the modified nucleotides described above for siRNA sequences. In a preferred embodiment, the aiRNA molecule comprises 2'OMe nucleotides such as, for example, 2'OMe-guanosine nucleotides, 2'OMe-uridine nucleotides, or mixtures thereof.

In certain embodiments, aiRNA molecules may comprise an antisense strand which corresponds to the antisense strand of an siRNA molecule, e.g., one of the siRNA molecules described herein. In other embodiments, aiRNA molecules may be used to silence the expression of any of the target genes set forth above, such as, e.g., genes associated with viral infection and survival, genes associated with metabolic diseases and disorders, genes associated with tumorigenesis and cell transformation, angiogenic genes, immunomodulator genes such as those associated with inflammatory and autoimmune responses, ligand receptor genes, and genes associated with neurodegenerative disorders.

3. miRNA

Generally, microRNAs (miRNA) are single-stranded RNA molecules of about 21-23 nucleotides in length which regulate gene expression. miRNAs are encoded by genes from whose DNA they are transcribed, but miRNAs are not translated into protein (non-coding RNA); instead, each primary transcript (a pri-miRNA) is processed into a short stem-loop structure called a pre-miRNA and finally into a functional mature miRNA. Mature miRNA molecules are either partially or completely complementary to one or more messenger RNA (mRNA) molecules, and their main function is to downregulate gene expression. The identification of miRNA molecules is described, e.g., in Lagos-Quintana et al., *Science,* 294:853-858; Lau et al., *Science,* 294:858-862; and Lee et al., *Science,* 294:862-864.

The genes encoding miRNA are much longer than the processed mature miRNA molecule. miRNA are first transcribed as primary transcripts or pri-miRNA with a cap and poly-A tail and processed to short, ~70-nucleotide stem-loop structures known as pre-miRNA in the cell nucleus. This processing is performed in animals by a protein complex known as the Microprocessor complex, consisting of the nuclease Drosha and the double-stranded RNA binding protein Pasha (Denli et al., *Nature,* 432:231-235 (2004)). These pre-miRNA are then processed to mature miRNA in the cytoplasm by interaction with the endonuclease Dicer, which also initiates the formation of the RNA-induced silencing complex (RISC) (Bernstein et al., *Nature,* 409:363-366 (2001). Either the sense strand or antisense strand of DNA can function as templates to give rise to miRNA.

When Dicer cleaves the pre-miRNA stem-loop, two complementary short RNA molecules are formed, but only one is integrated into the RISC complex. This strand is known as the guide strand and is selected by the argonaute protein, the catalytically active RNase in the RISC complex, on the basis of the stability of the 5' end (Preall et al., *Curr. Biol.,* 16:530-535 (2006)). The remaining strand, known as the anti-guide or passenger strand, is degraded as a RISC complex substrate (Gregory et al., *Cell,* 123:631-640 (2005)). After integration into the active RISC complex, miRNAs base pair with their complementary mRNA molecules and induce target mRNA degradation and/or translational silencing.

Mammalian miRNA molecules are usually complementary to a site in the 3' UTR of the target mRNA sequence. In certain instances, the annealing of the miRNA to the target mRNA inhibits protein translation by blocking the protein translation machinery. In certain other instances, the annealing of the miRNA to the target mRNA facilitates the cleavage and degradation of the target mRNA through a process similar to RNA interference (RNAi). miRNA may also target methylation of genomic sites which correspond to targeted mRNA. Generally, miRNA function in association with a complement of proteins collectively termed the miRNP.

In certain aspects, the miRNA molecules described herein are about 15-100, 15-90, 15-80, 15-75, 15-70, 15-60, 15-50, or 15-40 nucleotides in length, more typically about 15-30, 15-25, or 19-25 nucleotides in length, and are preferably about 20-24, 21-22, or 21-23 nucleotides in length. In certain other aspects, miRNA molecules may comprise one or more modified nucleotides. As a non-limiting example, miRNA sequences may comprise one or more of the modified nucleotides described above for siRNA sequences. In a preferred embodiment, the miRNA molecule comprises 2'OMe nucleotides such as, for example, 2'OMe-guanosine nucleotides, 2'OMe-uridine nucleotides, or mixtures thereof.

In some embodiments, miRNA molecules may be used to silence the expression of any of the target genes set forth above, such as, e.g., genes associated with viral infection and survival, genes associated with metabolic diseases and disorders, genes associated with tumorigenesis and cell transformation, angiogenic genes, immunomodulator genes such as those associated with inflammatory and autoimmune responses, ligand receptor genes, and genes associated with neurodegenerative disorders.

In other embodiments, one or more agents that block the activity of a miRNA targeting an mRNA of interest are administered using a lipid particle of the invention (e.g., a nucleic acid-lipid particle). Examples of blocking agents include, but are not limited to, steric blocking oligonucleotides, locked nucleic acid oligonucleotides, and Morpholino oligonucleotides. Such blocking agents may bind directly to the miRNA or to the miRNA binding site on the target mRNA.

4. Antisense Oligonucleotides

In one embodiment, the nucleic acid is an antisense oligonucleotide directed to a target gene or sequence of interest. The terms "antisense oligonucleotide" or "antisense" include oligonucleotides that are complementary to a targeted polynucleotide sequence. Antisense oligonucleotides are single strands of DNA or RNA that are complementary to a chosen sequence. Antisense RNA oligonucleotides prevent the translation of complementary RNA strands by binding to the RNA. Antisense DNA oligonucleotides can be used to target a specific, complementary (coding or non-coding) RNA. If binding occurs, this DNA/RNA hybrid can be degraded by the enzyme RNase H. In a particular embodiment, antisense oligonucleotides comprise from about 10 to about 60 nucleotides, more preferably from about 15 to about 30 nucleotides. The term also encompasses antisense oligonucleotides that may not be exactly complementary to the desired target gene. Thus, the invention can be utilized in instances where non-target specific-activities are found with antisense, or where an antisense sequence containing one or more mismatches with the target sequence is the most preferred for a particular use.

Antisense oligonucleotides have been demonstrated to be effective and targeted inhibitors of protein synthesis, and, consequently, can be used to specifically inhibit protein synthesis by a targeted gene. The efficacy of antisense oligonucleotides for inhibiting protein synthesis is well established. For example, the synthesis of polygalactauronase and the muscarine type 2 acetylcholine receptor are inhibited by antisense oligonucleotides directed to their respective mRNA sequences (see, U.S. Pat. Nos. 5,739,119 and 5,759,829). Furthermore, examples of antisense inhibition have been demonstrated with the nuclear protein cyclin, the multiple drug resistance gene (MDR1), ICAM-1, E-selectin, STK-1, striatal GABAA receptor, and human EGF (see, Jaskulski et al., *Science*, 240:1544-6 (1988); Vasanthakumar et al., *Cancer Commun.*, 1:225-32 (1989); Penis et al., *Brain Res Mol Brain Res.*, 15; 57:310-20 (1998); and U.S. Pat. Nos. 5,801,154; 5,789,573; 5,718,709 and 5,610,288). Moreover, antisense constructs have also been described that inhibit and can be used to treat a variety of abnormal cellular proliferations, e.g., cancer (see, U.S. Pat. Nos. 5,747,470; 5,591,317; and 5,783,683). The disclosures of these references are herein incorporated by reference in their entirety for all purposes.

Methods of producing antisense oligonucleotides are known in the art and can be readily adapted to produce an antisense oligonucleotide that targets any polynucleotide sequence. Selection of antisense oligonucleotide sequences specific for a given target sequence is based upon analysis of the chosen target sequence and determination of secondary structure, $T_m$, binding energy, and relative stability. Antisense oligonucleotides may be selected based upon their relative inability to form dimers, hairpins, or other secondary structures that would reduce or prohibit specific binding to the target mRNA in a host cell. Highly preferred target regions of the mRNA include those regions at or near the AUG translation initiation codon and those sequences that are substantially complementary to 5' regions of the mRNA. These secondary structure analyses and target site selection considerations can be performed, for example, using v.4 of the OLIGO primer analysis software (Molecular Biology Insights) and/or the BLASTN 2.0.5 algorithm software (Altschul et al., *Nucleic Acids Res.*, 25:3389-402 (1997)).

5. Ribozymes

According to another embodiment of the invention, nucleic acid-lipid particles are associated with ribozymes. Ribozymes are RNA-protein complexes having specific catalytic domains that possess endonuclease activity (see, Kim et al., *Proc. Natl. Acad. Sci. USA.*, 84:8788-92 (1987); and Forster et a, *Cell*, 49:211-20 (1987)). For example, a large number of ribozymes accelerate phosphoester transfer reactions with a high degree of specificity, often cleaving only one of several phosphoesters in an oligonucleotide substrate (see, Cech et al., *Cell*, 27:487-96 (1981); Michel et al., *J. Mol. Biol.*, 216:585-610 (1990); Reinhold-Hurek et al., *Nature*, 357:173-6 (1992)). This specificity has been attributed to the requirement that the substrate bind via specific base-pairing interactions to the internal guide sequence ("IGS") of the ribozyme prior to chemical reaction.

At least six basic varieties of naturally-occurring enzymatic RNA molecules are known presently. Each can catalyze the hydrolysis of RNA phosphodiester bonds in trans (and thus can cleave other RNA molecules) under physiological conditions. In general, enzymatic nucleic acids act by first binding to a target RNA. Such binding occurs through the target binding portion of an enzymatic nucleic acid which is held in close proximity to an enzymatic portion of the molecule that acts to cleave the target RNA. Thus, the enzymatic nucleic acid first recognizes and then binds a target RNA through complementary base-pairing, and once bound to the correct site, acts enzymatically to cut the target RNA. Strategic cleavage of such a target RNA will destroy its ability to direct synthesis of an encoded protein. After an enzymatic nucleic acid has bound and cleaved its RNA target, it is released from that RNA to search for another target and can repeatedly bind and cleave new targets.

The enzymatic nucleic acid molecule may be formed in a hammerhead, hairpin, hepatitis δ virus, group I intron or RNaseP RNA (in association with an RNA guide sequence), or *Neurospora* VS RNA motif, for example. Specific examples of hammerhead motifs are described in, e.g., Rossi et al., *Nucleic Acids Res.*, 20:4559-65 (1992). Examples of hairpin motifs are described in, e.g., EP 0360257, Hampel et al., *Biochemistry*, 28:4929-33 (1989); Hampel et al., *Nucleic Acids Res.*, 18:299-304 (1990); and U.S. Pat. No. 5,631,359. An example of the hepatitis δ virus motif is described in, e.g., Perrotta et al., *Biochemistry*, 31:11843-52 (1992). An example of the RNaseP motif is described in, e.g., Guerrier-Takada et al., *Cell*, 35:849-57 (1983). Examples of the *Neurospora* VS RNA ribozyme motif is described in, e.g., Saville et al., *Cell*, 61:685-96 (1990); Saville et al., *Proc. Natl. Acad. Sci. USA*, 88:8826-30 (1991); Collins et al., *Biochemistry*, 32:2795-9 (1993). An example of the Group I intron is described in, e.g., U.S. Pat. No. 4,987,071. Important characteristics of enzymatic nucleic acid molecules used according to the invention are that they have a specific substrate binding site which is complementary to one or more of the target gene DNA or RNA regions, and that they have nucleotide sequences within or surrounding that substrate binding site which impart an RNA cleaving activity to the molecule. Thus, the ribozyme constructs need not be limited to specific motifs mentioned herein. The disclosures of these references are herein incorporated by reference in their entirety for all purposes.

Methods of producing a ribozyme targeted to any polynucleotide sequence are known in the art. Ribozymes may be designed as described in, e.g., PCT Publication Nos. WO 93/23569 and WO 94/02595, and synthesized to be tested in vitro and/or in vivo as described therein. The disclosures of these PCT publications are herein incorporated by reference in their entirety for all purposes.

Ribozyme activity can be optimized by altering the length of the ribozyme binding arms or chemically synthesizing ribozymes with modifications that prevent their degradation by serum ribonucleases (see, e.g., PCT Publication Nos. WO 92/07065, WO 93/15187, WO 91/03162, and WO 94/13688; EP 92110298.4; and U.S. Pat. No. 5,334,711, which describe various chemical modifications that can be made to the sugar moieties of enzymatic RNA molecules, the disclosures of which are each herein incorporated by reference in their entirety for all purposes), modifications which enhance their efficacy in cells, and removal of stem II bases to shorten RNA synthesis times and reduce chemical requirements.

6. Immunostimulatory Oligonucleotides

Nucleic acids associated with lipid particles of the present invention may be immunostimulatory, including immunostimulatory oligonucleotides (ISS; single- or double-stranded) capable of inducing an immune response when administered to a subject, which may be a mammal such as a human. ISS include, e.g., certain palindromes leading to hairpin secondary structures (see, Yamamoto et al., *J. Immunol.*, 148:4072-6 (1992)), or CpG motifs, as well as other known ISS features (such as multi-G domains; see; PCT Publication No. WO 96/11266, the disclosure of which is herein incorporated by reference in its entirety for all purposes).

Immunostimulatory nucleic acids are considered to be non-sequence specific when it is not required that they specifically bind to and reduce the expression of a target sequence in order to provoke an immune response. Thus, certain immunostimulatory nucleic acids may comprise a sequence corresponding to a region of a naturally-occurring gene or mRNA, but they may still be considered non-sequence specific immunostimulatory nucleic acids.

In one embodiment, the immunostimulatory nucleic acid or oligonucleotide comprises at least one CpG dinucleotide. The oligonucleotide or CpG dinucleotide may be unmethylated or methylated. In another embodiment, the immunostimulatory nucleic acid comprises at least one CpG dinucleotide having a methylated cytosine. In one embodiment, the nucleic acid comprises a single CpG dinucleotide, wherein the cytosine in the CpG dinucleotide is methylated. In an alternative embodiment, the nucleic acid comprises at least two CpG dinucleotides, wherein at least one cytosine in the CpG dinucleotides is methylated. In a further embodiment, each cytosine in the CpG dinucleotides present in the sequence is methylated. In another embodiment, the nucleic acid comprises a plurality of CpG dinucleotides, wherein at least one of the CpG dinucleotides comprises a methylated cytosine. Examples of immunostimulatory oligonucleotides suitable for use in the compositions and methods of the present invention are described in PCT Application No. PCT/US08/88676, filed Dec. 31, 2008, PCT Publication Nos. WO 02/069369 and WO 01/15726, U.S. Pat. No. 6,406,705, and Raney et al., *J. Pharm. Exper. Ther.*, 298:1185-92 (2001), the disclosures of which are each herein incorporated by reference in their entirety for all purposes. In certain embodiments, the oligonucleotides used in the compositions and methods of the invention have a phosphodiester ("PO") backbone or a phosphorothioate ("PS") backbone, and/or at least one methylated cytosine residue in a CpG motif.

B. Other Active Agents

In certain embodiments, the active agent associated with the lipid particles of the invention may comprise one or more therapeutic proteins, polypeptides, or small organic molecules or compounds. Non-limiting examples of such therapeutically effective agents or drugs include oncology drugs (e.g., chemotherapy drugs, hormonal therapeutic agents, immunotherapeutic agents, radiotherapeutic agents, etc.), lipid-lowering agents, anti-viral drugs, anti-inflammatory compounds, antidepressants, stimulants, analgesics, antibiotics, birth control medication, antipyretics, vasodilators, anti-angiogenics, cytovascular agents, signal transduction inhibitors, cardiovascular drugs such as anti-arrhythmic agents, hormones, vasoconstrictors, and steroids. These active agents may be administered alone in the lipid particles of the invention, or in combination (e.g., co-administered) with lipid particles of the invention comprising nucleic acid such as interfering RNA.

Non-limiting examples of chemotherapy drugs include platinum-based drugs (e.g., oxaliplatin, cisplatin, carboplatin, spiroplatin, iproplatin, satraplatin, etc.), alkylating agents (e.g., cyclophosphamide, ifosfamide, chlorambucil, busulfan, melphalan, mechlorethamine, uramustine, thiotepa, nitrosoureas, etc.), anti-metabolites (e.g., 5-fluorouracil (5-FU), azathioprine, methotrexate, leucovorin, capecitabine, cytarabine, floxuridine, fludarabine, gemcitabine, pemetrexed, raltitrexed, etc.), plant alkaloids (e.g., vincristine, vinblastine, vinorelbine, vindesine, podophyllotoxin, paclitaxel (taxol), docetaxel, etc.), topoisomerase inhibitors (e.g., irinotecan (CPT-11; Camptosar), topotecan, amsacrine, etoposide (VP16), etoposide phosphate, teniposide, etc.), antitumor antibiotics (e.g., doxorubicin, adriamycin, daunorubicin, epirubicin, actinomycin, bleomycin, mitomycin, mitoxantrone, plicamycin, etc.), tyrosine kinase inhibitors (e.g., gefitinib (Iressa), sunitinib (Sutent®; SU11248), erlotinib (Tarceva®; OSI-1774), lapatinib (GW572016; GW2016), canertinib (CI 1033), semaxinib (SU5416), vatalanib (PTK787/ZK222584), sorafenib (BAY 43-9006), imatinib (Gleevec®; STI571), dasatinib (BMS-354825), leflunomide (SU101), vandetanib (Zactima™; ZD6474), etc.), pharmaceutically acceptable salts thereof, stereoisomers thereof, derivatives thereof, analogs thereof, and combinations thereof.

Examples of conventional hormonal therapeutic agents include, without limitation, steroids (e.g., dexamethasone), finasteride, aromatase inhibitors, tamoxifen, and goserelin as well as other gonadotropin-releasing hormone agonists (GnRH).

Examples of conventional immunotherapeutic agents include, but are not limited to, immunostimulants (e.g., *Bacillus* Calmette-Guérin (BCG), levamisole, interleukin-2, alpha-interferon, etc.), monoclonal antibodies (e.g., anti-CD20, anti-HER2, anti-CD52, anti-HLA-DR, and anti-VEGF monoclonal antibodies), immunotoxins (e.g., anti-CD33 monoclonal antibody-calicheamicin conjugate, anti-CD22 monoclonal antibody-pseudomonas exotoxin conjugate, etc.), and radioimmunotherapy (e.g., anti-CD20 monoclonal antibody conjugated to $^{111}$In, $^{90}$Y, or $^{131}$I, etc.).

Examples of conventional radiotherapeutic agents include, but are not limited to, radionuclides such as $^{47}$Sc, $^{64}$Cu, $^{67}$Cu, $^{89}$Sr, $^{86}$Y, $^{87}$Y, $^{90}$Y, $^{105}$Rh, $^{111}$Ag, $^{111}$In, $^{117m}$Sn, $^{149}$Pm, $^{153}$Sm, $^{166}$Ho, $^{177}$Lu, $^{186}$Re, $^{188}$Re, $^{211}$At, and, $^{212}$Bi, optionally conjugated to antibodies directed against tumor antigens.

Additional oncology drugs that may be used according to the invention include, but are not limited to, alkeran, allopurinol, altretamine, amifostine, anastrozole, araC, arsenic trioxide, bexarotene, biCNU, carmustine, CCNU, celecoxib, cladribine, cyclosporin A, cytosine arabinoside, cytoxan, dexrazoxane, DTIC, estramustine, exemestane, FK506, gemtuzumab-ozogamicin, hydrea, hydroxyurea, idarubicin, interferon, letrozole, Leustatin, leuprolide, litretinoin, megastrol, L-PAM, mesna, methoxsalen, mithramycin, nitrogen mustard, pamidronate, Pegademase, pentostatin, porfimer sodium, prednisone, rituxan, streptozocin, STI-571, taxotere, temozolamide, VM-26, toremifene, tretinoin, ATRA, valrubicin, and velban. Other examples of oncology drugs that may be used according to the invention are ellipticin and ellipticin analogs or derivatives, epothilones, intracellular kinase inhibitors, and camptothecins.

Non-limiting examples of lipid-lowering agents for treating a lipid disease or disorder associated with elevated triglycerides, cholesterol, and/or glucose include statins, fibrates, ezetimibe, thiazolidinediones, niacin, beta-blockers, nitroglycerin, calcium antagonists, fish oil, and mixtures thereof.

Examples of anti-viral drugs include, but are not limited to, abacavir, aciclovir, acyclovir, adefovir, amantadine, amprenavir, arbidol, atazanavir, atripla, cidofovir, combivir, darunavir, delavirdine, didanosine, docosanol, edoxudine, efavirenz, emtricitabine, enfuvirtide, entecavir, entry inhibitors, famciclovir, fixed dose combinations, fomivirsen, fosamprenavir, foscarnet, fosfonet, fusion inhibitors, ganciclovir, ibacitabine, immunovir, idoxuridine, imiquimod, indinavir, inosine, integrase inhibitors, interferon type III (e.g., IFN-λ molecules such as IFN-λ1, IFN-λ2, and IFN-λ3), interferon type II (e.g., IFN-γ), interferon type I (e.g., IFN-α such as PEGylated IFN-α, IFN-β, IFN-κ, IFN-δ, IFN-ε, IFN-τ, IFN-ω, and IFN-ζ, interferon, lamivudine, lopinavir, loviride, MK-0518, maraviroc, moroxydine, nelfinavir, nevirapine, nexavir, nucleoside analogues, oseltamivir, penciclovir, peramivir, pleconaril, podophyllotoxin, protease inhibitors, reverse transcriptase inhibitors, ribavirin, rimantadine, ritonavir, saquinavir, stavudine, synergistic enhancers, tenofovir, tenofovir disoproxil, tipranavir, trifluridine, trizivir, tromantadine, truvada, valaciclovir, valganciclovir, vicriviroc, vidarabine, viramidine, zalcitabine, zanamivir, zidovudine, pharmaceutically acceptable salts thereof, stereoisomers thereof, derivatives thereof, analogs thereof, and mixtures thereof.

V. Lipid Particles

The lipid particles of the invention typically comprise an active agent or therapeutic agent, a cationic lipid, a non-cationic lipid, and a conjugated lipid that inhibits aggregation of particles. In some embodiments, the active agent or therapeutic agent is fully encapsulated within the lipid portion of the lipid particle such that the active agent or therapeutic agent in the lipid particle is resistant in aqueous solution to enzymatic degradation, e.g., by a nuclease or protease. In other embodiments, the lipid particles described herein are substantially non-toxic to mammals such as humans. The lipid particles of the invention typically have a mean diameter of from about 40 nm to about 150 nm, from about 50 nm to about 150 nm, from about 60 nm to about 130 nm, from about 70 nm to about 110 nm, or from about 70 to about 90 nm.

In preferred embodiments, the lipid particles of the invention are serum-stable nucleic acid-lipid particles (SNALP) which comprise an interfering RNA (e.g., siRNA, aiRNA, and/or miRNA), a cationic lipid (e.g., a cationic lipid of Formulas I, II, and/or III), a non-cationic lipid (e.g., cholesterol alone or mixtures of one or more phospholipids and cholesterol), and a conjugated lipid that inhibits aggregation of the particles (e.g., one or more PEG-lipid conjugates). The SNALP may comprise at least 1, 2, 3, 4, 5, 6, 7, 8, 9, 10, or more unmodified and/or modified interfering RNA molecules. Nucleic acid-lipid particles and their method of preparation are described in, e.g., U.S. Pat. Nos. 5,753,613; 5,785,992; 5,705,385; 5,976,567; 5,981,501; 6,110,745; and 6,320,017; and PCT Publication No. WO 96/40964, the disclosures of which are each herein incorporated by reference in their entirety for all purposes.

A. Cationic Lipids

Any of a variety of cationic lipids may be used in the lipid particles of the invention (e.g., SNALP), either alone or in combination with one or more other cationic lipid species or non-cationic lipid species.

Cationic lipids which are useful in the present invention can be any of a number of lipid species which carry a net positive charge at physiological pH. Such lipids include, but are not limited to, N,N-dioleyl-N,N-dimethylammonium chloride (DODAC), 1,2-dioleyloxy-N,N-dimethylaminopropane (DODMA), 1,2-distearyloxy-N,N-dimethylaminopropane (DSDMA), N-(1-(2,3-dioleyloxy)propyl)-N,N,N-trimethylammonium chloride (DOTMA), N,N-distearyl-N,N-dimethylammonium bromide (DDAB), N-(1-(2,3-dioleoyloxy)propyl)-N,N,N-trimethylammonium chloride (DOTAP), 3-(N-(N',N'-dimethylaminoethane)-carbamoyl) cholesterol (DC-Chol), N-(1,2-dimyristyloxyprop-3-yl)-N,N-dimethyl-N-hydroxyethyl ammonium bromide (DMRIE), 2,3-dioleyloxy-N-[2(spermine-carboxamido)ethyl]-N,N-dimethyl-1-propanaminiumtrifluoroacetate (DOSPA), dioctadecylamidoglycyl spermine (DOGS), 3-dimethylamino-2-(cholest-5-en-3-beta-oxybutan-4-oxy)-1-(cis,cis-9,12-octadecadienoxy)propane (CLinDMA), 2-[5'-(cholest-5-en-3.beta.-oxy)-3'-oxapentoxy)-3-dimethyl-1-(cis,cis-9',1-2'-octadecadienoxy)propane (CpLinDMA), N,N-dimethyl-3,4-dioleyloxybenzylamine (DMOBA), 1,2-N,N'-dioleylcarbamyl-3-dimethylaminopropane (DOcarbDAP), 1,2-N,N'-Dilinoleylcarbamyl-3-dimethylaminopropane (DLincarbDAP), 1,2-Dilinoleoylcarbamyl-3-dimethylaminopropane (DLinCDAP), and mixtures thereof A number of these lipids and related analogs have been described in U.S. Patent Publication Nos. 20060083780 and 20060240554; U.S. Pat. Nos. 5,208,036; 5,264,618; 5,279,833; 5,283,185; 5,753,613; and 5,785,992; and PCT Publication No. WO 96/10390, the disclosures of which are each herein incorporated by reference in their entirety for all purposes. Additionally, a number of commercial preparations of cationic lipids are available and can be used in the present invention. These include, e.g., LIPOFECTIN® (commercially available cationic liposomes comprising DOTMA and DOPE, from GIBCO/BRL, Grand Island, N.Y., USA); LIPOFECTAMINE® (commercially available cationic liposomes comprising DOSPA and DOPE, from GIBCO/BRL); and TRANSFECTAM® (commercially available cationic liposomes comprising DOGS from Promega Corp., Madison, Wis., USA).

Additionally, cationic lipids of Formula I having the following structures are useful in the present invention.

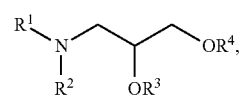

(I)

wherein $R^1$ and $R^2$ are independently selected and are H or $C_1$-$C_3$ alkyls, $R^3$ and $R^4$ are independently selected and are alkyl groups having from about 10 to about 20 carbon atoms, and at least one of $R^3$ and $R^4$ comprises at least two sites of unsaturation. In certain instances, $R^3$ and $R^4$ are both the same, i.e., $R^3$ and $R^4$ are both linoleyl ($C_{18}$), etc. In certain other instances, $R^3$ and $R^4$ are different, i.e., $R^3$ is tetradectrienyl ($C_{14}$) and $R^4$ is linoleyl ($C_{18}$). In a preferred embodiment, the cationic lipid of Formula I is symmetrical, i.e., $R^3$ and $R^4$ are both the same. In another preferred embodiment, both $R^3$ and $R^4$ comprise at least two sites of unsaturation. In some embodiments, $R^3$ and $R^4$ are independently selected from the group consisting of dodecadienyl, tetradecadienyl, hexadecadienyl, linoleyl, and icosadienyl. In a preferred embodiment, $R^3$ and $R^4$ are both linoleyl. In some embodiments, $R^3$ and $R^4$ comprise at least three sites of unsaturation and are independently selected from, e.g., dodecatrienyl, tetradectrienyl, hexadecatrienyl, linolenyl, and icosatrienyl. In particularly preferred embodiments, the cationic lipid of Formula I is 1,2-dilinoleyloxy-N,N-dimethylaminopropane (DLinDMA) or 1,2-dilinolenyloxy-N,N-dimethylaminopropane (DLenDMA).

Furthermore, cationic lipids of Formula II having the following structures are useful in the present invention.

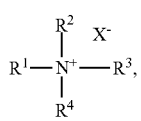

(II)

wherein $R^1$ and $R^2$ are independently selected and are H or $C_1$-$C_3$ alkyls, $R^3$ and $R^4$ are independently selected and are alkyl groups having from about 10 to about 20 carbon atoms, and at least one of $R^3$ and $R^4$ comprises at least two sites of unsaturation. In certain instances, $R^3$ and $R^4$ are both the same, i.e., $R^3$ and $R^4$ are both linoleyl ($C_{18}$), etc. In certain other instances, $R^3$ and $R^4$ are different, i.e., $R^3$ is tetradectrienyl ($C_{14}$) and $R^4$ is linoleyl ($C_{18}$). In a preferred embodiment, the cationic lipids of the present invention are symmetrical, i.e., $R^3$ and $R^4$ are both the same. In another preferred embodiment, both $R^3$ and $R^4$ comprise at least two sites of unsaturation. In some embodiments, $R^3$ and $R^4$ are independently selected from the group consisting of dodecadienyl, tetradecadienyl, hexadecadienyl, linoleyl, and icosadienyl. In a preferred embodiment, $R^3$ and $R^4$ are both linoleyl. In some embodiments, $R^3$ and $R^4$ comprise at least three sites of unsaturation and are independently selected from, e.g., dodecatrienyl, tetradectrienyl, hexadecatrienyl, linolenyl, and icosatrienyl.

Moreover, cationic lipids of Formula III having the following structures (or salts thereof) are useful in the present invention.

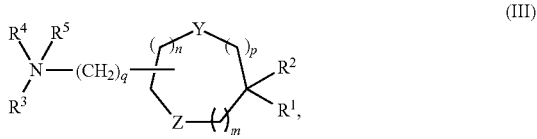

(III)

Wherein $R^1$ and $R^2$ are either the same or different and independently optionally substituted $C_{12}$-$C_{24}$ alkyl, optionally substituted $C_{12}$-$C_{24}$ alkenyl, optionally substituted $C_{12}$-$C_{24}$ alkynyl, or optionally substituted $C_{12}$-$C_{24}$ acyl; $R^3$ and $R^4$ are either the same or different and independently optionally substituted $C_1$-$C_6$ alkyl, optionally substituted $C_1$-$C_6$ alkenyl, or optionally substituted $C_1$-$C_6$ alkynyl or $R^3$ and $R^4$ may join to form an optionally substituted heterocyclic ring of 4 to 6 carbon atoms and 1 or 2 heteroatoms chosen from nitrogen and oxygen; $R^5$ is either absent or hydrogen or $C_1$-$C_6$ alkyl to provide a quaternary amine; m, n, and p are either the same or different and independently either 0 or 1 with the proviso that m, n, and p are not simultaneously 0; q is 0, 1, 2, 3, or 4; and Y and Z are either the same or different and independently O, S, or NH.

In some embodiments, the cationic lipid of Formula III is 2,2-dilinoleyl-4-(2-dimethylaminoethyl)-[1,3]-dioxolane (DLin-K-C2-DMA; "XTC2"), 2,2-dilinoleyl-4-(3-dimethylaminopropyl)-[1,3]-dioxolane (DLin-K-C3-DMA), 2,2-dilinoleyl-4-(4-dimethylaminobutyl)-[1,3]-dioxolane (DLin-K-C4-DMA), 2,2-dilinoleyl-5-dimethylaminomethyl-[1,3]-dioxane (DLin-K6-DMA), 2,2-dilinoleyl-4-N-methylpepiazino-[1,3]-dioxolane (DLin-K-MPZ), 2,2-dilinoleyl-4-dimethylaminomethyl-[1,3]-dioxolane (DLin-K-DMA), 1,2-dilinoleylcarbamoyloxy-3-dimethylaminopropane (DLin-C-DAP), 1,2-dilinoleyoxy-3-(dimethylamino)acetoxypropane (DLin-DAC), 1,2-dilinoleyoxy-3-morpholinopropane (DLin-MA), 1,2-dilinoleoyl-3-dimethylaminopropane (DLinDAP), 1,2-dilinoleylthio-3-dimethylaminopropane (DLin-S-DMA), 1-linoleoyl-2-linoleyloxy-3-dimethylaminopropane (DLin-2-DMAP), 1,2-dilinoleyloxy-3-trimethylaminopropane chloride salt (DLin-TMA.Cl), 1,2-dilinoleoyl-3-trimethylaminopropane chloride salt (DLin-TAP.Cl), 1,2-dilinoleyloxy-3-(N-methylpiperazino)propane (DLin-MPZ), 3-(N,N-dilinoleylamino)-1,2-propanediol (DLinAP), 3-(N,N-dioleylamino)-1,2-propanedio (DOAP), 1,2-dilinoleyloxo-3-(2-N,N-dimethylamino)ethoxypropane (DLin-EG-DMA), or mixtures thereof. In preferred embodiments, the cationic lipid of Formula III is DLin-K-C2-DMA (XTC2).

The cationic lipid typically comprises from about 50 mol % to about 90 mol %, from about 50 mol % to about 85 mol %, from about 50 mol % to about 80 mol %, from about 50 mol % to about 75 mol %, from about 50 mol % to about 70 mol %, from about 50 mol % to about 65 mol %, or from about 55 mol % to about 65 mol % of the total lipid present in the particle.

It will be readily apparent to one of skill in the art that depending on the intended use of the particles, the proportions of the components can be varied and the delivery efficiency of a particular formulation can be measured using, e.g., an endosomal release parameter (ERP) assay.

B. Non-Cationic Lipids

The non-cationic lipids used in the lipid particles of the invention (e.g., SNALP) can be any of a variety of neutral uncharged, zwitterionic, or anionic lipids capable of producing a stable complex.

Non-limiting examples of non-cationic lipids include phospholipids such as lecithin, phosphatidylethanolamine, lysolecithin, lysophosphatidylethanolamine, phosphatidylserine, phosphatidylinositol, sphingomyelin, egg sphingomyelin (ESM), cephalin, cardiolipin, phosphatidic acid, cerebrosides, dicetylphosphate, distearoylphosphatidylcholine (DSPC), dioleoylphosphatidylcholine (DOPC), dipalmitoylphosphatidylcholine (DPPC), dioleoylphosphatidylglycerol (DOPG), dipalmitoylphosphatidylglycerol (DPPG), dioleoylphosphatidylethanolamine (DOPE), palmitoyloleoyl-phosphatidylcholine (POPC), palmitoyloleoyl-phosphatidylethanolamine (POPE), palmitoyloleyol-phosphatidylglycerol (POPG), dioleoylphosphatidylethanolamine 4-(N-maleimidomethyl)-cyclohexane-1-carboxylate (DOPE-mal), dipalmitoyl-phosphatidylethanolamine (DPPE), dimyristoyl-phosphatidylethanolamine (DMPE), distearoyl-phosphatidylethanolamine (DSPE), monomethyl-phosphatidylethanolamine, dimethyl-phosphatidylethanolamine, dielaidoyl-phosphatidylethanolamine (DEPE), stearoyloleoyl-phosphatidylethanolamine (SOPE), lysophosphatidylcholine, dilinoleoylphosphatidylcholine, and mixtures thereof. Other diacylphosphatidylcholine and diacylphosphatidylethanolamine phospholipids can also be used. The acyl groups in these lipids are preferably acyl groups derived from fatty acids having $C_{10}$-$C_{24}$ carbon chains, e.g., lauroyl, myristoyl, palmitoyl, stearoyl, or oleoyl.

Additional examples of non-cationic lipids include sterols such as cholesterol and derivatives thereof such as cholestanol, cholestanone, cholestenone, coprostanol, cholesteryl-2'-hydroxyethyl ether, cholesteryl-4'-hydroxybutyl ether, and mixtures thereof.

In some embodiments, the non-cationic lipid present in the lipid particles (e.g., SNALP) comprises or consists of cholesterol or a derivative thereof, e.g., a phospholipid-free lipid particle formulation. In other embodiments, the non-cationic lipid present in the lipid particles (e.g., SNALP) comprises or consists of one or more phospholipids, e.g., a cholesterol-free lipid particle formulation. In further embodiments, the non-cationic lipid present in the lipid particles (e.g., SNALP) comprises or consists of a mixture of one or more phospholipids and cholesterol or a derivative thereof.

Other examples of non-cationic lipids suitable for use in the present invention include nonphosphorous containing lipids such as, e.g., stearylamine, dodecylamine, hexadecylamine, acetyl palmitate, glycerolricinoleate, hexadecyl stearate, isopropyl myristate, amphoteric acrylic polymers, triethanolamine-lauryl sulfate, alkyl-aryl sulfate polyethyloxylated fatty acid amides, dioctadecyldimethyl ammonium bromide, ceramide, sphingomyelin, and the like.

In some embodiments, the non-cationic lipid comprises from about 13 mol % to about 49.5 mol %, from about 20 mol % to about 45 mol %, from about 25 mol % to about 45 mol %, from about 30 mol % to about 45 mol %, from about 35 mol % to about 45 mol %, from about 20 mol % to about 40 mol %, from about 25 mol % to about 40 mol %, or from about 30 mol % to about 40 mol % of the total lipid present in the particle.

In certain embodiments, the cholesterol present in phospholipid-free lipid particles comprises from about 30 mol % to about 45 mol %, from about 30 mol % to about 40 mol %, from about 35 mol % to about 45 mol %, or from about 35 mol % to about 40 mol % of the total lipid present in the particle. As a non-limiting example, a phospholipid-free lipid particle may comprise cholesterol at about 37 mol % of the total lipid present in the particle.

In certain other embodiments, the cholesterol present in lipid particles containing a mixture of phospholipid and cholesterol comprises from about 30 mol % to about 40 mol %, from about 30 mol % to about 35 mol %, or from about 35 mol % to about 40 mol % of the total lipid present in the particle. As a non-limiting example, a lipid particle comprising a mixture of phospholipid and cholesterol may comprise cholesterol at about 34 mol % of the total lipid present in the particle.

In further embodiments, the cholesterol present in lipid particles containing a mixture of phospholipid and cholesterol comprises from about 10 mol % to about 30 mol %, from about 15 mol % to about 25 mol %, or from about 17 mol % to about 23 mol % of the total lipid present in the particle. As a non-limiting example, a lipid particle comprising a mixture of phospholipid and cholesterol may comprise cholesterol at about 20 mol % of the total lipid present in the particle.

In embodiments where the lipid particles contain a mixture of phospholipid and cholesterol or a cholesterol derivative, the mixture may comprise up to about 40, 45, 50, 55, or 60 mol % of the total lipid present in the particle. In certain instances, the phospholipid component in the mixture may comprise from about 2 mol % to about 12 mol %, from about 4 mol % to about 10 mol %, from about 5 mol % to about 10 mol %, from about 5 mol % to about 9 mol %, or from about 6 mol % to about 8 mol % of the total lipid present in the particle. As a non-limiting example, a lipid particle comprising a mixture of phospholipid and cholesterol may comprise a phospholipid such as DPPC or DSPC at about 7 mol % (e.g., in a mixture with about 34 mol % cholesterol) of the total lipid present in the particle. In certain other instances, the phospholipid component in the mixture may comprise from about 10 mol % to about 30 mol %, from about 15 mol % to about 25 mol %, or from about 17 mol % to about 23 mol % of the total lipid present in the particle. As another non-limiting example, a lipid particle comprising a mixture of phospholipid and cholesterol may comprise a phospholipid such as DPPC or DSPC at about 20 mol % (e.g., in a mixture with about 20 mol % cholesterol) of the total lipid present in the particle.

C. Lipid Conjugate

In addition to cationic and non-cationic lipids, the lipid particles of the invention (e.g., SNALP) comprise a lipid conjugate. The conjugated lipid is useful in that it prevents the aggregation of particles. Suitable conjugated lipids include, but are not limited to, PEG-lipid conjugates, ATTA-lipid conjugates, cationic-polymer-lipid conjugates (CPLs), and mixtures thereof. In certain embodiments, the particles comprise either a PEG-lipid conjugate or an ATTA-lipid conjugate together with a CPL.

In a preferred embodiment, the lipid conjugate is a PEG-lipid. Examples of PEG-lipids include, but are not limited to, PEG coupled to dialkyloxypropyls (PEG-DAA) as described in, e.g., PCT Publication No. WO 05/026372, PEG coupled to diacylglycerol (PEG-DAG) as described in, e.g., U.S. Patent Publication Nos. 20030077829 and 2005008689, PEG coupled to phospholipids such as phosphatidylethanolamine (PEG-PE), PEG conjugated to ceramides as described in, e.g., U.S. Pat. No. 5,885,613, PEG conjugated to cholesterol or a derivative thereof, and mixtures thereof. The disclosures of these patent documents are herein incorporated by reference in their entirety for all purposes. Additional PEG-lipids include, without limitation, PEG-C-DOMG, 2 KPEG-DMG, and a mixture thereof.

PEG is a linear, water-soluble polymer of ethylene PEG repeating units with two terminal hydroxyl groups. PEGs are classified by their molecular weights; for example, PEG 2000 has an average molecular weight of about 2,000 daltons, and PEG 5000 has an average molecular weight of about 5,000 daltons. PEGs are commercially available from Sigma Chemical Co. and other companies and include, for example, the following: monomethoxypolyethylene glycol (MePEG-OH), monomethoxypolyethylene glycol-succinate (MePEG-S), monomethoxypolyethylene glycol-succinimidyl succinate (MePEG-S-NHS), monomethoxypolyethylene glycol-amine (MePEG-$NH_2$), monomethoxypolyethylene glycol-tresylate (MePEG-TRES), and monomethoxypolyethylene glycol-imidazolyl-carbonyl (MePEG-IM). Other PEGs such as those described in U.S. Pat. Nos. 6,774,180 and 7,053,150 (e.g., mPEG (20 KDa) amine) are also useful for preparing the PEG-lipid conjugates of the present invention. The disclosures of these patents are herein incorporated by reference in their entirety for all purposes. In addition, monomethoxypolyethyleneglycol-acetic acid (MePEG-$CH_2$COOH) is particularly useful for preparing PEG-lipid conjugates including, e.g., PEG-DAA conjugates.

The PEG moiety of the PEG-lipid conjugates described herein may comprise an average molecular weight ranging from about 550 daltons to about 10,000 daltons. In certain instances, the PEG moiety has an average molecular weight of from about 750 daltons to about 5,000 daltons (e.g., from about 1,000 daltons to about 5,000 daltons, from about 1,500 daltons to about 3,000 daltons, from about 750 daltons to about 3,000 daltons, from about 750 daltons to about 2,000 daltons, etc.). In preferred embodiments, the PEG moiety has an average molecular weight of about 2,000 daltons or about 750 daltons.

In certain instances, the PEG can be optionally substituted by an alkyl, alkoxy, acyl, or aryl group. The PEG can be conjugated directly to the lipid or may be linked to the lipid via a linker moiety. Any linker moiety suitable for coupling the PEG to a lipid can be used including, e.g., non-ester containing linker moieties and ester-containing linker moieties. In a preferred embodiment, the linker moiety is a non-ester containing linker moiety. As used herein, the term "non-ester containing linker moiety" refers to a linker moiety that does not contain a carboxylic ester bond (—OC(O)—). Suitable non-ester containing linker moieties include, but are not limited to, amido (—C(O)NH—), amino (—NR—), carbonyl (—C(O)—), carbamate (—NHC(O)O—), urea (—NHC(O)NH—), disulphide (—S—S—), ether (—O—), succinyl (—(O)CCH$_2$CH$_2$C(O)—), succinamidyl (—NHC(O)CH$_2$CH$_2$C(O)NH—), ether, disulphide, as well as combinations thereof (such as a linker containing both a carbamate linker moiety and an amido linker moiety). In a preferred embodiment, a carbamate linker is used to couple the PEG to the lipid.

In other embodiments, an ester containing linker moiety is used to couple the PEG to the lipid. Suitable ester containing linker moieties include, e.g., carbonate (—OC(O)O—), succinoyl, phosphate esters (—O—(O)POH—O—), sulfonate esters, and combinations thereof.

Phosphatidylethanolamines having a variety of acyl chain groups of varying chain lengths and degrees of saturation can be conjugated to PEG to form the lipid conjugate. Such phosphatidylethanolamines are commercially available, or can be isolated or synthesized using conventional techniques known to those of skilled in the art. Phosphatidyl-ethanolamines containing saturated or unsaturated fatty acids with carbon chain lengths in the range of $C_{10}$ to $C_{20}$ are preferred. Phosphatidylethanolamines with mono- or diunsaturated fatty acids and mixtures of saturated and unsaturated fatty acids can also be used. Suitable phosphatidylethanolamines include, but are not limited to, dimyristoyl-phosphatidylethanolamine (DMPE), dipalmitoyl-phosphatidylethanolamine (DPPE), dioleoylphosphatidylethanolamine (DOPE), and distearoyl-phosphatidylethanolamine (DSPE).

The term "ATTA" or "polyamide" refers to, without limitation, compounds described in U.S. Pat. Nos. 6,320,017 and 6,586,559, the disclosures of which are herein incorporated by reference in their entirety for all purposes. These compounds include a compound having the formula:

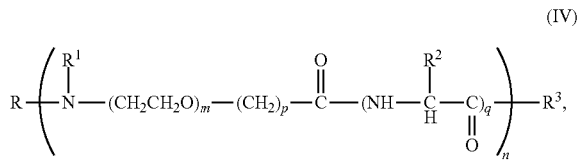

(IV)

wherein R is a member selected from the group consisting of hydrogen, alkyl and acyl; R' is a member selected from the group consisting of hydrogen and alkyl; or optionally, R and $R^1$ and the nitrogen to which they are bound form an azido moiety; $R^2$ is a member of the group selected from hydrogen, optionally substituted alkyl, optionally substituted aryl and a side chain of an amino acid; $R^3$ is a member selected from the group consisting of hydrogen, halogen, hydroxy, alkoxy, mercapto, hydrazino, amino and $NR^4R^5$, wherein $R^4$ and $R^5$ are independently hydrogen or alkyl; n is 4 to 80; m is 2 to 6; p is 1 to 4; and q is 0 or 1. It will be apparent to those of skill in the art that other polyamides can be used in the compounds of the present invention.

The term "diacylglycerol" refers to a compound having 2 fatty acyl chains, R' and $R^2$, both of which have independently between 2 and 30 carbons bonded to the 1- and 2-position of glycerol by ester linkages. The acyl groups can be saturated or have varying degrees of unsaturation. Suitable acyl groups include, but are not limited to, lauryl ($C_{12}$), myristyl ($C_{14}$), palmityl ($C_{16}$), stearyl ($C_{18}$), and icosyl ($C_{20}$). In preferred embodiments, $R^1$ and $R^2$ are the same, i.e., $R^1$ and $R^2$ are both myristyl (i.e., dimyristyl), $R^1$ and $R^2$ are both stearyl (i.e., distearyl), etc. Diacylglycerols have the following general formula:

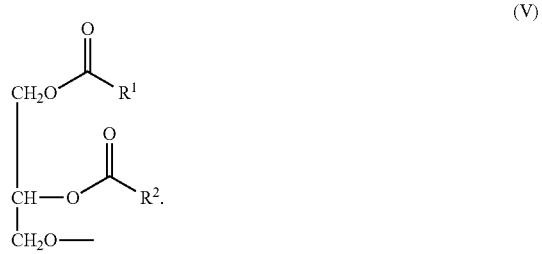

(V)

The term "dialkyloxypropyl" refers to a compound having 2 alkyl chains, $R^1$ and $R^2$, both of which have independently between 2 and 30 carbons. The alkyl groups can be saturated or have varying degrees of unsaturation. Dialkyloxypropyls have the following general formula:

(VI)

In a preferred embodiment, the PEG-lipid is a PEG-DAA conjugate having the following formula:

(VII)

wherein $R^1$ and $R^2$ are independently selected and are long-chain alkyl groups having from about 10 to about 22 carbon atoms; PEG is a polyethyleneglycol; and L is a non-ester containing linker moiety or an ester containing linker moiety as described above. The long-chain alkyl groups can be saturated or unsaturated. Suitable alkyl groups include, but are not limited to, lauryl ($C_{12}$), myristyl ($C_{14}$), palmityl ($C_{16}$), stearyl ($C_{18}$), and icosyl ($C_{20}$). In preferred embodiments, $R^1$ and $R^2$ are the same, i.e., $R^1$ and $R^2$ are both myristyl (i.e., dimyristyl), $R^1$ and $R^2$ are both stearyl (i.e., distearyl), etc.

In Formula VII above, the PEG has an average molecular weight ranging from about 550 daltons to about 10,000 daltons. In certain instances, the PEG has an average molecular weight of from about 750 daltons to about 5,000 daltons (e.g., from about 1,000 daltons to about 5,000 daltons, from about 1,500 daltons to about 3,000 daltons, from about 750 daltons to about 3,000 daltons, from about 750 daltons to about 2,000 daltons, etc.). In preferred embodiments, the PEG has an average molecular weight of about 2,000 daltons or about 750 daltons. The PEG can be optionally substituted with alkyl, alkoxy, acyl, or aryl. In certain embodiments, the terminal hydroxyl group is substituted with a methoxy or methyl group.

In a preferred embodiment, "L" is a non-ester containing linker moiety. Suitable non-ester containing linkers include, but are not limited to, an amido linker moiety, an amino linker moiety, a carbonyl linker moiety, a carbamate linker moiety, a urea linker moiety, an ether linker moiety, a disulphide linker moiety, a succinamidyl linker moiety, and combinations thereof. In a preferred embodiment, the non-ester containing linker moiety is a carbamate linker moiety (i.e., a PEG-C-DAA conjugate). In another preferred embodiment, the non-ester containing linker moiety is an amido linker moiety (i.e., a PEG-A-DAA conjugate). In yet another preferred embodiment, the non-ester containing linker moiety is a succinamidyl linker moiety (i.e., a PEG-S-DAA conjugate).

In particular embodiments, the PEG-lipid conjugate is selected from:

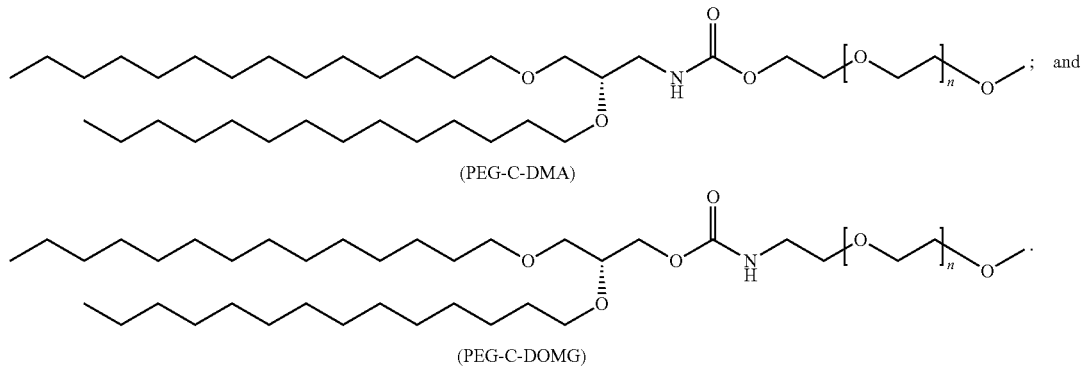

(PEG-C-DMA)

(PEG-C-DOMG)

The PEG-DAA conjugates are synthesized using standard techniques and reagents known to those of skill in the art. It will be recognized that the PEG-DAA conjugates will contain various amide, amine, ether, thio, carbamate, and urea linkages. Those of skill in the art will recognize that methods and reagents for forming these bonds are well known and readily available. See, e.g., March, ADVANCED ORGANIC CHEMISTRY (Wiley 1992); Larock, COMPREHENSIVE ORGANIC TRANSFORMATIONS (VCH 1989); and Furniss, VOGEL'S TEXTBOOK OF PRACTICAL ORGANIC CHEMISTRY, 5th ed. (Longman 1989). It will also be appreciated that any functional groups present may require protection and deprotection at different points in the synthesis of the PEG-DAA conjugates. Those of skill in the art will recognize that such techniques are well known. See, e.g., Green and Wuts, PROTECTIVE GROUPS IN ORGANIC SYNTHESIS (Wiley 1991).

Preferably, the PEG-DAA conjugate is a dilauryloxypropyl ($C_{12}$)-PEG conjugate, dimyristyloxypropyl ($C_{14}$)-PEG conjugate, a dipalmityloxypropyl ($C_{16}$)-PEG conjugate, or a distearyloxypropyl ($C_{18}$)-PEG conjugate. Those of skill in the art will readily appreciate that other dialkyloxypropyls can be used in the PEG-DAA conjugates of the present invention.

In addition to the foregoing, it will be readily apparent to those of skill in the art that other hydrophilic polymers can be used in place of PEG. Examples of suitable polymers that can be used in place of PEG include, but are not limited to, polyvinylpyrrolidone, polymethyloxazoline, polyethyloxazoline, polyhydroxypropyl methacrylamide, polymethacrylamide and polydimethylacrylamide, polylactic acid, polyglycolic acid, and derivatized celluloses such as hydroxymethylcellulose or hydroxyethylcellulose.

In addition to the foregoing components, the particles (e.g., SNALP or SPLP) of the present invention can further comprise cationic poly(ethylene glycol) (PEG) lipids or CPLs (see, e.g., Chen et al., *Bioconj. Chem.*, 11:433-437 (2000)). Suitable SPLPs and SPLP-CPLs for use in the present invention, and methods of making and using SPLPs and SPLP-CPLs, are disclosed, e.g., in U.S. Pat. No. 6,852,334 and PCT Publication No. WO 00/62813, the disclosures of which are herein incorporated by reference in their entirety for all purposes.

Suitable CPLs include compounds of Formula VIII:

A-W-Y  (VIII), wherein A, W, and Y are as described below.

With reference to Formula VIII, "A" is a lipid moiety such as an amphipathic lipid, a neutral lipid, or a hydrophobic lipid that acts as a lipid anchor. Suitable lipid examples include, but are not limited to, diacylglycerolyls, dialkylglycerolyls, N-N-dialkylaminos, 1,2-diacyloxy-3-aminopropanes, and 1,2-dialkyl-3-aminopropanes.

"W" is a polymer or an oligomer such as a hydrophilic polymer or oligomer. Preferably, the hydrophilic polymer is a biocompatible polymer that is nonimmunogenic or possesses low inherent immunogenicity. Alternatively, the hydrophilic polymer can be weakly antigenic if used with appropriate adjuvants. Suitable nonimmunogenic polymers include, but are not limited to, PEG, polyamides, polylactic acid, polyglycolic acid, polylactic acid/polyglycolic acid copolymers, and combinations thereof. In a preferred embodiment, the polymer has a molecular weight of from about 250 to about 7,000 daltons.

"Y" is a polycationic moiety. The term polycationic moiety refers to a compound, derivative, or functional group having a positive charge, preferably at least 2 positive charges at a selected pH, preferably physiological pH. Suitable polycationic moieties include basic amino acids and their derivatives such as arginine, asparagine, glutamine, lysine, and histidine; spermine; spermidine; cationic dendrimers; polyamines; polyamine sugars; and amino polysaccharides. The polycationic moieties can be linear, such as linear tetralysine, branched or dendrimeric in structure. Polycationic moieties have between about 2 to about 15 positive charges, preferably between about 2 to about 12 positive charges, and more preferably between about 2 to about 8 positive charges at selected pH values. The selection of which polycationic moiety to employ may be determined by the type of particle application which is desired.

The charges on the polycationic moieties can be either distributed around the entire particle moiety, or alternatively, they can be a discrete concentration of charge density in one particular area of the particle moiety e.g., a charge spike. If the charge density is distributed on the particle, the charge density can be equally distributed or unequally distributed. All variations of charge distribution of the polycationic moiety are encompassed by the present invention.

The lipid "A" and the nonimmunogenic polymer "W" can be attached by various methods and preferably by covalent attachment. Methods known to those of skill in the art can be used for the covalent attachment of "A" and "W." Suitable linkages include, but are not limited to, amide, amine, carboxyl, carbonate, carbamate, ester, and hydrazone linkages. It will be apparent to those skilled in the art that "A" and "W" must have complementary functional groups to effectuate the linkage. The reaction of these two groups, one on the lipid and the other on the polymer, will provide the desired linkage. For example, when the lipid is a diacylglycerol and the terminal hydroxyl is activated, for instance with NHS and DCC, to form an active ester, and is then reacted with a polymer which contains an amino group, such as with a polyamide (see, e.g., U.S. Pat. Nos. 6,320,017 and 6,586,559, the disclosures of which are herein incorporated by reference in their entirety for all purposes), an amide bond will form between the two groups.

In certain instances, the polycationic moiety can have a ligand attached, such as a targeting ligand or a chelating moiety for complexing calcium. Preferably, after the ligand is attached, the cationic moiety maintains a positive charge. In certain instances, the ligand that is attached has a positive charge. Suitable ligands include, but are not limited to, a compound or device with a reactive functional group and include lipids, amphipathic lipids, carrier compounds, bioaffinity compounds, biomaterials, biopolymers, biomedical devices, analytically detectable compounds, therapeutically active compounds, enzymes, peptides, proteins, antibodies, immune stimulators, radiolabels, fluorogens, biotin, drugs, haptens, DNA, RNA, polysaccharides, liposomes, virosomes, micelles, immunoglobulins, functional groups, other targeting moieties, or toxins.

The lipid conjugate (e.g., PEG-lipid) typically comprises from about 0.1 mol % to about 2 mol %, from about 0.5 mol % to about 2 mol %, from about 1 mol % to about 2 mol %, from about 0.6 mol % to about 1.9 mol %, from about 0.7 mol % to about 1.8 mol %, from about 0.8 mol % to about 1.7 mol %, from about 0.9 mol % to about 1.6 mol %, from about 0.9 mol % to about 1.8 mol %, from about 1 mol % to about 1.8 mol %, from about 1 mol % to about 1.7 mol %, from about 1.2 mol % to about 1.8 mol %, from about 1.2 mol % to about 1.7 mol %, from about 1.3 mol % to about 1.6 mol %, or from about 1.4 mol % to about 1.5 mol % of the total lipid present in the particle.

One of ordinary skill in the art will appreciate that the concentration of the lipid conjugate can be varied depending on the lipid conjugate employed and the rate at which the nucleic acid-lipid particle is to become fusogenic.

By controlling the composition and concentration of the lipid conjugate, one can control the rate at which the lipid conjugate exchanges out of the nucleic acid-lipid particle and, in turn, the rate at which the nucleic acid-lipid particle becomes fusogenic. For instance, when a PEG-phosphatidylethanolamine conjugate or a PEG-ceramide conjugate is used as the lipid conjugate, the rate at which the nucleic acid-lipid particle becomes fusogenic can be varied, for example, by varying the concentration of the lipid conjugate, by varying the molecular weight of the PEG, or by varying the chain length and degree of saturation of the acyl chain groups on the phosphatidylethanolamine or the ceramide. In addition, other variables including, for example, pH, temperature, ionic strength, etc. can be used to vary and/or control the rate at which the nucleic acid-lipid particle becomes fusogenic. Other methods which can be used to control the rate at which the nucleic acid-lipid particle becomes fusogenic will become apparent to those of skill in the art upon reading this disclosure.

VI. Preparation of Lipid Particles

The lipid particles of the present invention, e.g., SNALP, in which an active agent or therapeutic agent such as an interfering RNA is encapsulated in a lipid bilayer and is protected from degradation, can be formed by any method known in the art including, but not limited to, a continuous mixing method or a direct dilution process.

In preferred embodiments, the cationic lipids are lipids of Formula I, II, and III, or combinations thereof. In other preferred embodiments, the non-cationic lipids are egg sphingomyelin (ESM), distearoylphosphatidylcholine (DSPC), dioleoylphosphatidylcholine (DOPC), 1-palmitoyl-2-oleoyl-phosphatidylcholine (POPC), dipalmitoyl-phosphatidylcholine (DPPC), monomethyl-phosphatidylethanolamine, dimethyl-phosphatidylethanolamine, 14:0 PE (1,2-dimyristoyl-phosphatidylethanolamine (DMPE)), 16:0 PE (1,2-dipalmitoyl-phosphatidylethanolamine (DPPE)), 18:0 PE (1,2-distearoyl-phosphatidylethanolamine (DSPE)), 18:1 PE (1,2-dioleoyl-phosphatidylethanolamine (DOPE)), 18:1 trans PE (1,2-dielaidoyl-phosphatidylethanolamine (DEPE)), 18:0-18:1 PE (1-stearoyl-2-oleoyl-phosphatidylethanolamine (SOPE)), 16:0-18:1 PE (1-palmitoyl-2-oleoyl-phosphatidylethanolamine (POPE)), polyethylene glycol-based polymers (e.g., PEG 2000, PEG 5000, PEG-modified diacylglycerols, or PEG-modified dialkyloxypropyls), cholesterol, or combinations thereof.

In certain embodiments, the present invention provides for SNALP produced via a continuous mixing method, e.g., a process that includes providing an aqueous solution comprising a nucleic acid such as an interfering RNA in a first reservoir, providing an organic lipid solution in a second reservoir, and mixing the aqueous solution with the organic lipid solution such that the organic lipid solution mixes with the aqueous solution so as to substantially instantaneously produce a liposome encapsulating the nucleic acid (e.g., interfering RNA). This process and the apparatus for carrying this process are described in detail in U.S. Patent Publication No. 20040142025, the disclosure of which is herein incorporated by reference in its entirety for all purposes.

The action of continuously introducing lipid and buffer solutions into a mixing environment, such as in a mixing chamber, causes a continuous dilution of the lipid solution with the buffer solution, thereby producing a liposome substantially instantaneously upon mixing. As used herein, the phrase "continuously diluting a lipid solution with a buffer solution" (and variations) generally means that the lipid solution is diluted sufficiently rapidly in a hydration process with sufficient force to effectuate vesicle generation. By mixing the aqueous solution comprising a nucleic acid with the organic lipid solution, the organic lipid solution undergoes a continuous stepwise dilution in the presence of the buffer solution (i.e., aqueous solution) to produce a nucleic acid-lipid particle.

The SNALP formed using the continuous mixing method typically have a size of from about 40 nm to about 150 nm, from about 50 nm to about 150 nm, from about 60 nm to about 130 nm, from about 70 nm to about 110 nm, or from about 70 nm to about 90 nm. The particles thus formed do not aggregate and are optionally sized to achieve a uniform particle size.

In another embodiment, the present invention provides for SNALP produced via a direct dilution process that includes forming a liposome solution and immediately and directly introducing the liposome solution into a collection vessel containing a controlled amount of dilution buffer. In preferred aspects, the collection vessel includes one or more elements configured to stir the contents of the collection vessel to facilitate dilution. In one aspect, the amount of dilution buffer present in the collection vessel is substantially equal to the volume of liposome solution introduced thereto. As a non-limiting example, a liposome solution in 45% ethanol when introduced into the collection vessel containing an equal volume of dilution buffer will advantageously yield smaller particles.

In yet another embodiment, the present invention provides for SNALP produced via a direct dilution process in which a third reservoir containing dilution buffer is fluidly coupled to a second mixing region. In this embodiment, the liposome solution formed in a first mixing region is immediately and directly mixed with dilution buffer in the second mixing region. In preferred aspects, the second mixing region includes a T-connector arranged so that the liposome solution and the dilution buffer flows meet as opposing 180° flows; however, connectors providing shallower angles can be used, e.g., from about 27° to about 180°. A pump mechanism delivers a controllable flow of buffer to the second mixing region. In one aspect, the flow rate of dilution buffer provided to the second mixing region is controlled to be substantially equal to the flow rate of liposome solution introduced thereto from the first mixing region. This embodiment advantageously allows for more control of the flow of dilution buffer mixing with the liposome solution in the second mixing region, and therefore also the concentration of liposome solution in buffer throughout the second mixing process. Such control of the dilution buffer flow rate advantageously allows for small particle size formation at reduced concentrations.

These processes and the apparatuses for carrying out these direct dilution processes are described in detail in U.S. Patent Publication No. 20070042031, the disclosure of which is herein incorporated by reference in its entirety for all purposes.

The SNALP formed using the direct dilution process typically have a size of from about 40 nm to about 150 nm, from about 50 nm to about 150 nm, from about 60 nm to about 130 nm, from about 70 nm to about 110 nm, or from about 70 nm to about 90 nm. The particles thus formed do not aggregate and are optionally sized to achieve a uniform particle size.

If needed, the lipid particles of the invention (e.g., SNALP) can be sized by any of the methods available for sizing liposomes. The sizing may be conducted in order to achieve a desired size range and relatively narrow distribution of particle sizes.

Several techniques are available for sizing the particles to a desired size. One sizing method, used for liposomes and equally applicable to the present particles, is described in U.S. Pat. No. 4,737,323, the disclosure of which is herein incorporated by reference in its entirety for all purposes. Sonicating a particle suspension either by bath or probe sonication produces a progressive size reduction down to particles of less than about 50 nm in size. Homogenization is another method which relies on shearing energy to fragment larger particles into smaller ones. In a typical homogenization procedure, particles are recirculated through a standard emulsion homogenizer until selected particle sizes, typically between about 60 and about 80 nm, are observed. In both methods, the particle size distribution can be monitored by conventional laser-beam particle size discrimination, or QELS.

Extrusion of the particles through a small-pore polycarbonate membrane or an asymmetric ceramic membrane is also an effective method for reducing particle sizes to a relatively well-defined size distribution. Typically, the suspension is cycled through the membrane one or more times until the desired particle size distribution is achieved. The particles may be extruded through successively smaller-pore membranes, to achieve a gradual reduction in size.

In some embodiments, the nucleic acids in the SNALP are precondensed as described in, e.g., U.S. patent application Ser. No. 09/744,103, the disclosure of which is herein incorporated by reference in its entirety for all purposes.

In other embodiments, the methods will further comprise adding non-lipid polycations which are useful to effect the lipofection of cells using the present compositions. Examples of suitable non-lipid polycations include, hexadimethrine bromide (sold under the brandname POLYBRENE®, from Aldrich Chemical Co., Milwaukee, Wis., USA) or other salts of hexadimethrine. Other suitable polycations include, for example, salts of poly-L-ornithine, poly-L-arginine, poly-L-lysine, poly-D-lysine, polyallylamine, and polyethyleneimine. Addition of these salts is preferably after the particles have been formed.

In some embodiments, the nucleic acid to lipid ratios (mass/mass ratios) in a formed SNALP will range from about 0.01 to about 0.2, from about 0.02 to about 0.1, from about 0.03 to about 0.1, or from about 0.01 to about 0.08. The ratio of the starting materials also falls within this range. In other embodiments, the SNALP preparation uses about 400 μg nucleic acid per 10 mg total lipid or a nucleic acid to lipid mass ratio of about 0.01 to about 0.08 and, more preferably, about 0.04, which corresponds to 1.25 mg of total lipid per 50 μg of nucleic acid. In other preferred embodiments, the particle has a nucleic acid:lipid mass ratio of about 0.08.

In other embodiments, the lipid to nucleic acid ratios (mass/mass ratios) in a formed SNALP will range from about 1 (1:1) to about 100 (100:1), from about 5 (5:1) to about 100 (100:1), from about 1 (1:1) to about 50 (50:1), from about 2 (2:1) to about 50 (50:1), from about 3 (3:1) to about 50 (50:1), from about 4 (4:1) to about 50 (50:1), from about 5 (5:1) to about 50 (50:1), from about 1 (1:1) to about 25 (25:1), from about 2 (2:1) to about 25 (25:1), from about 3 (3:1) to about 25 (25:1), from about 4 (4:1) to about 25 (25:1), from about 5 (5:1) to about 25 (25:1), from about 5 (5:1) to about 20 (20:1), from about 5 (5:1) to about 15 (15:1), from about 5 (5:1) to about 10 (10:1), about 5 (5:1), 6 (6:1), 7 (7:1), 8 (8:1), 9 (9:1), (10:1), 11 (11:1), 12 (12:1), 13 (13:1), 14 (14:1), or 15 (15:1). The ratio of the starting materials also falls within this range.

As previously discussed, the conjugated lipid may further include a CPL. A variety of general methods for making SNALP-CPLs (CPL-containing SNALP) are discussed herein. Two general techniques include "post-insertion" technique, that is, insertion of a CPL into, for example, a preformed SNALP, and the "standard" technique, wherein the CPL is included in the lipid mixture during, for example, the SNALP formation steps. The post-insertion technique results in SNALP having CPLs mainly in the external face of the SNALP bilayer membrane, whereas standard techniques provide SNALP having CPLs on both internal and external faces. The method is especially useful for vesicles made from phospholipids (which can contain cholesterol) and also for vesicles containing PEG-lipids (such as PEG-DAAs and PEG-DAGs). Methods of making SNALP-CPL, are taught, for example, in U.S. Pat. Nos. 5,705,385; 6,586,410; 5,981,501; 6,534,484; and 6,852,334; U.S. Patent Publication No. 20020072121; and PCT Publication No. WO 00/62813, the disclosures of which are herein incorporated by reference in their entirety for all purposes.

VII. Kits

The present invention also provides lipid particles (e.g., SNALP) in kit form. The kit may comprise a container which is compartmentalized for holding the various elements of the lipid particles (e.g., the active agents or therapeutic agents such as nucleic acids and the individual lipid components of the particles). In some embodiments, the kit may further comprise an endosomal membrane destabilizer (e.g., calcium ions). The kit typically contains the lipid particle compositions of the present invention, preferably in dehydrated form, with instructions for their rehydration and administration.

As explained herein, the lipid particles of the invention (e.g., SNALP) can be tailored to preferentially target particular tissues, organs, or tumors of interest. In certain instances, preferential targeting of lipid particles such as SNALP may be carried out by controlling the composition of the particle itself. For instance, as set forth in Example 11, it has been found that the 1:57 PEG-cDSA SNALP formulation can be used to preferentially target tumors outside of the liver, whereas the 1:57 PEG-cDMA SNALP formulation can be used to preferentially target the liver (including liver tumors).

In certain other instances, it may be desirable to have a targeting moiety attached to the surface of the lipid particle to further enhance the targeting of the particle. Methods of attaching targeting moieties (e.g., antibodies, proteins, etc.) to lipids (such as those used in the present particles) are known to those of skill in the art.

VII. Administration of Lipid Particles

Once formed, the lipid particles of the invention (e.g., SNALP) are useful for the introduction of active agents or therapeutic agents (e.g., nucleic acids such as interfering RNA) into cells. Accordingly, the present invention also provides methods for introducing an active agent or therapeutic agent such as a nucleic acid (e.g., interfering RNA) into a cell. The methods are carried out in vitro or in vivo by first forming the particles as described above and then contacting the particles with the cells for a period of time sufficient for delivery of the active agent or therapeutic agent to the cells to occur.

The lipid particles of the invention (e.g., SNALP) can be adsorbed to almost any cell type with which they are mixed or contacted. Once adsorbed, the particles can either be endocytosed by a portion of the cells, exchange lipids with cell membranes, or fuse with the cells. Transfer or incorporation of the active agent or therapeutic agent (e.g., nucleic acid) portion of the particle can take place via any one of these pathways. In particular, when fusion takes place, the particle membrane is integrated into the cell membrane and the contents of the particle combine with the intracellular fluid.

The lipid particles of the invention (e.g., SNALP) can be administered either alone or in a mixture with a pharmaceutically-acceptable carrier (e.g., physiological saline or phosphate buffer) selected in accordance with the route of administration and standard pharmaceutical practice. Generally, normal buffered saline (e.g., 135-150 mM NaCl) will be employed as the pharmaceutically-acceptable carrier. Other suitable carriers include, e.g., water, buffered water, 0.4% saline, 0.3% glycine, and the like, including glycoproteins for enhanced stability, such as albumin, lipoprotein, globulin, etc. Additional suitable carriers are described in, e.g., REMINGTON'S PHARMACEUTICAL SCIENCES, Mack Publishing Company, Philadelphia, Pa., 17th ed. (1985). As used herein, "carrier" includes any and all solvents, dispersion media, vehicles, coatings, diluents, antibacterial and antifungal agents, isotonic and absorption delaying agents, buffers, carrier solutions, suspensions, colloids, and the like. The phrase "pharmaceutically-acceptable" refers to molecular entities and compositions that do not produce an allergic or similar untoward reaction when administered to a human.

The pharmaceutically-acceptable carrier is generally added following particle formation. Thus, after the particle is formed, the particle can be diluted into pharmaceutically-acceptable carriers such as normal buffered saline.

The concentration of particles in the pharmaceutical formulations can vary widely, i.e., from less than about 0.05%, usually at or at least about 2 to 5%, to as much as about 10 to 90% by weight, and will be selected primarily by fluid volumes, viscosities, etc., in accordance with the particular mode of administration selected. For example, the concentration may be increased to lower the fluid load associated with treatment. This may be particularly desirable in patients having atherosclerosis-associated congestive heart failure or severe hypertension. Alternatively, particles composed of irritating lipids may be diluted to low concentrations to lessen inflammation at the site of administration.

The pharmaceutical compositions of the present invention may be sterilized by conventional, well-known sterilization techniques. Aqueous solutions can be packaged for use or filtered under aseptic conditions and lyophilized, the lyophilized preparation being combined with a sterile aqueous solution prior to administration. The compositions can contain pharmaceutically-acceptable auxiliary substances as required to approximate physiological conditions, such as pH adjusting and buffering agents, tonicity adjusting agents and the like, for example, sodium acetate, sodium lactate, sodium chloride, potassium chloride, and calcium chloride. Additionally, the particle suspension may include lipid-protective agents which protect lipids against free-radical and lipid-peroxidative damages on storage. Lipophilic free-radical quenchers, such as alphatocopherol and water-soluble iron-specific chelators, such as ferrioxamine, are suitable.

A. In Vivo Administration

Systemic delivery for in vivo therapy, e.g., delivery of a therapeutic nucleic acid to a distal target cell via body systems such as the circulation, has been achieved using nucleic acid-lipid particles such as those described in PCT Publication Nos. WO 05/007196, WO 05/121348, WO 05/120152, and WO 04/002453, the disclosures of which are herein incorporated by reference in their entirety for all purposes. The present invention also provides fully encapsulated lipid particles that protect the nucleic acid from nuclease degradation in serum, are nonimmunogenic, are small in size, and are suitable for repeat dosing.

For in vivo administration, administration can be in any manner known in the art, e.g., by injection, oral administration, inhalation (e.g., intranasal or intratracheal), transdermal application, or rectal administration. Administration can be accomplished via single or divided doses. The pharmaceutical compositions can be administered parenterally, i.e., intraarticularly, intravenously, intraperitoneally, subcutaneously, or intramuscularly. In some embodiments, the pharmaceutical compositions are administered intravenously or intraperitoneally by a bolus injection (see, e.g., U.S. Pat. No. 5,286,634). Intracellular nucleic acid delivery has also been discussed in Straubringer et al., *Methods Enzymol.,* 101:512 (1983); Mannino et al., *Biotechniques,* 6:682 (1988); Nicolau et al., *Crit. Rev. Ther. Drug Carrier Syst.,* 6:239 (1989); and Behr, *Acc. Chem. Res.,* 26:274 (1993). Still other methods of administering lipid-based therapeutics are described in, for example, U.S. Pat. Nos. 3,993,754; 4,145,410; 4,235,871; 4,224,179; 4,522,803; and 4,588,578. The lipid particles can be administered by direct injection at the site of disease or by injection at a site distal from the site of disease (see, e.g., Culver, HUMAN GENE THERAPY, MaryAnn Liebert, Inc., Publishers, New York. pp. 70-71 (1994)). The disclosures of the above-described references are herein incorporated by reference in their entirety for all purposes.

The compositions of the present invention, either alone or in combination with other suitable components, can be made into aerosol formulations (i.e., they can be "nebulized") to be administered via inhalation (e.g., intranasally or intratracheally) (see, Brigham et al., *Am. J. Sci.*, 298:278 (1989)). Aerosol formulations can be placed into pressurized acceptable propellants, such as dichlorodifluoromethane, propane, nitrogen, and the like.

In certain embodiments, the pharmaceutical compositions may be delivered by intranasal sprays, inhalation, and/or other aerosol delivery vehicles. Methods for delivering nucleic acid compositions directly to the lungs via nasal aerosol sprays have been described, e.g., in U.S. Pat. Nos. 5,756,353 and 5,804,212. Likewise, the delivery of drugs using intranasal microparticle resins and lysophosphatidyl-glycerol compounds (U.S. Pat. No. 5,725,871) are also well-known in the pharmaceutical arts. Similarly, transmucosal drug delivery in the form of a polytetrafluoroetheylene support matrix is described in U.S. Pat. No. 5,780,045. The disclosures of the above-described patents are herein incorporated by reference in their entirety for all purposes.

Formulations suitable for parenteral administration, such as, for example, by intraarticular (in the joints), intravenous, intramuscular, intradermal, intraperitoneal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. In the practice of this invention, compositions are preferably administered, for example, by intravenous infusion, orally, topically, intraperitoneally, intravesically, or intrathecally.

Generally, when administered intravenously, the lipid particle formulations are formulated with a suitable pharmaceutical carrier. Many pharmaceutically acceptable carriers may be employed in the compositions and methods of the present invention. Suitable formulations for use in the present invention are found, for example, in REMINGTON'S PHARMACEUTICAL SCIENCES, Mack Publishing Company, Philadelphia, Pa., 17th ed. (1985). A variety of aqueous carriers may be used, for example, water, buffered water, 0.4% saline, 0.3% glycine, and the like, and may include glycoproteins for enhanced stability, such as albumin, lipoprotein, globulin, etc. Generally, normal buffered saline (135-150 mM NaCl) will be employed as the pharmaceutically acceptable carrier, but other suitable carriers will suffice. These compositions can be sterilized by conventional liposomal sterilization techniques, such as filtration. The compositions may contain pharmaceutically acceptable auxiliary substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, triethanolamine oleate, etc. These compositions can be sterilized using the techniques referred to above or, alternatively, they can be produced under sterile conditions. The resulting aqueous solutions may be packaged for use or filtered under aseptic conditions and lyophilized, the lyophilized preparation being combined with a sterile aqueous solution prior to administration.

In certain applications, the lipid particles disclosed herein may be delivered via oral administration to the individual. The particles may be incorporated with excipients and used in the form of ingestible tablets, buccal tablets, troches, capsules, pills, lozenges, elixirs, mouthwash, suspensions, oral sprays, syrups, wafers, and the like (see, e.g., U.S. Pat. Nos. 5,641,515, 5,580,579, and 5,792,451, the disclosures of which are herein incorporated by reference in their entirety for all purposes). These oral dosage forms may also contain the following: binders, gelatin; excipients, lubricants, and/or flavoring agents. When the unit dosage form is a capsule, it may contain, in addition to the materials described above, a liquid carrier. Various other materials may be present as coatings or to otherwise modify the physical form of the dosage unit. Of course, any material used in preparing any unit dosage form should be pharmaceutically pure and substantially non-toxic in the amounts employed.

Typically, these oral formulations may contain at least about 0.1% of the lipid particles or more, although the percentage of the particles may, of course, be varied and may conveniently be between about 1% or 2% and about 60% or 70% or more of the weight or volume of the total formulation. Naturally, the amount of particles in each therapeutically useful composition may be prepared is such a way that a suitable dosage will be obtained in any given unit dose of the compound. Factors such as solubility, bioavailability, biological half-life, route of administration, product shelf life, as well as other pharmacological considerations will be contemplated by one skilled in the art of preparing such pharmaceutical formulations, and as such, a variety of dosages and treatment regimens may be desirable.

Formulations suitable for oral administration can consist of: (a) liquid solutions, such as an effective amount of a packaged therapeutic agent such as nucleic acid (e.g., interfering RNA) suspended in diluents such as water, saline, or PEG 400; (b) capsules, sachets, or tablets, each containing a predetermined amount of a therapeutic agent such as nucleic acid (e.g., interfering RNA), as liquids, solids, granules, or gelatin; (c) suspensions in an appropriate liquid; and (d) suitable emulsions. Tablet forms can include one or more of lactose, sucrose, mannitol, sorbitol, calcium phosphates, corn starch, potato starch, microcrystalline cellulose, gelatin, colloidal silicon dioxide, talc, magnesium stearate, stearic acid, and other excipients, colorants, fillers, binders, diluents, buffering agents, moistening agents, preservatives, flavoring agents, dyes, disintegrating agents, and pharmaceutically compatible carriers. Lozenge forms can comprise a therapeutic agent such as nucleic acid (e.g., interfering RNA) in a flavor, e.g., sucrose, as well as pastilles comprising the therapeutic agent in an inert base, such as gelatin and glycerin or sucrose and acacia emulsions, gels, and the like containing, in addition to the therapeutic agent, carriers known in the art.

In another example of their use, lipid particles can be incorporated into a broad range of topical dosage forms. For instance, a suspension containing nucleic acid-lipid particles such as SNALP can be formulated and administered as gels, oils, emulsions, topical creams, pastes, ointments, lotions, foams, mousses, and the like.

When preparing pharmaceutical preparations of the lipid particles of the invention, it is preferable to use quantities of the particles which have been purified to reduce or eliminate empty particles or particles with therapeutic agents such as nucleic acid associated with the external surface.

The methods of the present invention may be practiced in a variety of hosts. Preferred hosts include mammalian species, such as primates (e.g., humans and chimpanzees as well as other nonhuman primates), canines, felines, equines, bovines, ovines, caprines, rodents (e.g., rats and mice), lagomorphs, and swine.

The amount of particles administered will depend upon the ratio of therapeutic agent (e.g., nucleic acid) to lipid, the particular therapeutic agent (e.g., nucleic acid) used, the disease or disorder being treated, the age, weight, and condition of the patient, and the judgment of the clinician, but will generally be between about 0.01 and about 50 mg per kilogram of body weight, preferably between about 0.1 and about 5 mg/kg of body weight, or about $10^8$-$10^{10}$ particles per administration (e.g., injection).

B. In Vitro Administration

For in vitro applications, the delivery of therapeutic agents such as nucleic acids (e.g., interfering RNA) can be to any cell grown in culture, whether of plant or animal origin, vertebrate or invertebrate, and of any tissue or type. In preferred embodiments, the cells are animal cells, more preferably mammalian cells, and most preferably human cells.

Contact between the cells and the lipid particles, when carried out in vitro, takes place in a biologically compatible medium. The concentration of particles varies widely depending on the particular application, but is generally between about 1 μmol and about 10 mmol. Treatment of the cells with the lipid particles is generally carried out at physiological temperatures (about 37° C.) for periods of time of from about 1 to 48 hours, preferably of from about 2 to 4 hours.

In one group of preferred embodiments, a lipid particle suspension is added to 60-80% confluent plated cells having a cell density of from about $10^3$ to about $10^5$ cells/ml, more preferably about $2 \times 10^4$ cells/ml. The concentration of the suspension added to the cells is preferably of from about 0.01 to 0.2 μg/ml, more preferably about 0.1 μg/ml.

Using an Endosomal Release Parameter (ERP) assay, the delivery efficiency of the SNALP or other lipid particle of the invention can be optimized. An ERP assay is described in detail in U.S. Patent Publication No. 20030077829, the disclosure of which is herein incorporated by reference in its entirety for all purposes. More particularly, the purpose of an ERP assay is to distinguish the effect of various cationic lipids and helper lipid components of SNALP based on their relative effect on binding/uptake or fusion with/destabilization of the endosomal membrane. This assay allows one to determine quantitatively how each component of the SNALP or other lipid particle affects delivery efficiency, thereby optimizing the SNALP or other lipid particle. Usually, an ERP assay measures expression of a reporter protein (e.g., luciferase, β-galactosidase, green fluorescent protein (GFP), etc.), and in some instances, a SNALP formulation optimized for an expression plasmid will also be appropriate for encapsulating an interfering RNA. In other instances, an ERP assay can be adapted to measure downregulation of transcription or translation of a target sequence in the presence or absence of an interfering RNA (e.g., siRNA). By comparing the ERPs for each of the various SNALP or other lipid particles, one can readily determine the optimized system, e.g., the SNALP or other lipid particle that has the greatest uptake in the cell.

C. Cells for Delivery of Lipid Particles

The compositions and methods of the present invention are used to treat a wide variety of cell types, in vivo and in vitro. Suitable cells include, e.g., hematopoietic precursor (stem) cells, fibroblasts, keratinocytes, hepatocytes, endothelial cells, skeletal and smooth muscle cells, osteoblasts, neurons, quiescent lymphocytes, terminally differentiated cells, slow or noncycling primary cells, parenchymal cells, lymphoid cells, epithelial cells, bone cells, and the like. In preferred embodiments, an active agent or therapeutic agent such as an interfering RNA (e.g., siRNA) is delivered to cancer cells such as, e.g., lung cancer cells, colon cancer cells, rectal cancer cells, anal cancer cells, bile duct cancer cells, small intestine cancer cells, stomach (gastric) cancer cells, esophageal cancer cells, gallbladder cancer cells, liver cancer cells, pancreatic cancer cells, appendix cancer cells, breast cancer cells, ovarian cancer cells, cervical cancer cells, prostate cancer cells, renal cancer cells, cancer cells of the central nervous system, glioblastoma tumor cells, skin cancer cells, lymphoma cells, choriocarcinoma tumor cells, head and neck cancer cells, osteogenic sarcoma tumor cells, and blood cancer cells.

In vivo delivery of lipid particles such as SNALP encapsulating an interfering RNA (e.g., siRNA) is suited for targeting cells of any cell type. The methods and compositions can be employed with cells of a wide variety of vertebrates, including mammals, such as, e.g, canines, felines, equines, bovines, ovines, caprines, rodents (e.g., mice, rats, and guinea pigs), lagomorphs, swine, and primates (e.g. monkeys, chimpanzees, and humans).

To the extent that tissue culture of cells may be required, it is well-known in the art. For example, Freshney, Culture of Animal Cells, a Manual of Basic Technique, 3rd Ed., Wiley-Liss, New York (1994), Kuchler et al., Biochemical Methods in Cell Culture and Virology, Dowden, Hutchinson and Ross, Inc. (1977), and the references cited therein provide a general guide to the culture of cells. Cultured cell systems often will be in the form of monolayers of cells, although cell suspensions are also used.

D. Detection of Lipid Particles

In some embodiments, the lipid particles of the present invention (e.g., SNALP) are detectable in the subject at about 1, 2, 3, 4, 5, 6, 7, 8 or more hours. In other embodiments, the lipid particles of the present invention (e.g., SNALP) are detectable in the subject at about 8, 12, 24, 48, 60, 72, or 96 hours, or about 6, 8, 10, 12, 14, 16, 18, 19, 22, 24, 25, or 28 days after administration of the particles. The presence of the particles can be detected in the cells, tissues, or other biological samples from the subject. The particles may be detected, e.g., by direct detection of the particles, detection of a therapeutic nucleic acid such as an interfering RNA (e.g., siRNA) sequence, detection of the target sequence of interest (i.e., by detecting expression or reduced expression of the sequence of interest), or a combination thereof.

1. Detection of Particles

Lipid particles of the invention such as SNALP can be detected using any method known in the art. For example, a label can be coupled directly or indirectly to a component of the lipid particle using methods well-known in the art. A wide variety of labels can be used, with the choice of label depending on sensitivity required, ease of conjugation with the lipid particle component, stability requirements, and available instrumentation and disposal provisions. Suitable labels include, but are not limited to, spectral labels such as fluorescent dyes (e.g., fluorescein and derivatives, such as fluorescein isothiocyanate (FITC) and Oregon Green™; rhodamine and derivatives such Texas red, tetrarhodimine isothiocynate (TRITC), etc., digoxigenin, biotin, phycoerythrin, AMCA, CyDyes™, and the like; radiolabels such as $^3$H, $^{125}$I, $^{35}$S, $^{14}$C, $^{32}$P, $^{33}$P, etc.; enzymes such as horse radish peroxidase, alkaline phosphatase, etc.; spectral colorimetric labels such as colloidal gold or colored glass or plastic beads such as polystyrene, polypropylene, latex, etc. The label can be detected using any means known in the art.

2. Detection of Nucleic Acids

Nucleic acids (e.g., interfering RNA) are detected and quantified herein by any of a number of means well-known to those of skill in the art. The detection of nucleic acids may proceed by well-known methods such as Southern analysis, Northern analysis, gel electrophoresis, PCR, radiolabeling, scintillation counting, and affinity chromatography. Additional analytic biochemical methods such as spectrophotometry, radiography, electrophoresis, capillary electrophoresis, high performance liquid chromatography (HPLC), thin layer chromatography (TLC), and hyperdiffusion chromatography may also be employed.

The selection of a nucleic acid hybridization format is not critical. A variety of nucleic acid hybridization formats are known to those skilled in the art. For example, common formats include sandwich assays and competition or displacement assays. Hybridization techniques are generally described in, e.g., "Nucleic Acid Hybridization, A Practical Approach," Eds. Hames and Higgins, IRL Press (1985).

The sensitivity of the hybridization assays may be enhanced through use of a nucleic acid amplification system which multiplies the target nucleic acid being detected. In vitro amplification techniques suitable for amplifying sequences for use as molecular probes or for generating nucleic acid fragments for subsequent subcloning are known. Examples of techniques sufficient to direct persons of skill through such in vitro amplification methods, including the polymerase chain reaction (PCR) the ligase chain reaction (LCR), Qβ-replicase amplification and other RNA polymerase mediated techniques (e.g., NASBA™) are found in Sambrook et al., In *Molecular Cloning: A Laboratory Manual*, Cold Spring Harbor Laboratory Press (2000); and Ausubel et al., SHORT PROTOCOLS IN MOLECULAR BIOLOGY, eds., Current Protocols, Greene Publishing Associates, Inc. and John Wiley & Sons, Inc. (2002); as well as U.S. Pat. No. 4,683,202; PCR Protocols, A Guide to Methods and Applications (Innis et al. eds.) Academic Press Inc. San Diego, Calif. (1990); Arnheim & Levinson (Oct. 1, 1990), C&EN 36; The Journal Of NIH Research, 3:81 (1991); Kwoh et al., *Proc. Natl. Acad. Sci. USA*, 86:1173 (1989); Guatelli et al., *Proc. Natl. Acad. Sci. USA*, 87:1874 (1990); Lomell et al., *J. Clin. Chem.*, 35:1826 (1989); Landegren et al., *Science*, 241:1077 (1988); Van Brunt, Biotechnology, 8:291 (1990); Wu and Wallace, Gene, 4:560 (1989); Barringer et al., *Gene*, 89:117 (1990); and Sooknanan and Malek, *Biotechnology*, 13:563 (1995). Improved methods of cloning in vitro amplified nucleic acids are described in U.S. Pat. No. 5,426,039. Other methods described in the art are the nucleic acid sequence based amplification (NASBA™, Cangene, Mississauga, Ontario) and Qβ-replicase systems. These systems can be used to directly identify mutants where the PCR or LCR primers are designed to be extended or ligated only when a select sequence is present. Alternatively, the select sequences can be generally amplified using, for example, nonspecific PCR primers and the amplified target region later probed for a specific sequence indicative of a mutation. The disclosures of the above-described references are herein incorporated by reference in their entirety for all purposes.

Nucleic acids for use as probes, e.g., in in vitro amplification methods, for use as gene probes, or as inhibitor components are typically synthesized chemically according to the solid phase phosphoramidite triester method described by Beaucage et al., *Tetrahedron Letts.*, 22:1859 1862 (1981), e.g., using an automated synthesizer, as described in Needham VanDevanter et al., *Nucleic Acids Res.*, 12:6159 (1984). Purification of polynucleotides, where necessary, is typically performed by either native acrylamide gel electrophoresis or by anion exchange HPLC as described in Pearson et al., *J. Chrom.*, 255:137 149 (1983). The sequence of the synthetic polynucleotides can be verified using the chemical degradation method of Maxam and Gilbert (1980) in Grossman and Moldave (eds.) Academic Press, New York, *Methods in Enzymology*, 65:499.

An alternative means for determining the level of transcription is in situ hybridization. In situ hybridization assays are well-known and are generally described in Angerer et al., *Methods Enzymol.*, 152:649 (1987). In an in situ hybridization assay, cells are fixed to a solid support, typically a glass slide. If DNA is to be probed, the cells are denatured with heat or alkali. The cells are then contacted with a hybridization solution at a moderate temperature to permit annealing of specific probes that are labeled. The probes are preferably labeled with radioisotopes or fluorescent reporters.

VIII. Examples

The present invention will be described in greater detail by way of specific examples. The following examples are offered for illustrative purposes, and are not intended to limit the invention in any manner. Those of skill in the art will readily recognize a variety of noncritical parameters which can be changed or modified to yield essentially the same results.

Example 1

Materials and Methods siRNA:

All siRNA molecules used in these studies were chemically synthesized by the University of Calgary (Calgary, AB) or Dharmacon Inc. (Lafayette, Colo.). The siRNAs were desalted and annealed using standard procedures.

Lipid Encapsulation of siRNA:

In some embodiments, siRNA molecules were encapsulated into nucleic acid-lipid particles composed of the following lipids: the lipid conjugate PEG-cDMA (3-N-[(-Methoxy-poly(ethylene glycol)2000)carbamoyl]-1,2-dimyristyloxypropylamine); the cationic lipid DLinDMA (1,2-Dilinoleyloxy-3-(N,N-dimethyl)aminopropane); the phospholipid DPPC (1,2-Dipalmitoyl-sn-glycero-3-phosphocholine; Avanti Polar Lipids; Alabaster, Ala.); and synthetic cholesterol (Sigma-Aldrich Corp.; St. Louis, Mo.) in the molar ratio 1.4:57.1:7.1:34.3, respectively. In other words, siRNAs were encapsulated into SNALP of the following "1:57" formulation: 1.4% PEG-cDMA; 57.1% DLinDMA; 7.1% DPPC; and 34.3% cholesterol. In other embodiments, siRNA molecules were encapsulated into phospholipid-free SNALP composed of the following lipids: the lipid conjugate PEG-cDMA; the cationic lipid DLinDMA; and synthetic cholesterol in the molar ratio 1.5:61.5:36.9, respectively. In other words, siRNAs were encapsulated into phospholipid-free SNALP of the following "1:62" formulation: 1.5% PEG-cDMA; 61.5% DLinDMA; and 36.9% cholesterol. For vehicle controls, empty particles with identical lipid composition were formed in the absence of siRNA. It should be understood that the 1:57 formulation and 1:62 formulation are target formulations, and that the amount of lipid (both cationic and non-cationic) present and the amount of lipid conjugate present in the formulation may vary. Typically, in the 1:57 formulation, the amount of cationic lipid will be 57 mol %±5 mol %, and the amount of lipid conjugate will be 1.5 mol %±0.5 mol %, with the balance of the 1:57 formulation being made up of non-cationic lipid (e.g., phospholipid, cholesterol, or a mixture of the two). Similarly, in the 1:62 formulation, the amount of cationic lipid will be 62 mol % t 5 mol %, and the amount of lipid conjugate will be 1.5 mol % f 0.5 mol %, with the balance of the 1:62 formulation being made up of the non-cationic lipid (e.g., cholesterol).

Example 2

Eg5 siRNA Formulated as 1:57 SNALP are Potent Inhibitors of Cell Growth In Vitro SNALP formulations were prepared with an siRNA targeting Eg5 as the nucleic acid component. Eg5 is a member of kinesin-related proteins that are involved in functions related to movements of organelles, microtubules, or chromosomes along microtubules. These functions include axonal transport, microtubule sliding during nuclear fusion or division, and chromosome disjunction during meiosis and early mitosis. Eg5 plays a critical role in mitosis of mammalian cells. The Eg5 siRNA used in this study is provided in Table 1. The modifications involved introducing 2'OMe-uridine at selected positions in the sense and antisense strands of the Eg5 2263 siRNA sequence, in which the siRNA duplex contained less than about 20% 2'OMe-modified nucleotides.

TABLE 1 siRNA duplex comprising sense and antisense Eg5 RNA polynucleotides.

| Modification | Eg5 2263 siRNA sequence | SEQ ID NO: | % 2'OMe-Modified | % Modified in DS Region |
|---|---|---|---|---|
| U/U | 5'-CUGAAGACCUGAAGACAAUdTdT-3' | 1 | 6/42 = 14.3% | 6/38 = 15.8% |
|  | 3'-dTdTGACUUCUGGACUUCUGUUA-5' | 2 |  |  |

Column 1: "U/U" = 2'OMe-uridine modified siRNA duplex;
Column 2: 2'OMe-modified nucleotides are indicated in bold and underlined. The siRNA duplex can alternatively or additionally comprise 2'-deoxy-2'-fluoro (2'F) nucleotides, 2'-deoxy nucleotides, 2'-O-(2-methoxyethyl) (MOE) nucleotides, and/or locked nucleic acid (LNA) nucleotides. "dT" = deoxythymidine.
Column 3: The number and percentage of 2'OMe-modified nucleotides in the siRNA duplex are provided.
Column 4: The number and percentage of modified nucleotides in the double-stranded (DS) region of the siRNA duplex are provided.

The lipid components and physical characteristics of the SNALP formulations are summarized in Table 2. The lipid:drug ratio is described in units of mg total lipid per mg nucleic acid. Mean particle size and polydispersity were measured on a Malvern Instruments Zetasizer. Encapsulation of nucleic acid was measured using a Ribogreen assay essentially as described in Heyes et al., *Journal of Controlled Release*, 107:276-287 (2005).

Silencing of Eg5 by siRNA transfection causes mitotic arrest and apoptosis in mammalian cells. Cell viability following transfection with SNALP containing an siRNA targeting Eg5 therefore provides a simple biological readout of in vitro transfection efficiency. Cell viability of in vitro cell cultures was assessed using the commercial reagent CellTiter-Blue® (Promega Corp.; Madison, Wis.), a resazurin dye that is reduced by metabolically active cells to the fluorogenic product resorufin. The human colon cancer cell line HT29 was cultured using standard tissue culture techniques. 72 hours after SNALP application, CellTiter-Blue® reagent was added to the culture to quantify the metabolic activity of the cells, which is a measure of cell viability. Data are presented as a percent of cell viability relative to ("untreated") control cells that received phosphate buffered saline (PBS) vehicle only.

Figure 1B:
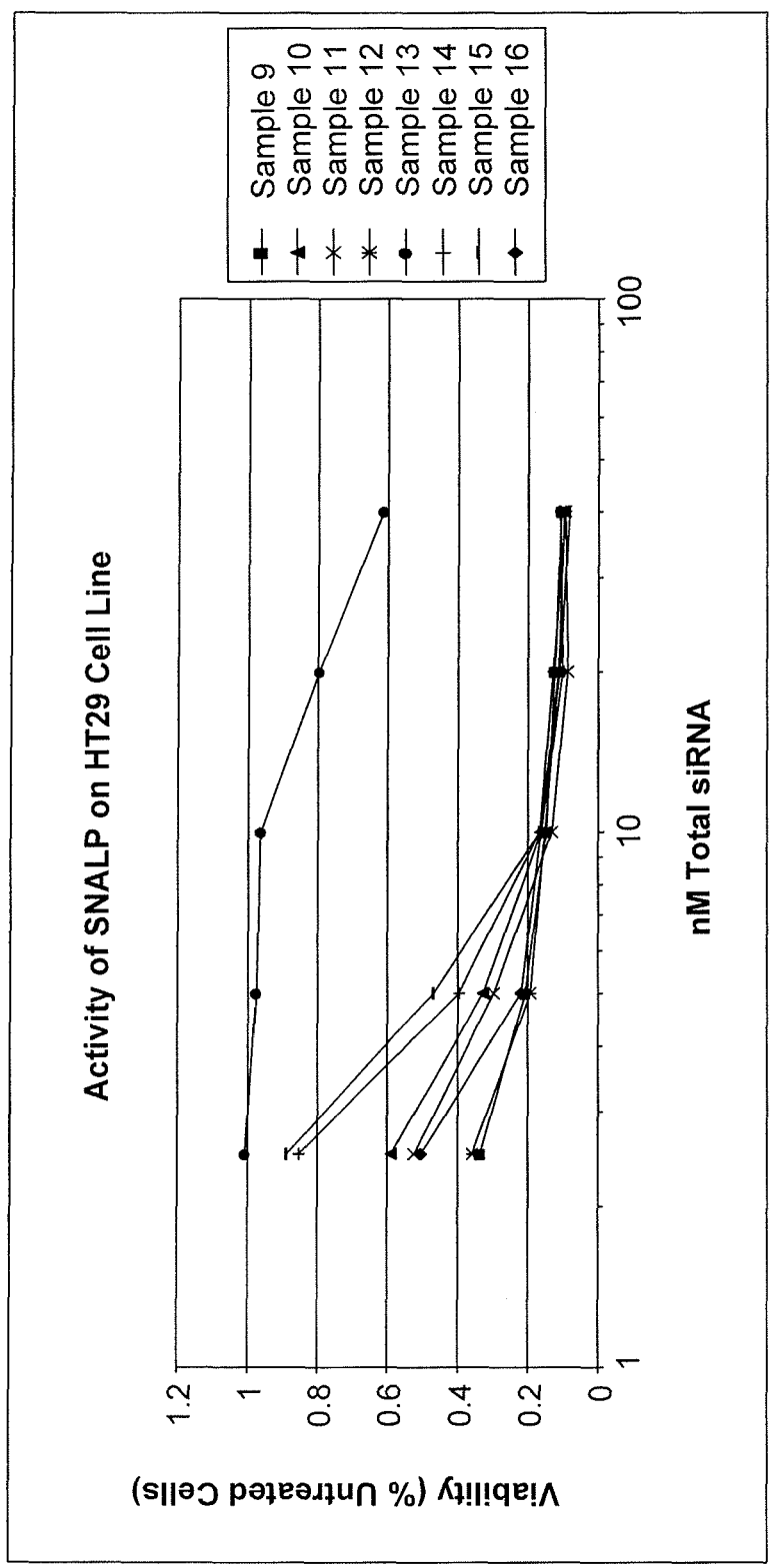

FIG. 1 shows that the 1:57 SNALP formulation containing Eg5 2263 U/U siRNA was among the most potent inhibitors of tumor cell growth at all siRNA concentrations tested (see, FIG. 1B, Sample 9).

Example 3

ApoB siRNA Formulated as 1:57 SNALP have Potent Silencing Activity In Vivo

SNALP formulations were prepared with an siRNA targeting apolipoprotein B (ApoB) as the nucleic acid component. ApoB is the main apolipoprotein of chylomicrons and low density lipoproteins (LDL). Mutations in ApoB are associated with hypercholesterolemia. ApoB occurs in the plasma in 2 main forms, ApoB48 and ApoB 100, which are synthe-

TABLE 2

Characteristics of the SNALP formulations used in this study.

| | Formulation Composition, Mole % | | Finished Product Characterization | |
|---|---|---|---|---|
| Sample No. | PEG(2000)-C-DMA\|DLinDMA\|DPPC\|Cholesterol | Lipid/Drug Ratio | Size (nm) | Polydispersity | % Encapsulation |
| 1 | 2\|40\|10\|48 | 12.4 | 57 | 0.07 | 90 |
| 2 | 1.8\|36.4\|18.2\|43.6 | 14.0 | 72 | 0.12 | 89 |
| 3 | 1.4\|27.0\|6.8\|64.9 | 16.5 | 70 | 0.12 | 92 |
| 4 | 1.3\|25.3\|12.7\|60.8 | 18.1 | 76 | 0.07 | 93 |
| 5 | 3.9\|39.2\|9.8\|47.1 | 13.5 | 53 | 0.27 | 86 |
| 6 | 3.6\|35.7\|17.9\|42.9 | 15.1 | 58 | 0.18 | 87 |
| 7 | 2.7\|26.7\|6.7\|64.0 | 17.6 | 56 | 0.17 | 92 |
| 8 | 2.5\|25.0\|12.5\|60.0 | 19.2 | 61 | 0.13 | 92 |
| 9 | 1.4\|57.1\|7.1\|34.3 | 17.8 | 84 | 0.10 | 88 |
| 10 | 1.3\|53.3\|13.3\|32.0 | 19.5 | 83 | 0.10 | 89 |
| 11 | 1.1\|42.6\|5.3\|51.1 | 22.0 | 80 | 0.10 | 93 |
| 12 | 1.0\|40.4\|10.1\|48.5 | 23.6 | 78 | 0.11 | 88 |
| 13 | 2.8\|56.3\|7.0\|33.8 | 19.0 | 62 | 0.14 | 80 |
| 14 | 2.6\|52.6\|13.2\|31.6 | 20.6 | 66 | 0.14 | 82 |
| 15 | 2.1\|42.1\|5.3\|50.5 | 23.1 | 71 | 0.16 | 91 |
| 16 | 2\|40\|10\|48 | 24.7 | 67 | 0.14 | 92 | sized in the intestine and liver, respectively, due to an organ-specific stop codon. The ApoB siRNA used in this study is provided in Table 3. The modifications involved introducing 2'OMe-uridine or 2'OMe-guanosine at selected positions in the sense and antisense strands of the ApoB siRNA sequence, in which the siRNA duplex contained less than about 20% 2'OMe-modified nucleotides.

BALB/c mice (female, at least 4 weeks old) were obtained from Harlan Labs. After an acclimation period (of at least 7 days), animals were administered SNALP by intravenous (IV) injection in the lateral tail vein once daily on Study Day 0 (1 dose total per animal). Dosage was 1 mg encapsulated siRNA per kg body weight, corresponding to 10 ml/kg (rounded to the nearest 10 µl). As a negative control, one

TABLE 3 siRNA duplex comprising sense and antisense ApoB RNA polynucleotides.

| Position | Modification | ApoB siRNA sequence | SEQ ID NO: | % 2'OMe-Modified | % Modified in DS Region |
|---|---|---|---|---|---|
| 10048 | U2/2 G1/2 | 5'-AGUGUCAUCACACUGAAUACC-3' | 3 | 7/42 = 16.7% | 7/38 = 18.4% |
| | | 3'-GUUCACAGUAGUGUGACUUAU-5' | 4 | | |

Column 1: The number refers to the nucleotide position of the 5' base of the sense strand relative to the mouse ApoB mRNA sequence XM_137955.
Column 2: The numbers refer to the distribution of 2'OMe chemical modifications in each strand.
Column 3: 2'OMe-modified nucleotides are indicated in bold and underlined. The siRNA duplex can alternatively or additionally comprise 2'-deoxy-2'-fluoro (2'F) nucleotides, 2'-deoxy nucleotides, 2'-O-(2-methoxyethyl) (MOE) nucleotides, and/or locked nucleic acid (LNA) nucleotides.
Column 4: The number and percentage of 2'OMe-modified nucleotides in the siRNA duplex are provided.
Column 5: The number and percentage of modified nucleotides in the double-stranded (DS) region of the siRNA duplex are provided.

The lipid components and physical characteristics of the formulations are summarized in Table 4. The lipid:drug ratio is described in units of mg total lipid per mg nucleic acid. Mean particle size and polydispersity were measured on a Malvern Instruments Zetasizer. Encapsulation of nucleic acid was measured using a Ribogreen assay essentially as described in Heyes et al., *Journal of Controlled Release*, 107:276-287 (2005).

group of animals was given an IV injection of phosphate buffered saline (PBS) vehicle. On Study Day 2, animals were euthanized and liver tissue was collected in RNAlater.

Liver tissues were analyzed for ApoB mRNA levels normalized against glyceraldehyde-3-phosphate dehydrogenase (GAPDH) mRNA levels using the QuantiGene assay (Pa-

TABLE 4

Characteristics of the SNALP formulations used in this study.

| | Formulation Composition | Lipid/Drug | Finished Product Characterization | | |
|---|---|---|---|---|---|
| Group | Lipid Name & Mole % | Ratio | Size (nm) | Polydispersity | % Encapsulation |
| 2 | PEG(2000)-C-DMA\|DLinDMA\|DPPC\|Cholesterol 2\|40\|10\|48 | 12.4 | 59 | 0.15 | 93 |
| 3 | PEG(2000)-C-DMA\|DLinDMA\|Cholesterol 2.2\|44.4\|53.3 | 10.7 | 55 | 0.17 | 91 |
| 4 | PEG(2000)-C-DMA\|DLinDMA\|DOPC\|Cholesterol 2\|40\|10\|48 | 12.5 | 59 | 0.16 | 92 |
| 5 | PEG(2000)-C-DMA\|DLinDMA\|DMPC\|Cholesterol 2\|40\|10\|48 | 12.2 | 56 | 0.11 | 92 |
| 6 | PEG(2000)-C-DMA\|DLinDMA\|DPPE\|Cholesterol 1.8\|36.4\|18.2\|43.6 | 13.8 | 66 | 0.16 | 93 |
| 7 | PEG(2000)-C-DMA\|DLinDMA\|DPPC\|Cholestanol 2\|40\|10\|48 | 12.4 | 56 | 0.12 | 92 |
| 8 | PEG(2000)-C-DMA\|DLinDMA\|DPPC\|Cholesterol 1.4\|27.0\|6.8\|64.9 | 16.5 | 60 | 0.10 | 93 |
| 9 | PEG(2000)-C-DMA\|DLinDMA\|DPPC\|Cholesterol 1.3\|25.3\|12.7\|60.8 | 18.1 | 74 | 0.13 | 92 |
| 10 | PEG(2000)-C-DMA\|DLinDMA\|DPPC\|Cholesterol 2.5\|25.0\|12.5\|60.0 | 19.2 | 60 | 0.13 | 93 |
| 11 | PEG(2000)-C-DMA\|DLinDMA\|DPPC\|Cholesterol 1.4\|57.1\|7.4\|34.3 | 17.8 | 79 | 0.09 | 94 |
| 12 | PEG(2000)-C-DMA\|DLinDMA\|DPPC\|Cholesterol 1.0\|40.4\|10.1\|48.5 | 23.6 | 72 | 0.11 | 93 |
| 13 | PEG(2000)-C-DMA\|DLinDMA\|DPPC 2\|70\|28 | 8.7 | 73 | 0.09 | 87 |
| 14 | PEG(2000)-C-DMA\|DLinDMA\|DPPC 1.6\|54.7\|43.8 | 11.3 | 65 | 0.11 | 87 | nomics; Fremont, Calif.) essentially as described in Judge et al., *Molecular Therapy*, 13:494 (2006).

Figure 2:
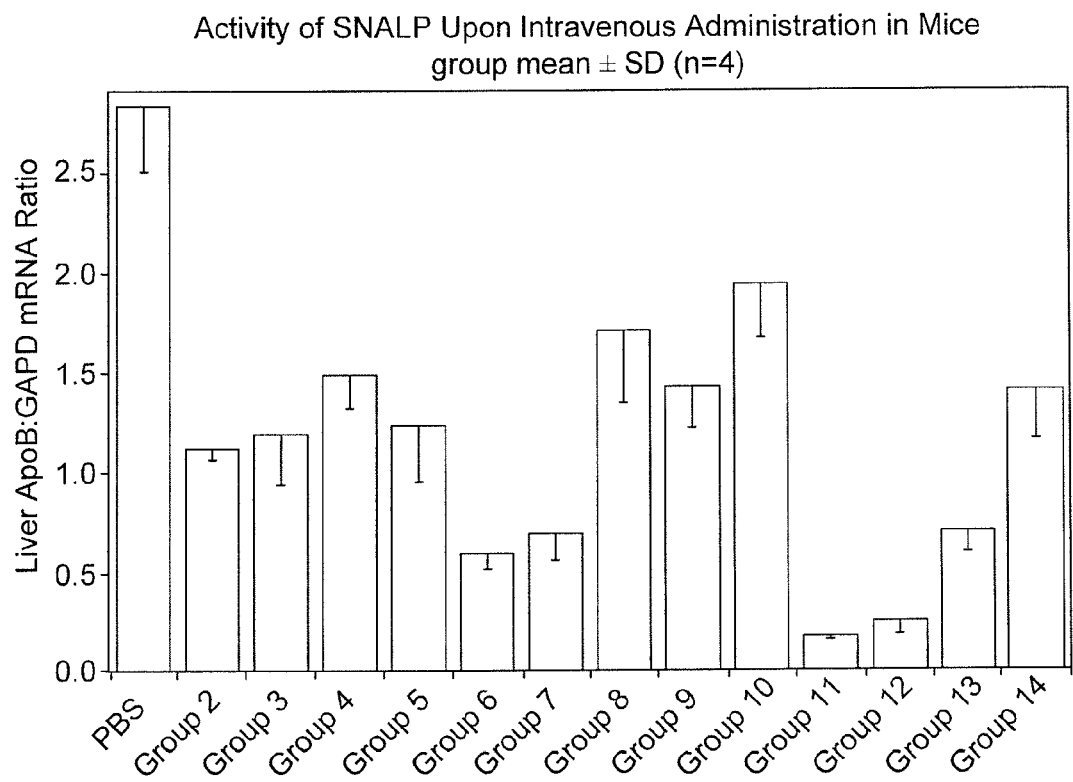
FIG. 2 illustrates data demonstrating the activity of 1:57 SNALP containing ApoB siRNA following intravenous administration in mice.

FIG. 2 shows that the 1:57 SNALP formulation containing ApoB 10048 U2/2 G1/2 siRNA was the most potent at reducing ApoB expression in vivo (see, Group 11).

Example 4

ApoB siRNA Formulated as 1:57 SNALP have Potent Silencing Activity In Vivo

SNALP formulations were prepared with the ApoB siRNA set forth in Table 3. The lipid components and physical characteristics of the formulations are summarized in Table 5. The lipid:drug ratio is described in units of mg total lipid per mg nucleic acid. Mean particle size and polydispersity were measured on a Malvern Instruments Zetasizer. Encapsulation of nucleic acid was measured using a Ribogreen assay essentially as described in Heyes et al., *Journal of Controlled Release*, 107:276-287 (2005).

TABLE 5

Characteristics of the SNALP formulations used in this study.

| SNALP (L:D ratio) | siRNA Payload | Particle Size (Polydispersity) | % Encapsulation |
|---|---|---|---|
| 2:30 (13) | ApoB-10048 U2/2 G1/2 | 65 nm (0.16) | 88 |
| 1:57 (9) | ApoB-10048 U2/2 G1/2 | 74 nm (0.10) | 89 |

The 2:30 SNALP formulation used in this study is lipid composition 2:30:20:48 as described in molar percentages of PEG-C-DMA, DLinDMA, DSPC, and cholesterol (in that order). This formulation was prepared by syringe press at an input lipid to drug (L:D) ratio (mg:mg) of 13:1.

The 1:57 SNALP formulation used in this study is lipid composition 1.5:57.1:7:34.3 as described in molar percentages of PEG-C-DMA, DLinDMA, DPPC, and cholesterol (in that order). This formulation was prepared by syringe press at an input lipid to drug (L:D) ratio (mg:mg) of 9:1.

BALB/c mice (female, 4 weeks old) were obtained from Harlan Labs. After an acclimation period (of at least 7 days), animals were administered SNALP by intravenous (IV) injection in the lateral tail vein once daily on Study Days 0, 1, 2, 3 & 4 for a total of 5 doses per animal. Daily dosage was either 1.0 (for 2:30 SNALP) or 0.1 (for 1:57 SNALP) mg encapsulated siRNA per kg body weight, corresponding to 10 ml/kg (rounded to the nearest 10 µl). As a negative control, one group of animals was given IV injections of phosphate buffered saline (PBS) vehicle. On Study Day 7, 72 h after the last treatment, animals were euthanized and liver tissue was collected in RNAlater.

Liver tissues were analyzed for ApoB mRNA levels normalized against glyceraldehyde-3-phosphate dehydrogenase (GAPDH) mRNA levels using the QuantiGene assay (Panomics; Fremont, Calif.) essentially as described in Judge et al., *Molecular Therapy*, 13:494 (2006).

Figure 3:
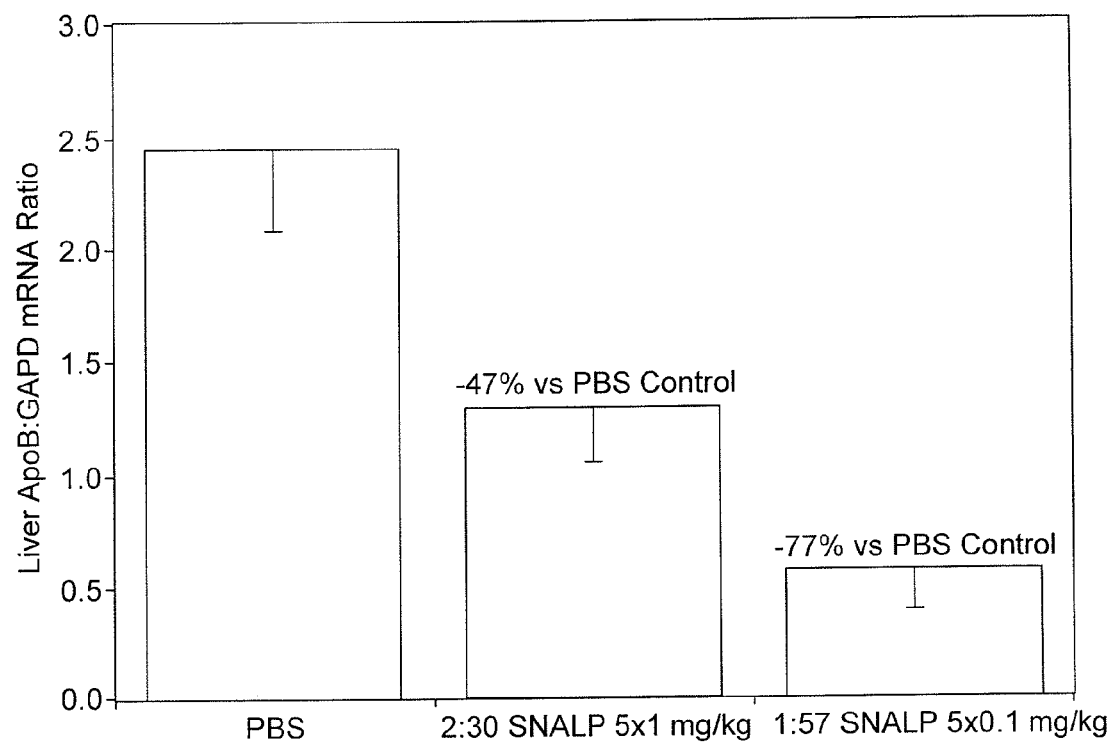
FIG. 3 illustrates additional data demonstrating the activity of 1:57 SNALP containing ApoB siRNA following intravenous administration in mice. Each bar represents the group mean of five animals. Error bars indicate the standard deviation.

FIG. 3 shows that the 1:57 SNALP containing ApoB 10048 U2/2 G1/2 siRNA was more than 10 times as efficacious as the 2:30 SNALP in mediating ApoB gene silencing in mouse liver at a 10-fold lower dose.

Example 5

ApoB siRNA Formulated as 1:57 or 1:62 SNALP have Potent Silencing Activity In Vivo SNALP formulations were prepared with the ApoB siRNA set forth in Table 3. The lipid components and physical characteristics of the formulations are summarized in Table 6. The lipid:drug ratio is described in units of mg total lipid per mg nucleic acid. Mean particle size and polydispersity were measured on a Malvern Instruments Zetasizer. Encapsulation of nucleic acid was measured using a Ribogreen assay essentially as described in Heyes et al., *Journal of Controlled Release*, 107:276-287 (2005).

TABLE 6

Characteristics of the SNALP formulations used in this study.

| Group | Formulation Composition Lipid Name & Mole % | Lipid/Drug Ratio | Finished Product Characterization | | |
|---|---|---|---|---|---|
| | | | Size (nm) | Polydispersity | % Encapsulation |
| 2 | PEG(2000)-C-DMA\|DLinDMA\|DPPC\|Cholesterol 1.4\|57.1\|7.1\|34.3 | 8.9 | 76 | 0.06 | 89 |
| 3 | PEG(2000)-C-DMA\|DLinDMA\|Cholesterol 1.5\|61.5\|36.9 | 8.1 | 76 | 0.04 | 86 |
| 4 | PEG(2000)-C-DMA\|DODMA\|DPPC\|Cholesterol 1.4\|57.1\|7.1\|34.3 | 9.0 | 72 | 0.05 | 95 |
| 5 | PEG(5000)-C-DMA\|DLinDMA\|DPPC\|Cholesterol 1.4\|57.1\|7.1\|34.3 | 9.6 | 52 | 0.16 | 89 |
| 6 | PEG(2000)-C-DMA\|DLinDMA\|DPPC\|Cholestanol 1.4\|57.1\|7.1\|34.3 | 8.9 | 68 | 0.10 | 94 |
| 7 | PEG(2000)-C-DMA\|DLinDMA\|DPPE\|Cholesterol 1.4\|57.1\|7.1\|34.3 | 8.9 | 72 | 0.07 | 95 |
| 8 | PEG(2000)-C-DMA\|DLinDMA\|DPPC 1.8\|70.2\|28.1 | 8.6 | 74 | 0.13 | 86 |

BALB/c mice (female, at least 4 weeks old) were obtained from Harlan Labs. After an acclimation period (of at least 7 days), animals were administered SNALP by intravenous (IV) injection in the lateral tail vein once daily on Study Day 0 (1 dose total per animal). Dosage was 0.75 mg encapsulated siRNA per kg body weight, corresponding to 10 ml/kg (rounded to the nearest 10 µl). As a negative control, one group of animals was given an IV injection of phosphate buffered saline (PBS) vehicle. On Study Day 2, animals were euthanized and liver tissue was collected in RNAlater.

Liver tissues were analyzed for ApoB mRNA levels normalized against glyceraldehyde-3-phosphate dehydrogenase (GAPDH) mRNA levels using the QuantiGene assay (Panomics; Fremont, Calif.) essentially as described in Judge et al., *Molecular Therapy*, 13:494 (2006).

Figure 4:
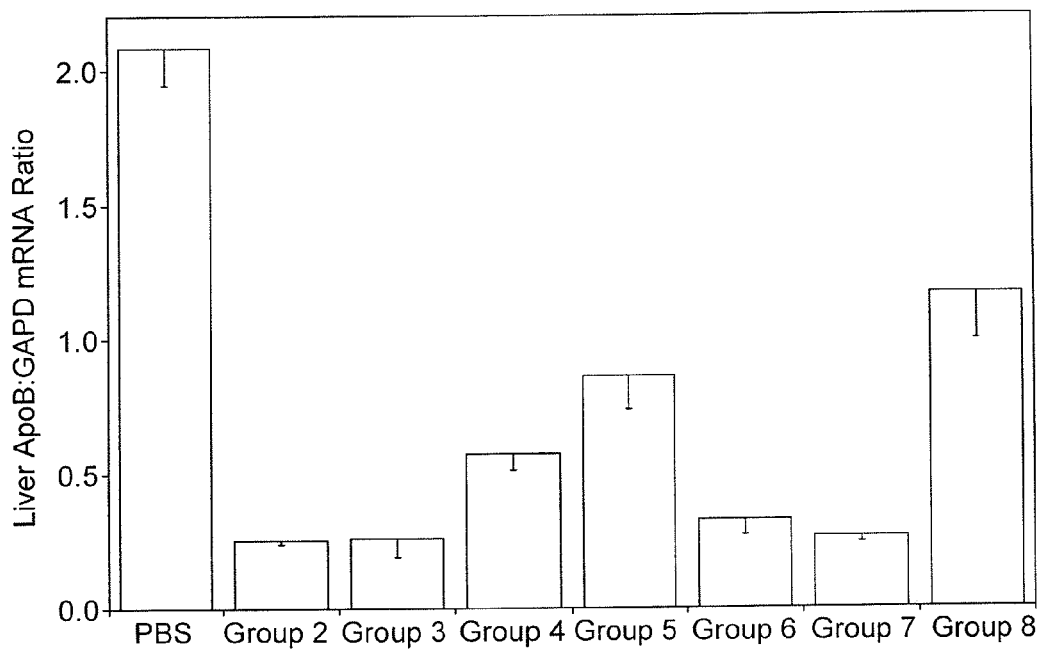
FIG. 4 illustrates data demonstrating the activity of 1:57 and 1:62 SNALP containing ApoB siRNA following intravenous administration in mice.

FIG. 4 shows that the 1:57 and 1:62 SNALP formulations had comparable ApoB silencing activity in vivo (see, e.g., Groups 2 & 3).

Example 6

ApoB siRNA Formulated as 1:62 SNALP have Potent Silencing Activity In Vivo

SNALP formulations were prepared with the ApoB siRNA set forth in Table 3. The lipid components and physical characteristics of the formulations are summarized in Table 7.

The lipid:drug ratio is described in units of mg total lipid per mg nucleic acid. Mean particle size and polydispersity were measured on a Malvern Instruments Zetasizer. Encapsulation of nucleic acid was measured using a Ribogreen assay essentially as described in Heyes et al., *Journal of Controlled Release*, 107:276-287 (2005).

TABLE 7

Characteristics of the SNALP formulations used in this study.

| | Formulation Composition, Mole % | Lipid/ | Finished Product Characterization | | |
|---|---|---|---|---|---|
| Group | PEG(2000)-C-DMA\|DLinDMA\|Cholesterol | Drug Ratio | Size (nm) | Poly-dispersity | % Encap-sulation |
| 2 | 1.5\|61.5\|36.9 | 6.1 | 80 | 0.07 | 92 |
| 3 | 1.4\|54.8\|43.8 | 6.6 | 74 | 0.05 | 89 |
| 4 | 2.0\|61.2\|36.7 | 6.2 | 71 | 0.11 | 91 |
| 5 | 1.8\|54.5\|43.6 | 6.7 | 67 | 0.09 | 91 |
| 6 | 1.3\|68.1\|30.6 | 7.4 | 91 | 0.06 | 89 |
| 7 | 1.2\|61.8\|37.1 | 8.0 | 87 | 0.10 | 90 |
| 8 | 1.7\|67.8\|30.5 | 7.6 | 81 | 0.07 | 91 |
| 9 | 1.4\|56.3\|42.3 | 8.6 | 75 | 0.11 | 92 |
| 10 | 1.9\|61.3\|36.8 | 8.2 | 72 | 0.10 | 91 |
| 11 | 1.8\|56.1\|42.1 | 8.8 | 70 | 0.10 | 90 |
| 12 | 1.3\|66.7\|32.0 | 9.5 | 89 | 0.09 | 89 |
| 13 | 1.2\|61.7\|37.0 | 10.0 | 87 | 0.10 | 91 |
| 14 | 1.7\|66.4\|31.9 | 9.6 | 82 | 0.11 | 90 |
| 15 | 1.5\|61.5\|36.9 | 10.1 | 79 | 0.10 | 91 |

BALB/c mice (female, at least 4 weeks old) were obtained from Harlan Labs. After an acclimation period (of at least 7 days), animals were administered SNALP by intravenous (IV) injection in the lateral tail vein once daily on Study Day 0 (1 dose total per animal). Dosage was 0.1 mg encapsulated siRNA per kg body weight, corresponding to 10 ml/kg (rounded to the nearest 10 μl). As a negative control, one group of animals was given an IV injection of phosphate buffered saline (PBS) vehicle. On Study Day 2, animals were euthanized and liver tissue was collected in RNAlater.

Liver tissues were analyzed for ApoB mRNA levels normalized against glyceraldehyde-3-phosphate dehydrogenase (GAPDH) mRNA levels using the QuantiGene assay (Panomics; Fremont, Calif.) essentially as described in Judge et al., *Molecular Therapy*, 13:494 (2006).

Figure 5:
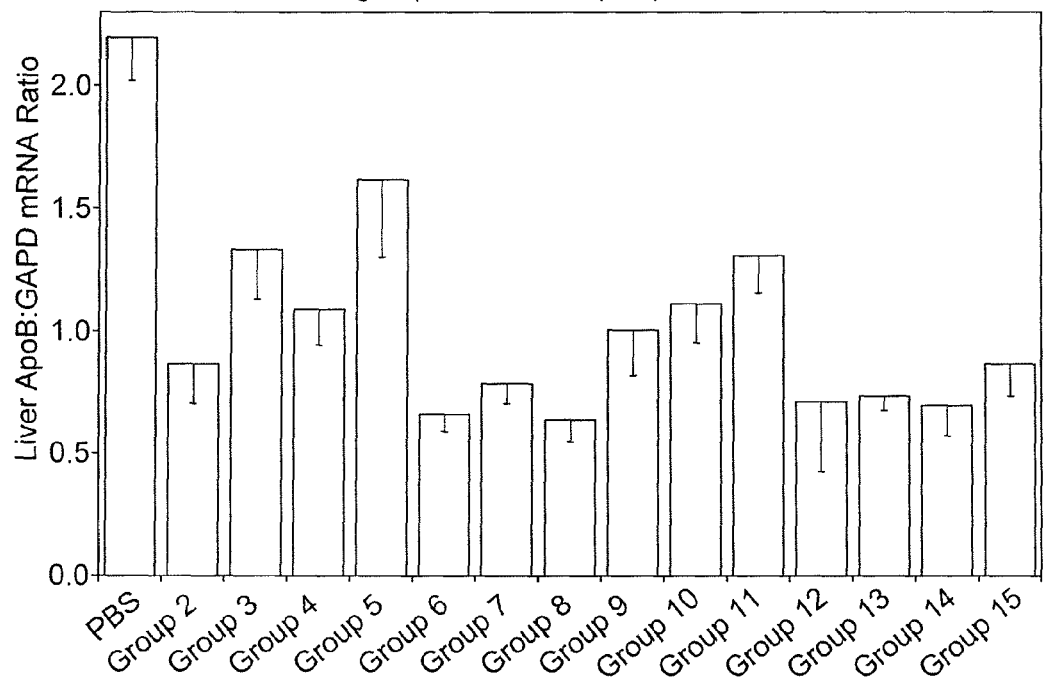
FIG. 5 illustrates data demonstrating the activity of 1:62 SNALP containing ApoB siRNA following intravenous administration in mice.

FIG. 5 shows that the 1:62 SNALP formulation was one of the most potent inhibitors of ApoB expression at two different lipid:drug ratios (i.e., 6.1 & 10.1) among the phospholipid-free SNALP formulations tested (see, Groups 2 & 15).

Example 7

In Vivo Silencing of ApoB Expression Using 1:57 SNALP Prepared Via a Syringe Press or Gear Pump Process This study illustrates a comparison of the tolerability and efficacy of the 1:57 SNALP formulation with ApoB-targeting siRNA as prepared by various manufacturing processes. In particular, 1:57 SNALP was prepared by a syringe press or gear pump process using either PBS or citrate buffer (post-blend dilution) and administered intravenously in mice.

Experimental Design

Animal Model: Female BALB/c mice, 5 wks old, n=4 per group/cage.

siRNA payload: ApoB10048 U2/2 G1/2 siRNA.

Tolerability:

| | | IV Injection | |
|---|---|---|---|
| Group | Formulation | siRNA mg/kg | Lipid mg/kg |
| 1 | PBS vehicle | Standard 10 mL/kg volume | |
| 2 | 1\|57 Citrate Direct Dil, Syringe Press | 7 | 77 |
| 3 | 1\|57 PBS Direct Dil, Syringe Press | 7 | 96 |
| 4 | 1\|57 PBS Direct Dil, Gear Pump | 7 | 79 |
| 5 | 1\|57 Citrate Direct Dil, Syringe Press | 9 | 99 |
| 6 | 1\|57 PBS Direct Dil, Syringe Press | 9 | 123 |
| 7 | 1\|57 PBS Direct Dil, Gear Pump | 9 | 102 |

Efficacy:

| | | IV Injection | |
|---|---|---|---|
| Group | Formulation | siRNA mg/kg | Lipid mg/kg |
| 8 | PBS vehicle | Standard 10 mL/kg volume | |
| 9 | 1\|57 PBS Direct Dil, Syringe Press | 0.05 | 0.68 |
| 10 | 1\|57 PBS Direct Dil, Gear Pump | 0.05 | 0.57 |
| 11 | 1\|57 PBS Direct Dil, Syringe Press | 0.1 | 1.36 |
| 12 | 1\|57 PBS Direct Dil, Gear Pump | 0.1 | 1.13 |

Formulation:

Formulations are provided at 0.005 to 0.9 mg siRNA/mL, 0.22 μm filter sterilized in crimp top vials.

Formulation Details:
1. Lipid composition "1|57 Citrate blend" used in this study is 1.4:57.1:7.1:34.3 as described in molar percentages of PEG-C-DMA, DLinDMA, DPPC, and cholesterol (in that order). This formulation has an input lipid to drug ratio of 8.9.
2. Gear pump set up included 0.8 mm T-connector and 400 mL/min speed.
3. siRNA used in this study is apoB-10048 U2/2 G1/2 siRNA.

Formulation Summary:

| | | Particle Size | | | |
|---|---|---|---|---|---|
| | 1:57 (9:1) + DOW siRNA | Zavg (nm) | Poly | % Encap | Final L:D (mg:mg) |
| 322-050807-1 | Syringe PBS Blend | 79 | 0.12 | 92 | 13.6 |
| 322-050807-2 | Syringe Citrate Blend | 86 | 0.11 | 91 | 11.0 |
| 322-050807-3 | Gear PBS Blend | 80 | 0.09 | 93 | 11.3 |

Procedures

Treatment: Just prior to the first treatment, animals are weighed and dose amounts are calculated based on the weight of individual animals (equivalent to 10 mL/kg, rounded to the nearest 10 μl). Test article is administered by IV injection through the tail vein once on Day 0 (1 dose total per animal). Body weight is measured daily (every 24 h) for the duration of the study. Cage-side observations are taken daily in concert with body weight measurements and additionally as warranted.

Group 1-7 Endpoint:

Animals are sacrificed on Day 1, 24 h after test article administration. Blood is collected by cardiac puncture upon sacrifice. Whole amount is collected into a SST microtainer for serum. Clot for 30 (to 60) min at room temp., centrifuge for 5 min at 16,000×g & 16° C., invert to confirm centrifugation is complete, and store at 4° C. Analyze complete small-animal clinical chemistry panel plus AST and SDH. Top priority list: ALT, AST, SDH, Bilirubin, Alkaline Phosphatase, GGT, BUN, CPK, Glucose. Secondary priority list: Creatinine, Albumin, Globulin, Total Protein.

Group 8-12 Endpoint:

Animals are sacrificed on Day 2, 48 h after test article administration. Blood is collected by cardiac puncture and processed for plasma. Immediately centrifuge for 5 min at 16,000×g (at 16° C.). Record any observations of unusual plasma appearance. Pipette off clear plasma supernatant into a clean microfuge tube and store at −80° C. The following tissues are removed and weighed separately: liver and spleen. The bottom (unattached) half of the left liver lobe is detached and submerged in >5 volumes of RNAlater (<0.3 g in 1.5 mL RNAlater in 2.0 mL tube), stored at least 16 hours at 4° C. prior to analysis and long term storage at −20° C. or −80° C. for archival purposes. Formulations are expected to be well tolerated. Mice which exhibit signs of distress associated with the treatment are terminated at the discretion of the vivarium staff.

Termination:

Mice are anaesthetized with a lethal dose of ketamine/xylazine; then cardiac puncture is performed followed by cervical dislocation.

Data Analysis:

Tolerability of treatment regime is monitored by animal appearance and behavior as well as body weight. Blood clinical chemistry is measured by automated analyzer. ApoB and GAPDH mRNA levels in liver are measured via QG assay. ApoB protein in plasma is measured via ELISA. Total cholesterol in plasma is measured via standard enzymatic/colorimetric assay.

Results

Figure 6A:
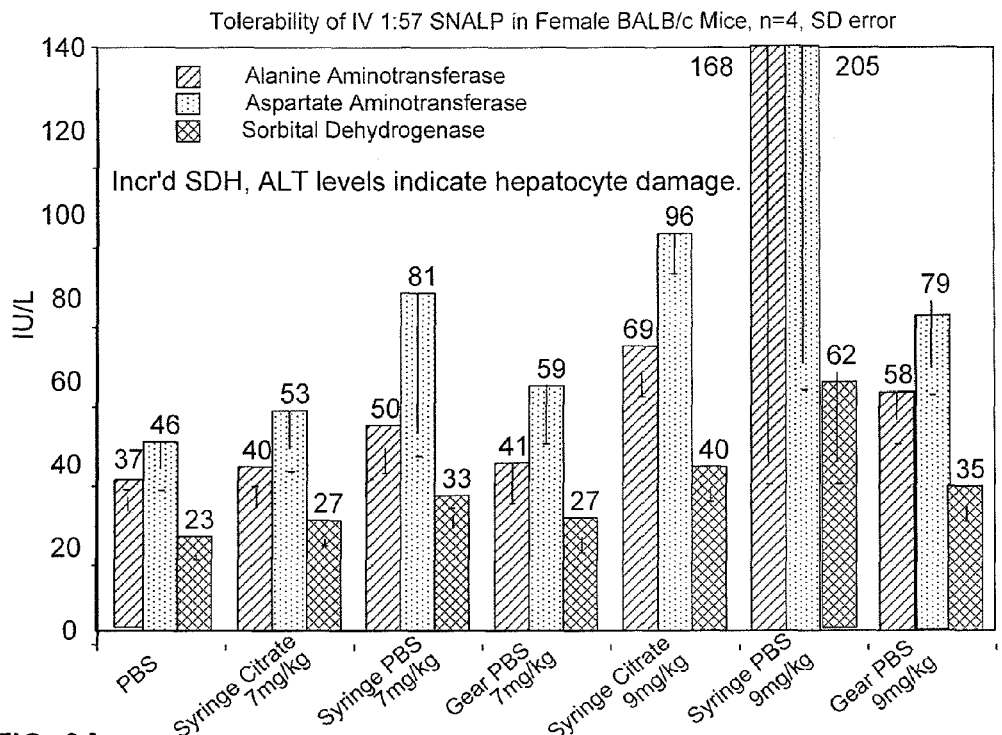
FIG. 6A (expressed as IU/L) and FIG. 6B (expressed as x-Fold Upper Limit of Normal) illustrate data demonstrating that the tolerability of 1:57 SNALP containing ApoB siRNA prepared by citrate buffer versus PBS direct dilution did not differ significantly in terms of blood clinical chemistry parameters.
Figure 6B:
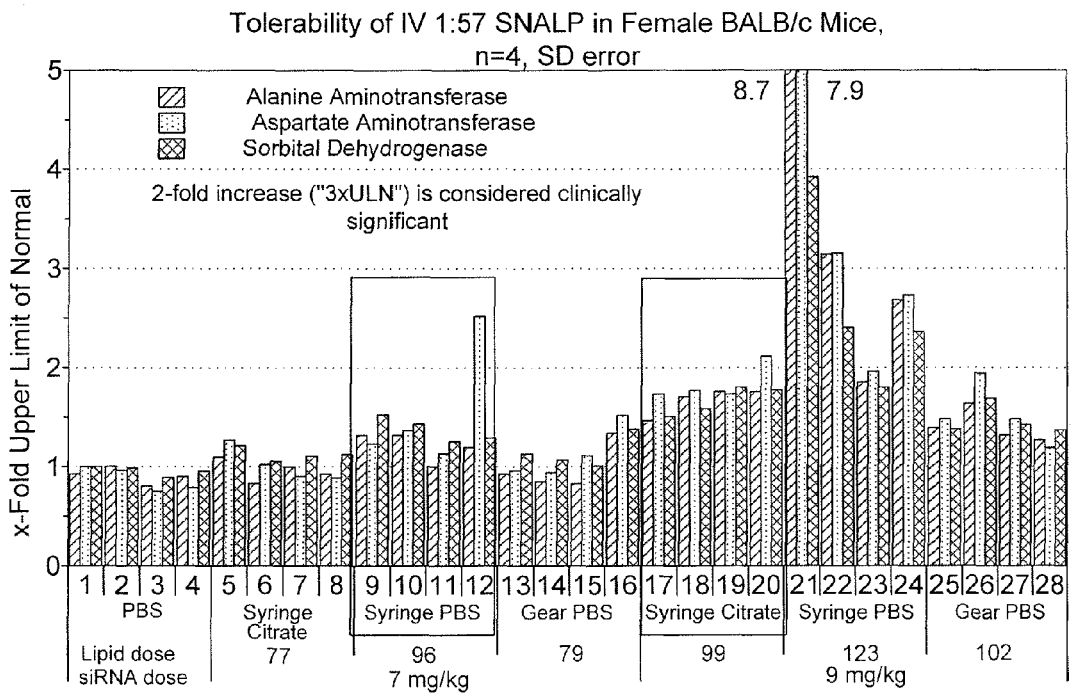

There was no body weight loss or change in animal appearance/behavior upon administration of the 1:57 SNALP formulations. FIG. 6 shows that the tolerability of SNALP prepared by citrate buffer versus PBS direct dilution did not differ significantly in terms of blood clinical chemistry parameters. There was a tolerability difference between syringe citrate and syringe PBS at constant siRNA dosage, but that was likely an artifact dependent on the different final lipid:drug (L:D) ratios of these two preparations.

Figure 7A:
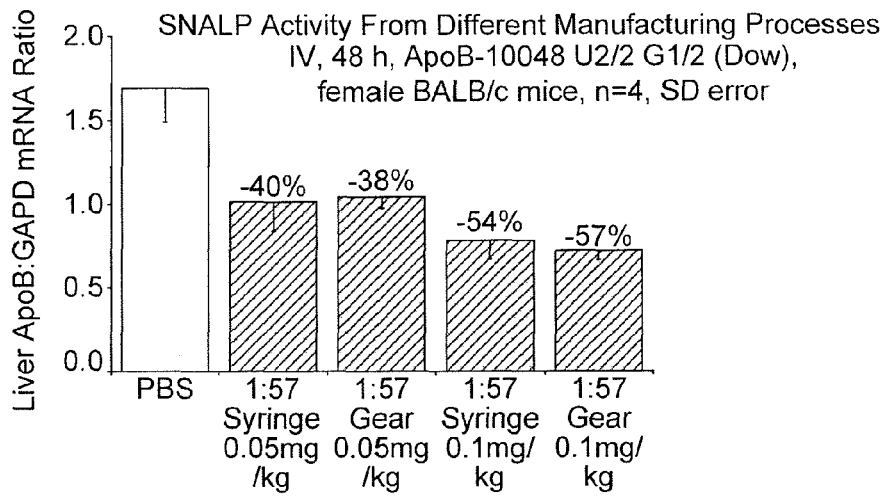
FIG. 7A (expressed as liver ApoB:GAPD mRNA ratio), FIG. 7B (expressed as relative plasma ApoB-100 concentration), and FIG. 7C (expressed as plasma total cholesterol illustrate data demonstrating that the efficacy of 1:57 SNALP containing ApoB siRNA prepared by gear pump was similar to the same SNALP prepared by syringe press.
Figure 7B:
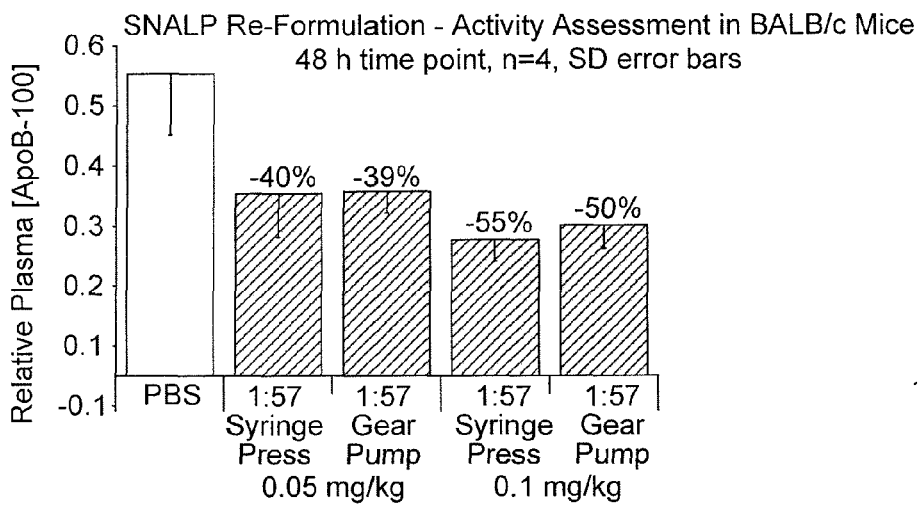
Figure 7C:
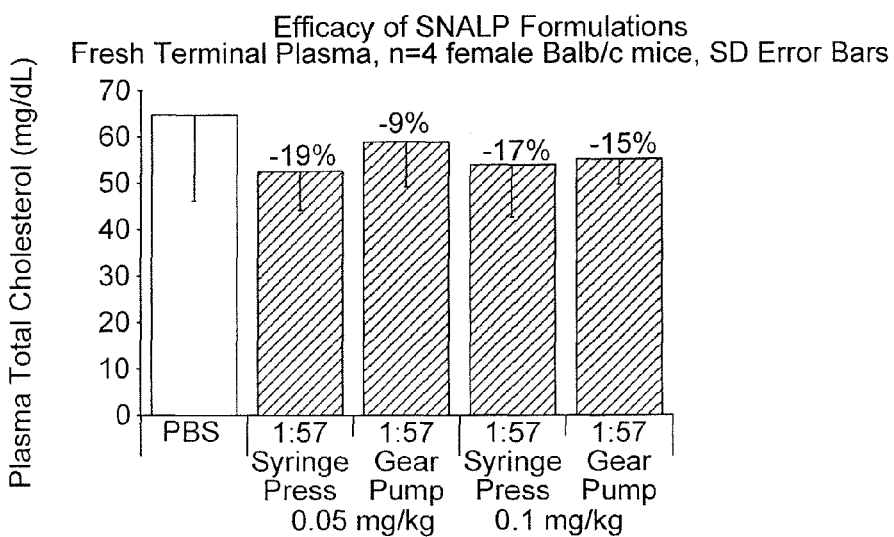

FIG. 7 shows that the efficacy of the 1:57 SNALP prepared by gear pump was similar to the same SNALP prepared by syringe press. The tolerability profile was improved with the gear pump process, which could be attributed to increased initial encapsulation rate and decreased final L:D ratio.

Example 8

In Vivo Silencing of ApoB Expression Using 1:57 SNALP Prepared Via a Direct Dilution or In-Line Dilution Process This study illustrates a comparison of the tolerability and efficacy of the 1:57 SNALP formulation with ApoB-targeting siRNA as prepared by a direct dilution or in-line dilution process at an input lipid to drug ratio of 6:1 or 9:1.

Experimental Design

Animal Model: Female BALB/c mice, 7 wks old.

siRNA payload: ApoB10048 U2/2 G1/2 siRNA.

CBC/Diff:

| | # | | IV Dosage | |
|---|---|---|---|---|
| Group | Mice | Test Article | Encap. siRNA | Total Lipid |
| 1 | 3 | PBS | — | — |
| 2 | 3 | 1\|57 SNALP (9:1) | 7 mg/kg | 71 mg/kg |
| 3 | 3 | 1\|57 SNALP (9:1) | 11 mg/kg | 112 mg/kg |

Clinical Chemistry:

| | # | | IV Dosage | |
|---|---|---|---|---|
| Group | Mice | Test Article | Encap. siRNA | Total Lipid |
| 4 | 4 | PBS | — | — |
| 5 | 4 | 1\|57 SNALP (9:1) | 9 mg/kg | 92 mg/kg |
| 6 | 4 | 1\|57 SNALP (9:1) | 11 mg/kg | 112 mg/kg |
| 7 | 4 | (6:1) New 1\|57 SNALP | 11 mg/kg | 78 mg/kg |
| 8 | 4 | (6:1) New 1\|57 SNALP | 13 mg/kg | 93 mg/kg |
| 9 | 4 | (6:1) New 1\|57 SNALP | 15 mg/kg | 107 mg/kg |
| 10 | 4 | (6:1) New 1\|57 SNALP | 17 mg/kg | 121 mg/kg |
| 11 | 4 | 1\|57 SNALP (9:1) | 11 mg/kg | 112 mg/kg |

Activity:

| | # | | IV Dosage | |
|---|---|---|---|---|
| Group | Mice | Test Article | Encap. siRNA | Total Lipid |
| 12 | 4 | PBS | — | — |
| 13 | 4 | 1\|57 SNALP (9:1) | 0.05 mg/kg | 0.51 mg/kg |
| 14 | 4 | 1\|57 SNALP (9:1) | 0.1 mg/kg | 1.02 mg/kg |
| 15 | 4 | 1\|57 SNALP (9:1) | 0.2 mg/kg | 2.04 mg/kg |
| 16 | 4 | (6:1) New 1\|57 SNALP | 0.05 mg/kg | 0.36 mg/kg |
| 17 | 4 | (6:1) New 1\|57 SNALP | 0.1 mg/kg | 0.71 mg/kg |
| 18 | 4 | (6:1) New 1\|57 SNALP | 0.2 mg/kg | 1.42 mg/kg |
| 19 | 4 | (6:1) New 1\|57 SNALP | 0.4 mg/kg | 2.85 mg/kg |

Formulation:

Formulations are provided at 0.005 to 1.7 mg siRNA/mL, 0.22 μm filter sterilized in crimp top vials.

Formulation Details:

1. "1|57 SNALP" used in this study is lipid composition 1.4:57.1:7.1:34.3 as described in molar percentages of PEG-C-DMA, DLinDMA, DPPC, and cholesterol (in that order). This formulation was prepared by gear pump at an input lipid to drug ratio of 9:1 (28 mM lipids) or 6:1 (14 mM lipids).

2. siRNA used in this study is apoB-10048 U2/2 G1/2 siRNA.

Formulation Summary:

| | 1\|57 SNALP Gear PBS | Particle Size | | | Final L:D |
|---|---|---|---|---|---|
| | In-Line | Zavg (nm) | Poly | % Encap | (mg:mg) |
| 322-051407-1 | Input 9:1 | 78 | 0.07 | 93 | 10.2 |
| 322-051407-2 | Input 6:1 | 81 | 0.05 | 92 | 7.1 |

Procedures

Treatment:

Just prior to the first treatment, animals are weighed and dose amounts are calculated based on the weight of individual animals (equivalent to 10 mL/kg, rounded to the nearest 10 μl). Test article is administered by IV injection through the tail vein once on Day 0 (1 dose total per animal). Body weight is measured daily (every 24 h) for the duration of the study. Cage-side observations are taken daily in concert with body weight measurements and additionally as warranted.

Endpoint:

Animals are sacrificed on Day 1, 24 h after test article administration (Grps 1-10) or on Day 2, 48 h after test article administration (Grps 11-19).

Groups 1-3:

Blood is collected by cardiac puncture upon sacrifice. Whole amount is collected into an EDTA microtainer, mixed immediately to prevent coagulation, and sent for analysis of CBC/Diff profile. Perform brief necropsy.

Groups 4-11:

Blood is collected by cardiac puncture into a SST microtainer for serum. Clot for 30 (to 60) min at room temp., centrifuge for 5 min at 16,000×g & 16° C., invert to confirm centrifugation is complete, and store at 4° C. Analyze complete small-animal clinical chemistry panel plus AST and SDH. Top priority list: ALT, AST, SDH, Bilirubin, Alkaline Phosphatase, GGT, BUN, CPK, Glucose. Secondary priority list: Creatinine, Albumin, Globulin, Total Protein. Perform brief necropsy.

Groups 12-19:

Blood is collected by cardiac puncture and processed for plasma: immediately centrifuge for 5 min at 16,000×g (at 16° C.). Record any observations of unusual plasma appearance. Pipette off clear plasma supernatant into a clean microfuge tube and store at −80° C. The following tissues are removed: liver. The liver is not weighed; the bottom (unattached) half of the left liver lobe is detached and submerged in >5 volumes of RNAlater (<0.3 g in 1.5 mL RNAlater in 2.0 mL tube), stored at least 16 hours at 4° C. prior to analysis and long term storage at −80° C. Formulations are expected to be well tolerated. Mice which exhibit signs of distress associated with the treatment are terminated at the discretion of the vivarium staff.

Termination:

Mice are anaesthetized with a lethal dose of ketamine/xylazine; then cardiac puncture is performed followed by cervical dislocation.

Data Analysis:

Tolerability of treatment regime is monitored by animal appearance and behavior, and body weight. Blood clinical chemistry and CBC/Diff profile is measured by automated analyzer. Liver ApoB mRNA is measured using the QuantiGene Assay.

Plasma ApoB-100 is measured using ELISA. Plasma total cholesterol is measured using a standard enzymatic assay.

Results

Figure 8:
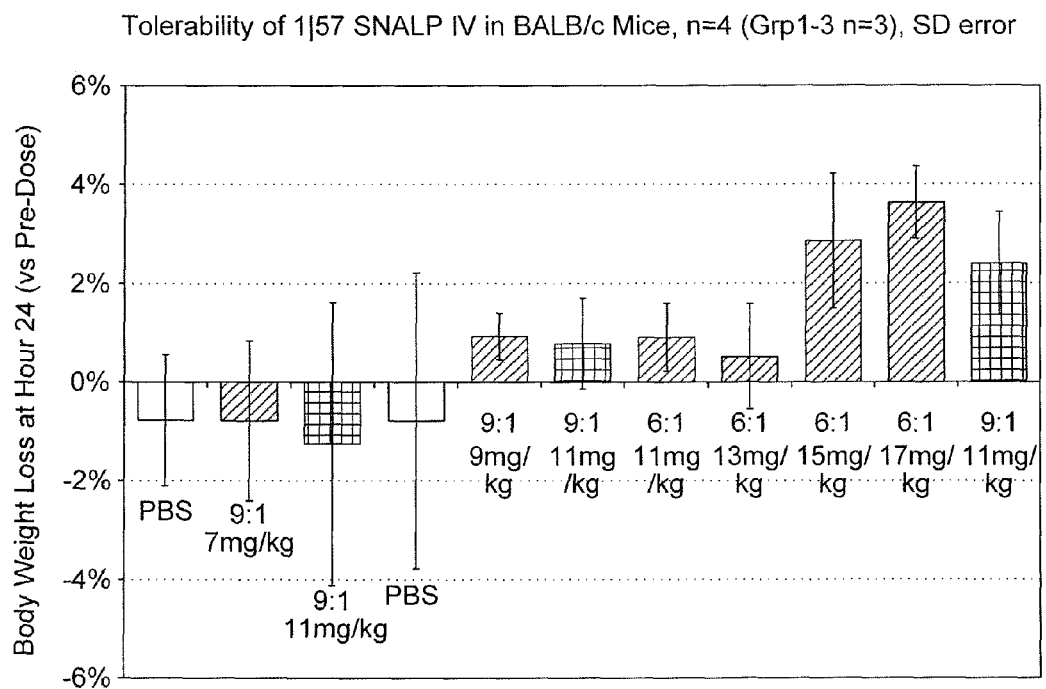
FIG. 8 illustrates data demonstrating that there was very little effect on body weight 24 hours after administration of 1:57 SNALP containing ApoB siRNA.

Tolerability:

FIG. 8 shows that there was very little effect on body weight 24 hours after 1:57 SNALP administration. The maximum weight loss of 3.6±0.7% was observed at the highest drug dose of 17 mg/kg. There was also no obvious change in animal appearance/behavior at any of the dosages tested.

Figure 9:
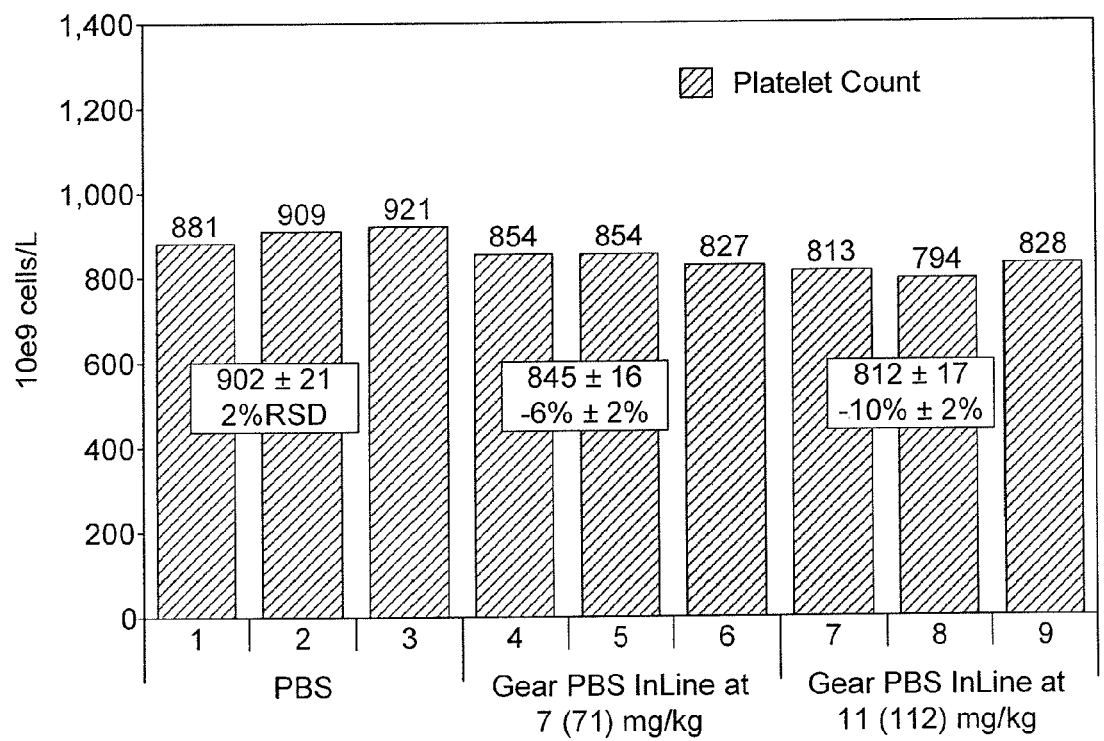
FIG. 9 illustrates data demonstrating that there were no obvious changes in platelet count after administration of 1:57 SNALP containing ApoB siRNA.

FIG. 9 shows that there were no obvious changes in platelet count. Reduction of platelets can cause the mean platelet volume to increase as the body produces new platelets in compensation for the treatment-related decrease. Under the conditions of this study, the mean platelet volume did not change in SNALP-treated groups.

Figure 10A:
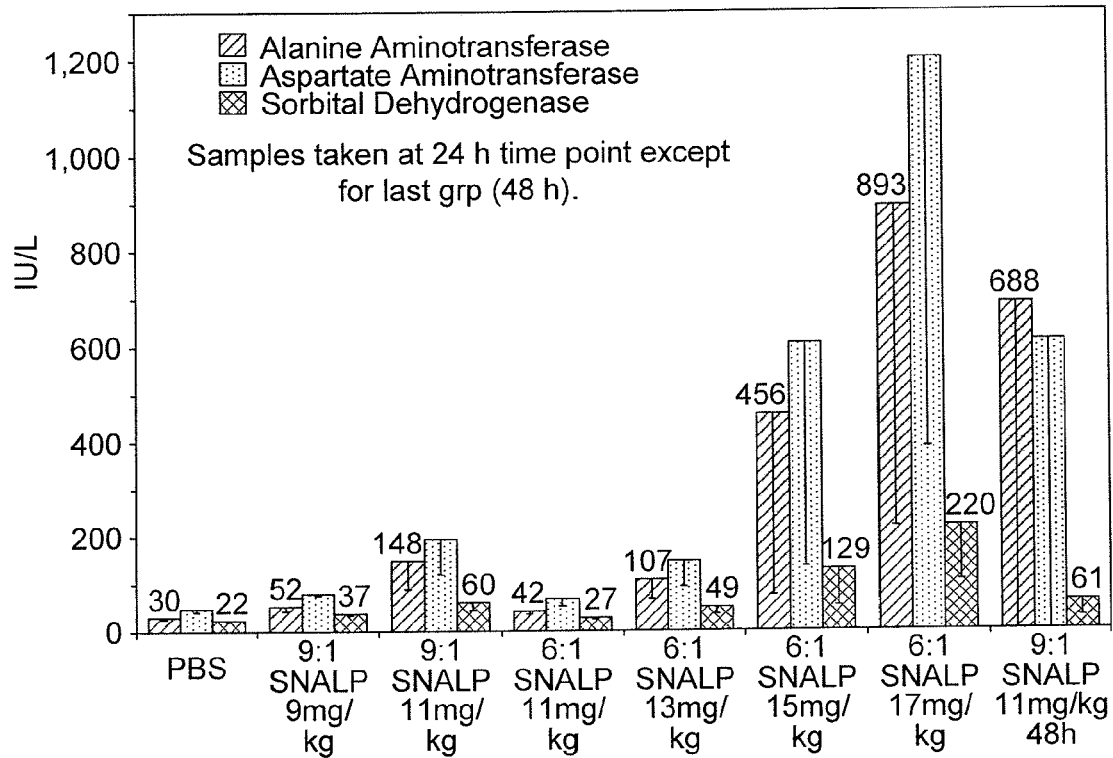
FIG. 10A (expressed as IU/L) and FIG. 10B (expressed as x-Fold Upper Limit of Normal) illustrate data demonstrating that clinically significant liver enzyme elevations (3xULN) occurred at particular drug dosages of 1:57 SNALP containing ApoB siRNA.
Figure 10B:
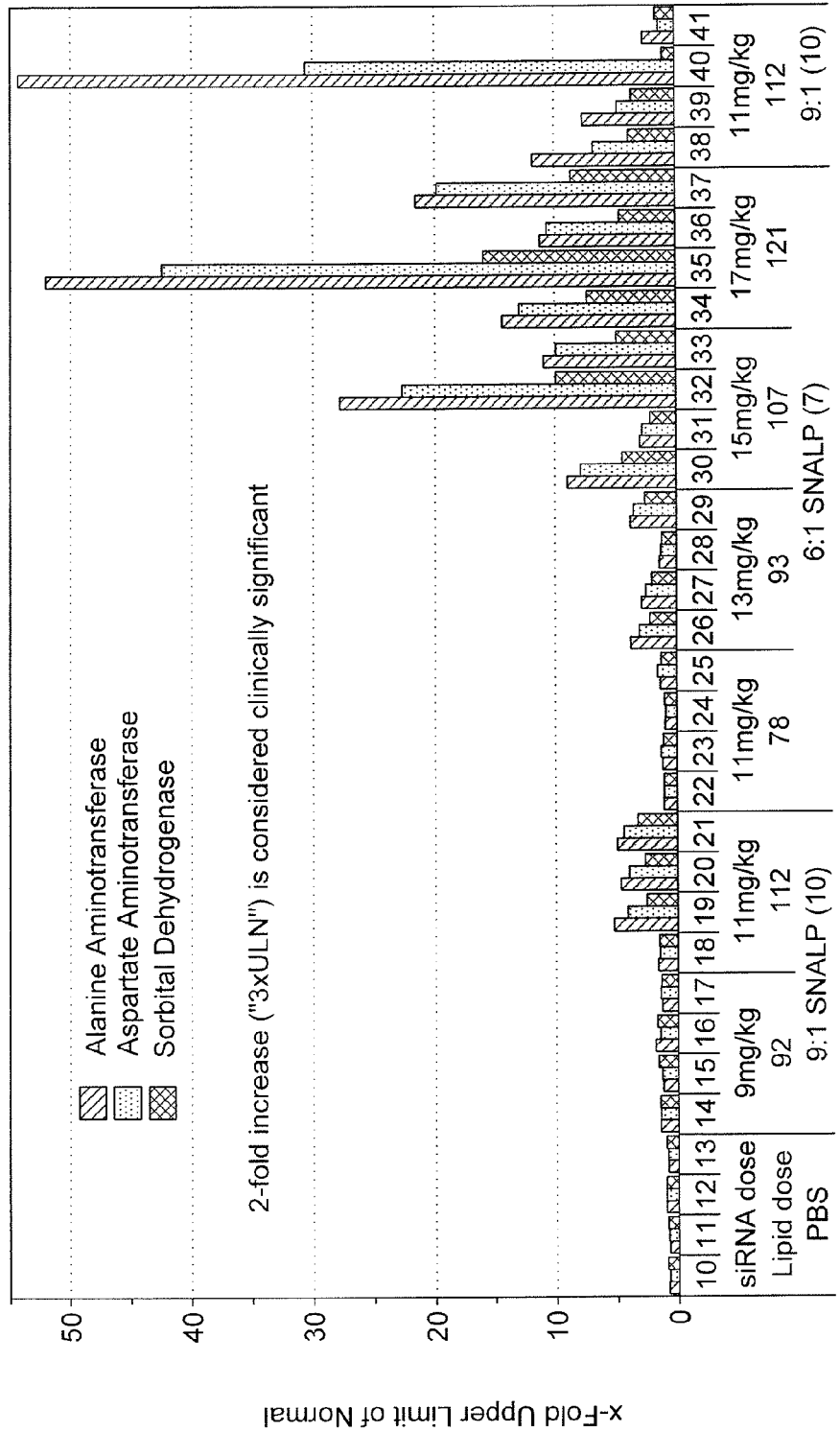

FIG. 10 shows that clinically significant liver enzyme elevations (3xULN) occurred at drug dosages of 11 mg/kg for 1:57 SNALP at a lipid:drug (L:D) ratio of 10, and at 13 mg/kg at a L:D of 7. A slight dose response trend upwards in plasma total protein and globulin was also observed.

Figure 11A:
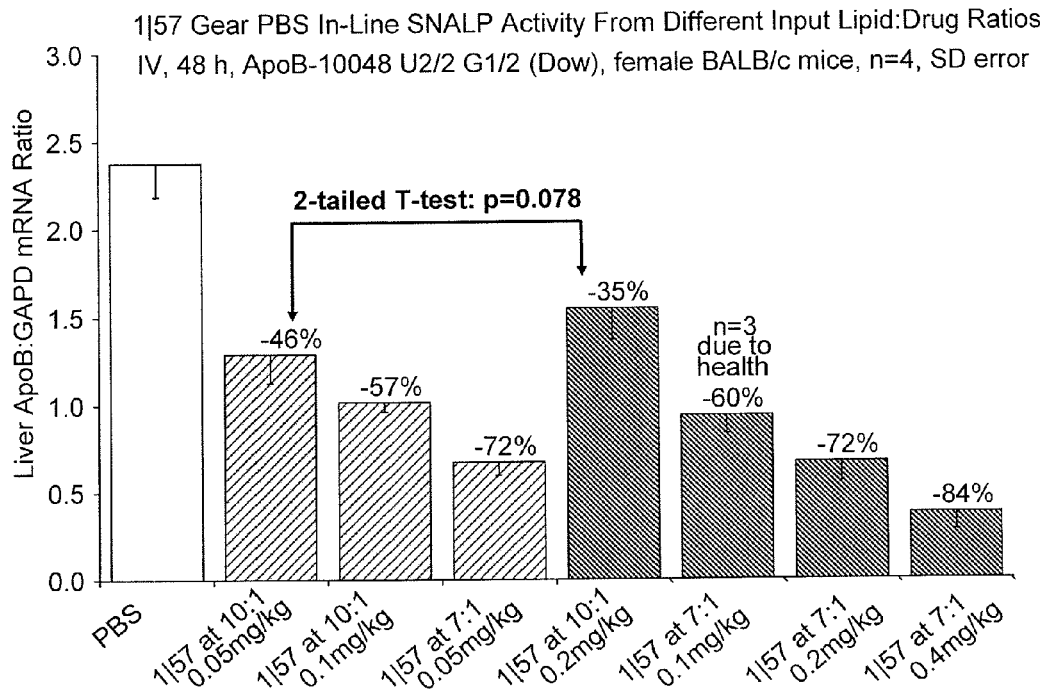
FIG. 11A (expressed as liver ApoB:GAPD mRNA ratio) and FIG. 11B (expressed as relative plasma ApoB-100 concentration illustrate data demonstrating that the potency of the lower lipid:drug (L:D) 1:57 SNALP containing ApoB siRNA was as good as that of the higher L:D SNALP at the tested drug dosages.
Figure 11B:
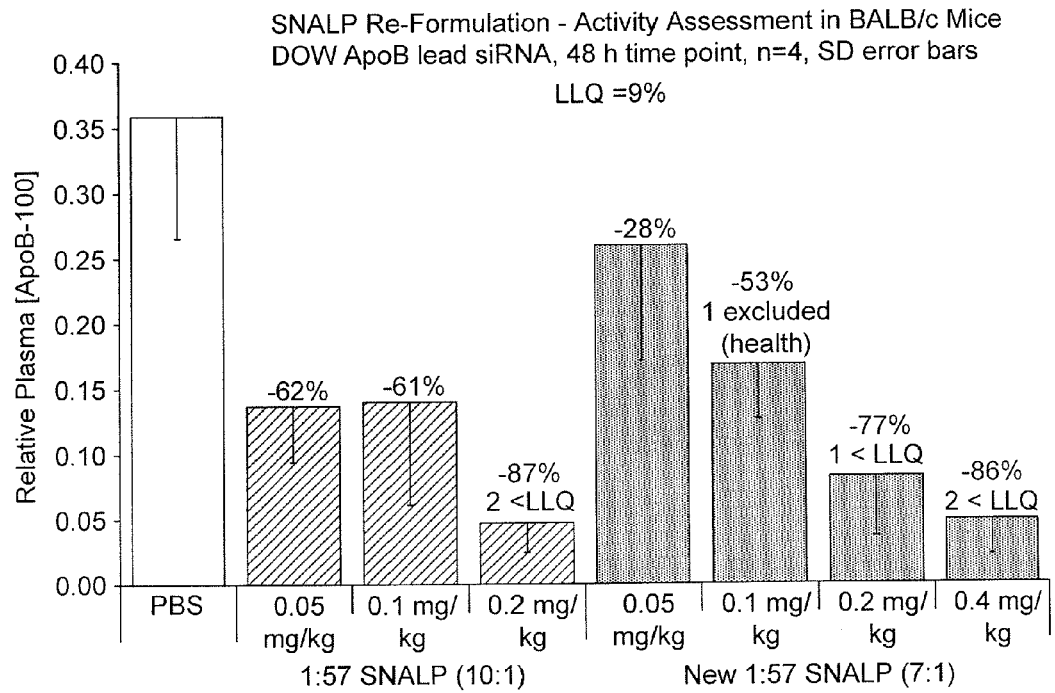

Efficacy:

FIG. 11 shows that based on the liver mRNA QuantiGene analysis, the potency of the lower L:D SNALP was as good as that of the higher L:D SNALP at the tested drug dosages. In fact, the ApoB silencing activity was identical at the 0.05 and 0.1 mg/kg dosages. As such, the potency of the 1:57 SNALP at a 6:1 input L:D ratio (final ratio of 7:1) was similar to the potency of the 1:57 SNALP at a 9:1 input L:D ratio (final ratio of 10:1) at reducing ApoB expression.

Figure 12:
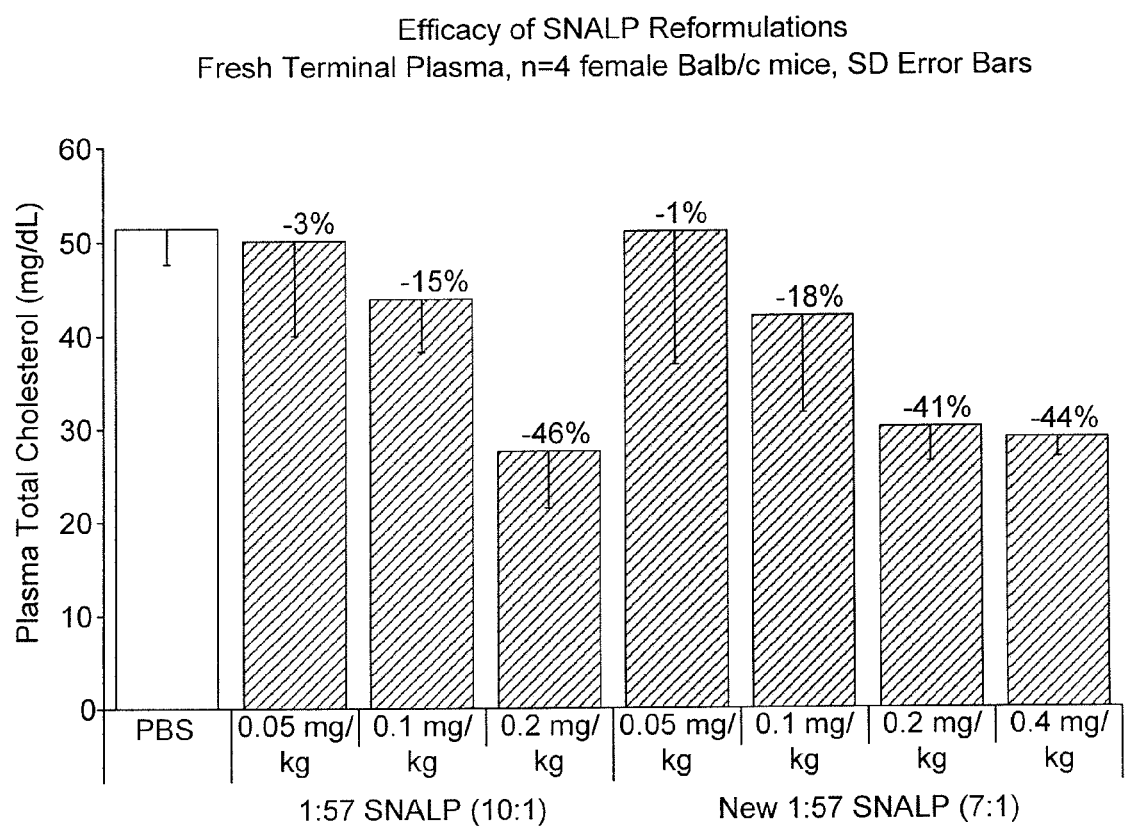
FIG. 12 illustrates data demonstrating that ApoB protein and total cholesterol levels were reduced to a similar extent by 1:57 SNALP containing ApoB siRNA at a 6:1 input L:D ratio (final ratio of 7:1) and 1:57 SNALP at a 9:1 input L:D ratio (final ratio of 10:1).

FIG. 12 shows that ApoB protein and total cholesterol levels were reduced to a similar extent by the 1:57 SNALP at a 6:1 input L:D ratio (final ratio of 7:1) and the 1:57 SNALP at a 9:1 input L:D ratio (final ratio of 10:1).

Therapeutic Index:

This study demonstrates that both the 1:57 SNALP at a 6:1 input L:D ratio (final ratio of 7:1) and the 1:57 SNALP at a 9:1 input L:D ratio (final ratio of 10:1) caused about 60% ApoB liver mRNA silencing with a drug dose of 0.1 mg/kg. Interpolating from the available data points in FIG. 10, a 10:1 final L:D ratio at 10 mg/kg may cause a similar degree of enzyme elevation as a 7:1 final L:D ratio at 13 mg/kg. Using these activity and toxicity points, the therapeutic index for the 1:57 SNALP at a 10:1 final L:D ratio is (10 mg/kg)/(0.1 mg/kg)=100 and the therapeutic index for the 1:57 SNALP at a 7:1 final L:D ratio is (13 mg/kg)/(0.1 mg/kg)=130. Using this dataset, the therapeutic index for the 1:57 SNALP at a 7:1 final L:D ratio is 30% greater than the therapeutic index for the 1:57 SNALP at a 10:1 final L:D ratio.

Example 9

In Vivo Silencing of PLK-1 Expression Using 1:57 SNALP Increases Survival of Hep3B Tumor-Bearing Mice SNALP containing polo-like kinase 1 (PLK-1) siRNA (1:57 SNALP formulation: 1.4% PEG-cDMA; 57.1% DLinDMA; 7.1% DPPC; and 34.3% cholesterol) were tested for their effects on the survival of CD1 nu/nu mice bearing Hep3B liver tumors. PLK-1 is a serine/threonine kinase containing two functional domains: (1) a kinase domain; and (2) a polo-box domain (see, e.g., Barr et al., Nat. Rev. Mol. Cell Biol., 5:429-440 (2004)). The activity and cellular concentration of PLK-1 are crucial for the precise regulation of cell division. PLK-1 is overexpressed in many cancer types including hepatoma and colon cancer, and PLK-1 expression often correlates with poor patient prognosis. Overexpression of PLK-1 (wild-type or kinase inactive) results in multinucleation (genetic instability). Hyperactive PLK-1 overrides the DNA damage checkpoint. Constitutive PLK-1 expression causes transformation of NIH 3T3 cells. PLK-1 phosphorylates the p53 tumor suppressor, thereby inhibiting the pro-apoptotic effects of p53. The PLK-1 siRNA used in this study are provided in Table 8. The modifications involved introducing 2'OMe-uridine or 2'OMe-guanosine at selected positions in the sense and antisense strands of the PLK-1 siRNA sequence, in which the siRNA duplex contained less than about 20% 2'OMe-modified nucleotides.

TABLE 8 siRNA duplexes comprising sense and antisense PLK-1 RNA polynucleotides.

| siRNA | PLK-1 siRNA Sequence | SEQ ID NO: | % Modified in DS Region |
|---|---|---|---|
| PLK1424 U4/GU | 5'-AGAUCACCCUCCUUAAAUANN-3'<br>3'-NNUCUAGUGGGAGGAAUUUAU-5' | 5<br>6 | 6/38 = 15.8% |
| PLK1424 U4/G | 5'-AGAUCACCCUCCUUAAAUANN-3'<br>3'-NNUCUAGUGGGGAGGAAUUUAU-5' | 5<br>7 | 7/38 = 18.4% |

Column 1: The number after "PLK" refers to the nucleotide position of the 5' base of the sense strand relative to the start codon (ATG) of the human PLK-1 mRNA sequence NM_005030.
Column 2: 2'-O-methyl (2'OMe) nucleotides are indicated in bold and underlined. The siRNA duplex can alternatively or additionally comprise 2'-deoxy-2'-fluoro (2'F) nucleotides, 2'-deoxy nucleotides, 2'-O-(2-methoxyethyl) (MOE) nucleotides, and/or locked nucleic acid (LNA) nucleotides. N = deoxythymidine (dT) nucleotide, uridine (U) ribonucleotide, or ribonucleotide having complementarity to the target sequence or the complementary strand thereof.
Column 3: The number and percentage of modified nucleotides in the double-stranded (DS) region of the siRNA duplex are provided.

Experimental Groups

20 CD1 nu/nu mice were seeded as follows:

| Group | # Mice | Tumor seeding | SNALP | # Mice | SNALP dosing IV | SNALP dose | Sacrifice | Assay |
|---|---|---|---|---|---|---|---|---|
| A | 20 to seed | I.H. 1.5 × 10⁶ Hep3B | Luc 1:57<br>PLK 1424 1:57 | 9<br>9 | Days 11, 14, 17, 21, 25, 28, 32, 35, 39, 42 | 10 × 2 mg/kg | When moribund | Survival Body Weights |
| B | | | | | | | | |

Test Articles

All samples were filter-sterilized prior to dilution to working concentration. All tubes were labeled with the formulation date, lipid composition, and nucleic acid concentration. SNALP samples were provided at 0.2 mg/ml nucleic acid. A minimum of 20 ml of each SNALP was required to perform the study. Formulations for this study contained:

| Group | Test Article Description |
|---|---|
| A | Luc U/U SNALP 1:57 (28 mM lipid) |
| B | PLK1424 U4/GU SNALP 1:57 (28 mM lipid)<br>PLK1424 U4/G SNALP 1:57 (28 mM lipid) |

Procedures

| | |
|---|---|
| Day 0 | Mice will receive Anafen by SC injection (100 µg in 20 µl saline) immediately prior to surgery. Individual mice are anesthetized by isoflourane gas inhalation and eye lube applied to prevent excessive eye drying. While maintained under gas anesthesia from a nose cone, a single 1.5 cm incision across the midline will be made below the sternum. The left lateral hepatic lobe is then exteriorized using an autoclaved cotton wool bud. 25 µl of tumor cells suspended in PBS is injected into the lobe at a shallow angle using a leur tip Hamilton syringe (50 µl) and 30G (⅜") needle. Cells will be injected slowly (~30 s) and a swab applied to the puncture wound immediately after needle withdrawal. After any bleeding has stopped (~1 min), the incision is closed with 5-6 sutures in the muscle wall and 3-4 skin clips. Cell suspensions will be thoroughly mixed immediately prior to each injection. Mice will recover from anesthesia in a clean cage lined with paper towel and monitored closely for 2-4 hours. Animals are then returned to normal housing. |
| Day 1 | All mice will be lightly anesthetized by isoflourane gas and the sutures examined. Animals will then receive Anafen by SC injection (100 µg in 20 µl saline). |
| Day 10 | Mice will be randomized into the appropriate treatment groups. |
| Day 11 | Groups A, B - Day 11: All Animals will be administered SNALP at 2 mg/kg by IV injection via the lateral tail vein. Mice will be dosed according to body weight (10 ml/kg). Dosing will be repeated for 5 consecutive days based on initial weight. |
| Day 14-35 | Groups A, B - Days 14, 17, 21, 25, 28, 32, 35: All Animals will be re-administered SNALP at 2 mg/kg by IV injection via the lateral tail vein. Mice will be dosed according to body weight (10 ml/kg). Body weights Groups: Mice will be weighed on the day of dosing for 5 weeks, then twice weekly until close of the study. Endpoint: Tumor burden and formulations are expected to be well tolerated. Mice that exhibit signs of distress associated with the treatment or tumor burden are terminated at the discretion of the vivarium staff. |
| Termination: | Mice are anesthetized with a lethal dose of ketamine/xylazine followed by cervical dislocation. |
| Data Analysis: | Survival and body weights are assayed. |

Results

Figure 13:
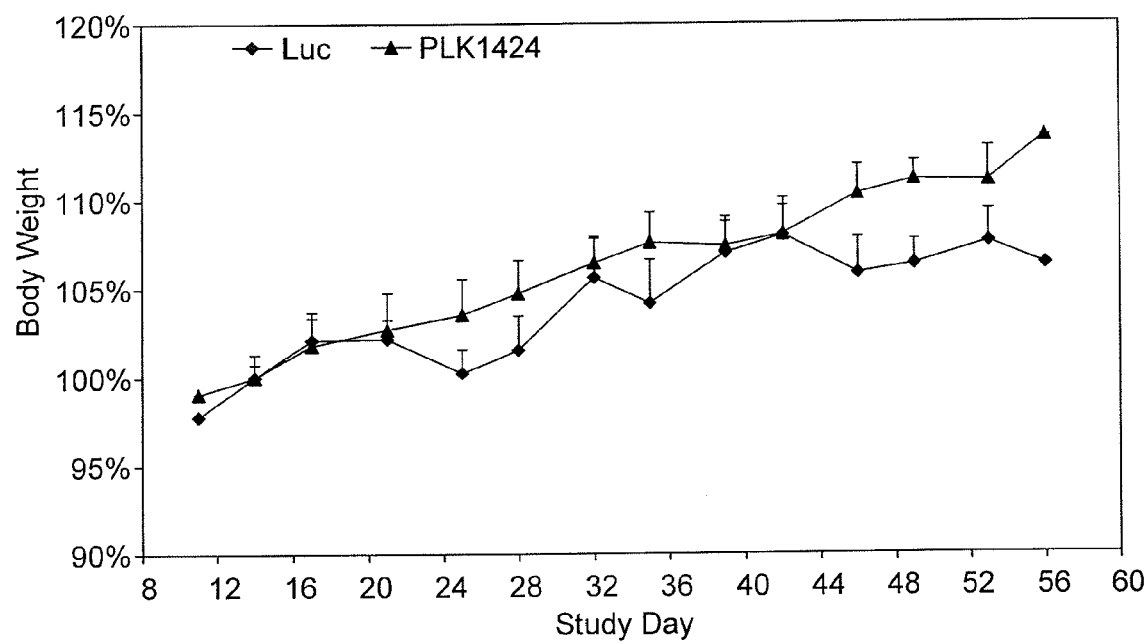
FIG. 13 illustrates data demonstrating that a treatment regimen of 1:57 SNALP with siRNA targeting PLK-1 is well tolerated with no apparent signs of treatment related toxicity in mice bearing Hep3B liver tumors.

FIG. 13 shows the mean body weights of mice during therapeutic dosing of PLK1424 SNALP in the Hep3B intrahepatic (I.H.) tumor model. The treatment regimen was well tolerated with no apparent signs of treatment-related toxicity.

Figure 14:
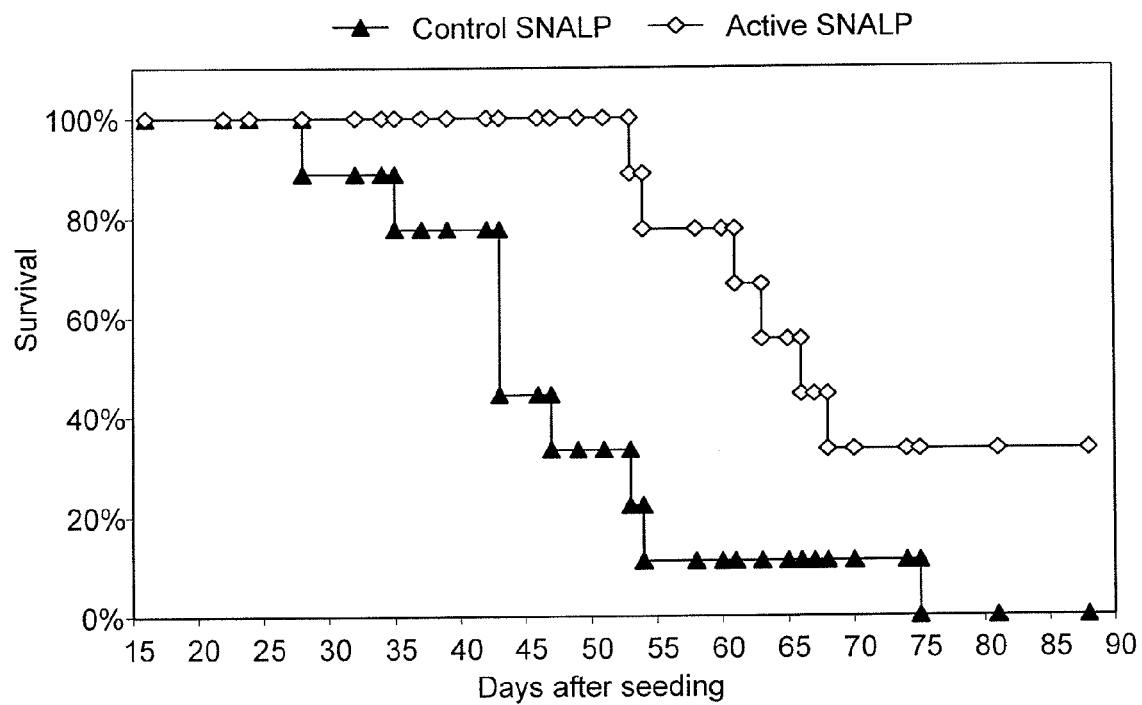
FIG. 14 illustrates data demonstrating that treatment with 1:57 SNALP containing PLK-1 siRNA caused a significant increase in the survival of Hep3B tumor-bearing mice.

FIG. 14 shows that treatment with 1:57 SNALP-formulated PLK1424 caused a significant increase in the survival of Hep3B tumor-bearing mice. This in vivo anti-tumor effect was observed in the absence of any apparent toxicity or immune stimulation.

Example 10

In vivo Silencing of PLK-1 Expression Using 1:57 SNALP Induces Tumor Cell Apoptosis in Hep3B Tumor-Bearing Mice The objectives of this study were as follows:
1. To determine the level of mRNA silencing in established Hep3B liver tumors following a single IV administration of PLK1424 SNALP.
2. To confirm the mechanism of mRNA silencing by detecting specific RNA cleavage products using RACE-PCR.
3. To confirm induction of tumor cell apoptosis by histopathology.

The 1:57 SNALP formulation (1.4% PEG-cDMA; 57.1% DLinDMA; 7.1% DPPC; and 34.3% cholesterol) was used for this study.

Experimental Groups

20 SCID/beige mice were seeded as follows:

| Group | # Mice | Tumor seeding | SNALP | # Mice | SNALP dosing IV | Sacrifice | Assay |
|---|---|---|---|---|---|---|---|
| A | 20 to seed | I.H. 1 × 10⁶ Hep3B | PBS | 6 | 1 × 2 mg/kg Day 20 | 24 h after treatment | Tumor QG |
| B | | | Luc 1:57 | 7 | | | Tumor RACE-PCR |
| C | | | PLK 1424 1:57 | 7 | | | Histopathology |

Test Articles

All samples were filter-sterilized prior to dilution to working concentration. All tubes were labeled with the formulation date, lipid composition, and nucleic acid concentration. SNALP samples were provided at 0.2 mg/ml nucleic acid. A minimum of 2 ml of SNALP was required to perform the study. Formulations for this study contained:

| Group | Test Article Description |
|---|---|
| A | PBS |
| B | Luc U/U 1:57 SNALP |
| C | PLK1424 U4/GU 1:57 SNALP |

Procedures

| | |
|---|---|
| Day 0 | Mice will receive Anafen by SC injection (100 μg in 20 μl saline) immediately prior to surgery. Individual mice are anesthetized by isoflourane gas inhalation and eye lube applied to prevent excessive eye drying. While maintained under gas anesthesia from a nose cone, a single 1.5 cm incision across the midline will be made below the sternum. The left lateral hepatic lobe is then exteriorized using an autoclaved cotton wool bud. 25 μl of tumor cells suspended in PBS is injected into the lobe at a shallow angle using a leur tip Hamilton syringe (50 μl) and 30G (⅜") needle. Cells will be injected slowly (~30 s) and a swab applied to the puncture wound immediately after needle withdrawal. After any bleeding has stopped (~1 min), the muscle wall incision is closed with 5-6 sutures. The skin incision is then closed with 3-4 metal skin clips. Cell suspensions will be thoroughly mixed immediately prior to each injection. Mice will recover from anesthesia in a clean cage lined with paper towel and monitored closely for 2-4 hours. Animals are then returned to normal housing. |
| Day 1 | All mice will be lightly anesthetized by isoflourane gas and the sutures examined. Animals will then receive Anafen by SC injection (100 μg in 20 μl saline). |
| Day 7 | Mice will be randomized into the appropriate treatment groups. |
| Day 20 | Groups A-C: Mice will be weighed and then administered either PBS, Luc, or PLK1424 SNALP by IV injection via the lateral tail vein. SNALP will be dosed at 2 mg/kg or equivalent volume (10 ml/kg) according to body weight. |
| Day 21 | Groups A-C: All mice will be weighed and then euthanized by lethal anesthesia. Tumor bearing liver lobes from all mice in each group will be weighed and collected into RNALater for RNA analysis. Endpoint: Tumor burden and formulations are expected to be well tolerated. Mice that exhibit signs of distress associated with the treatment or tumor burden are terminated at the discretion of the vivarium staff. |
| Termination: | Mice are anaesthetized with a lethal dose of ketamine/xylazine followed by cervical dislocation. |
| Data Analysis: | mRNA analysis of liver tumors by bDNA (QG) assay and RACE-PCR. Tumor cell apoptosis by histopathology. |

Results

Body weights were monitored from Day 14 onwards to assess tumor progression. On Day 20, 6 mice showing greatest weight loss were randomized into each of the 3 groups and treated. All six mice had substantial-large I.H. tumors at sacrifice (Day 21). Treatment of the remaining 14 mice was therefore initiated on the Day 21 (sacrifice Day 22). 10/14 mice had substantial tumors; 2/14 mice had small/probable tumors; and 2/14 mice had no visible tumor burden.

Figure 15:
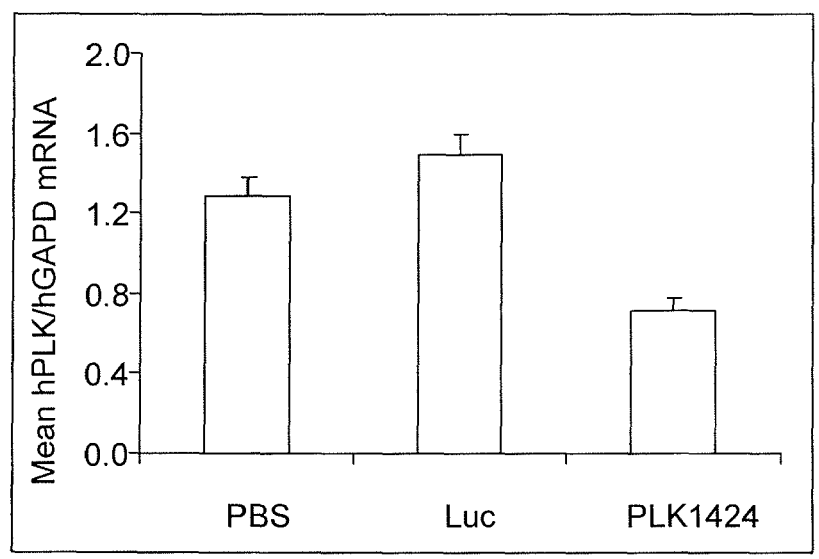
FIG. 15 illustrates data demonstrating that treatment with 1:57 SNALP containing PLK-1 siRNA reduced PLK-1 mRNA levels by 50% in intrahepatic Hep3B tumors growing in mice 24 hours after SNALP administration.

FIG. 15 shows data from Quantigene assays used to measure human (tumor)-specific PLK-1 mRNA levels. A single 2 mg/kg dose of 1:57 SNALP reduced PLK-1 mRNA levels by about 50% in intrahepatic Hep3B tumors growing in mice.

Figure 16:
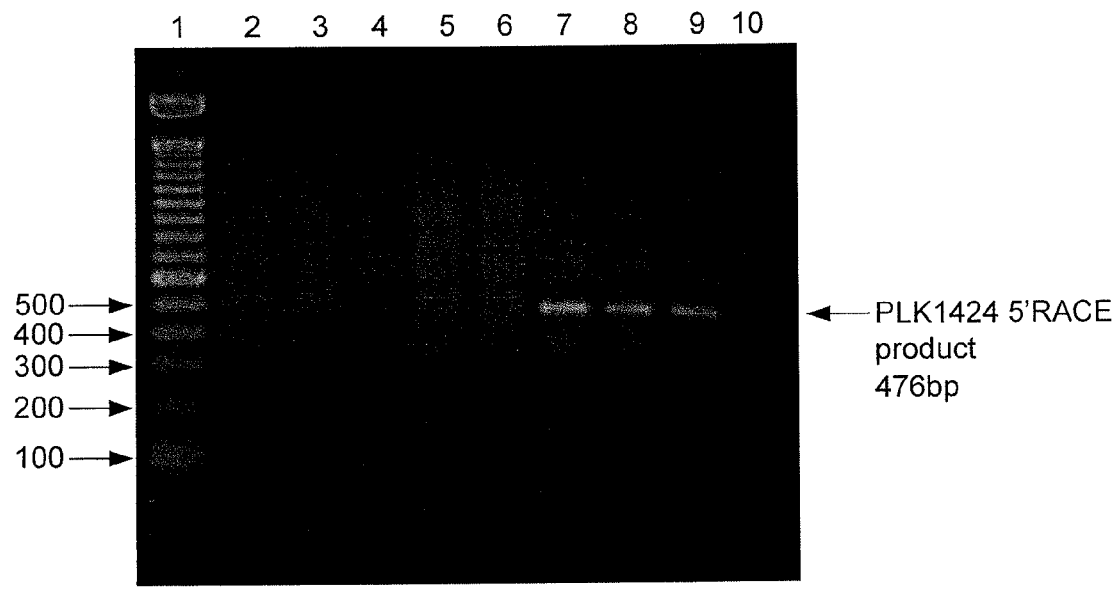
FIG. 16 illustrates data demonstrating that a specific cleavage product of PLK-1 mRNA was detectable by 5' RACE-PCR in mice treated with 1:57 SNALP containing PLK-1 siRNA. 10 µl PCR product/well were loaded onto a 1.5% agarose gel. Lane Nos.: (1) molecular weight (MW) marker; (2) PBS mouse 1; (3) PBS mouse 2; (4) PBS mouse 3; (5) Luc SNALP mouse 1; (6) Luc SNALP mouse 2; (7) PLK SNALP mouse 1; (8) PLK SNALP mouse 2; (9) PLK SNALP mouse 3; and (10) no template control.

FIG. 16 shows that a specific cleavage product of PLK-1 mRNA was detectable in mice treated with PLK1424 SNALP by 5' RACE-PCR. No specific PCR product was detectable in mice treated with either PBS or control (Luc) SNALP. Nucleotide sequencing of the PCR product confirmed the predicted cleavage site by PLK1424 siRNA-mediated RNA interference in the PLK-1 mRNA.

Figure 17:
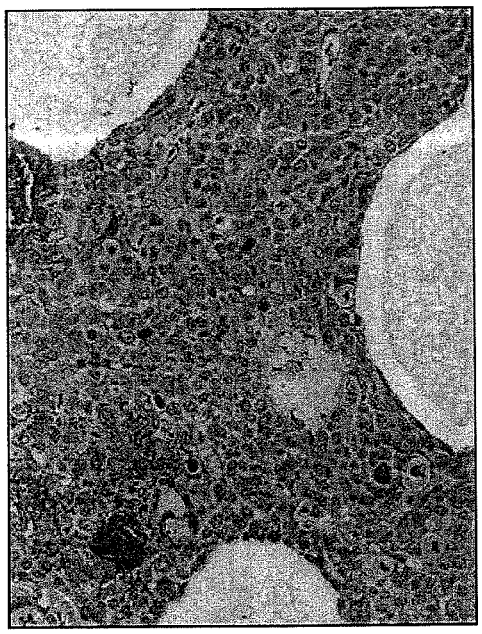
FIG. 17 illustrates data demonstrating that control (Luc) 1:57 SNALP-treated mice displayed normal mitoses in Hep3B tumors (top panels), whereas mice treated with 1:57 SNALP containing PLK-1 siRNA exhibited numerous aberrant mitoses and tumor cell apoptosis in Hep3B tumors (bottom panels).
Figure 17:
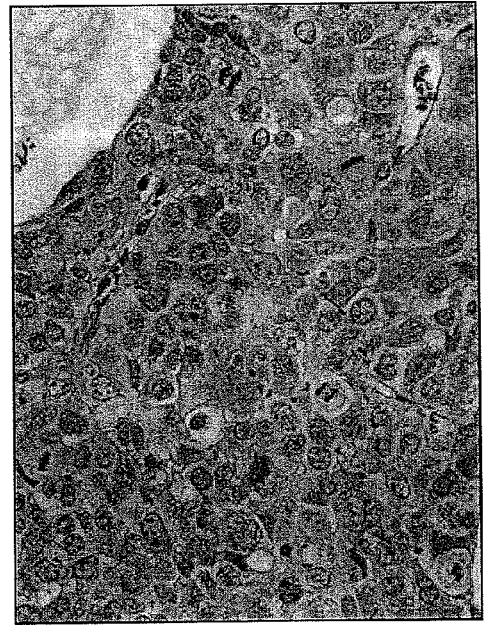
Figure 17:
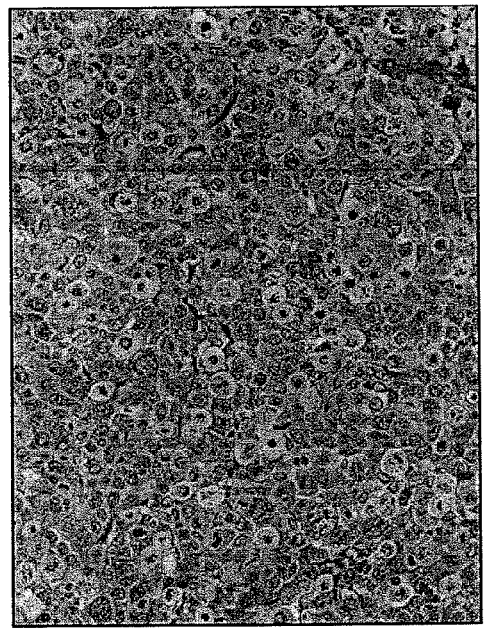
Figure 17:
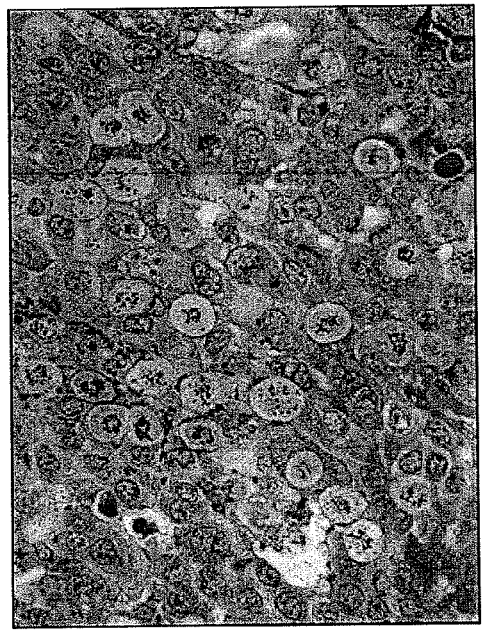

FIG. 17 shows Hep3B tumor histology in mice treated with either Luc SNALP (top) or PLK1424 SNALP (bottom). Luc SNALP-treated mice displayed normal mitoses in Hep3B tumors, whereas PLK1424 SNALP-treated mice exhibited numerous aberrant mitoses and tumor cell apoptosis in Hep3B tumors.

Conclusion

This example illustrates that a single administration of PLK1424 1:57 SNALP to Hep3B tumor-bearing mice induced significant in vivo silencing of PLK-1 mRNA. This reduction in PLK-1 mRNA was confirmed to be mediated by RNA interference using 5' RACE-PCR analysis. Importantly, PLK-1 mRNA silencing by the 1:57 SNALP formulation profoundly disrupted tumor cell proliferation (mitosis), causing subsequent apoptosis of tumor cells. As demonstrated in the previous example, this anti-tumor effect translated into extended survival times in the tumor-bearing mice.

Example 11

Comparison of 1:57 PLK-1 SNALP Containing Either PEG-cDMA or PEG-cDSA in a Subcutaneous Hep3B Tumor Model This example demonstrates the utility of the PEG-lipid PEG-cDSA (3-N-[(-Methoxypoly(ethylene glycol)2000)carbamoyl]-1,2-distearyloxypropylamine) in the 1:57 formulation for systemically targeting distal (e.g., subcutaneous) tumors. In particular, this example compares the tumor targeting ability of 1:57 PLK-1 SNALPs containing either PEG-cDMA ($C_{14}$) or PEG-cDSA ($C_{18}$). Readouts are tumor growth inhibition and PLK1 mRNA silencing. The PLK-1 siRNA used was PLK1424 U4/GU, the sequence of which is provided in Table 8.

Subcutaneous (S.C.) Hep3B tumors were established in scid/beige mice. Multidose anti-tumor efficacy of 1:57 PLK-1 SNALP was evaluated for the following groups (n=5 for each group): (1) "Luc-cDMA"-PEG-cDMA Luc SNALP; (2) "PLK-cDMA"-PEG-cDMA PLK-1 SNALP; and (3) "PLK-cDSA"-PEG-cDSA PLK-1 SNALP. Administration of 6×2 mg/kg siRNA was initiated once tumors reached about 5 mm in diameter (Day 10). Dosing was performed on Days 10, 12, 14, 17, 19, and 21. Tumors were measured by caliper twice weekly.

Figure 18:
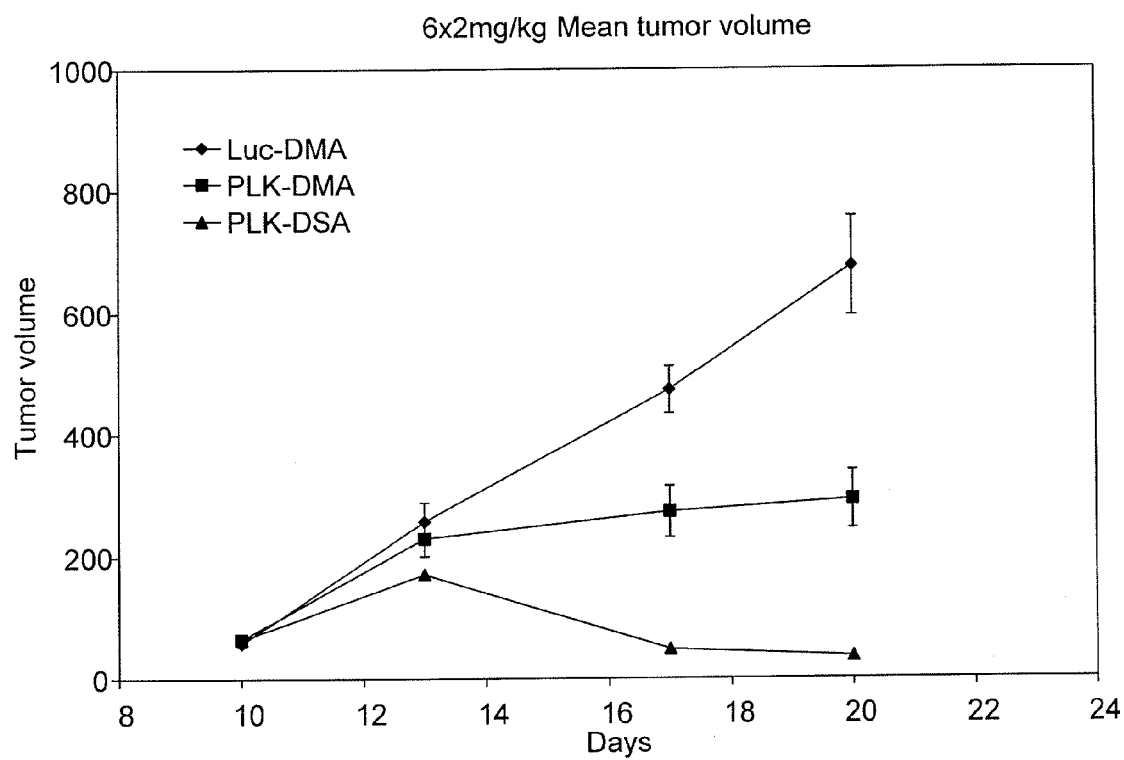
FIG. 18 illustrates data demonstrating that multiple doses of 1:57 PLK-1 SNALP containing PEG-cDSA induced the regression of established Hep3B subcutaneous (S.C.) tumors.

FIG. 18 shows that multiple doses of 1:57 PLK-1 SNALP containing PEG-cDSA induced the regression of established Hep3B S.C. tumors. In particular, 5/5 tumors in the PLK1-cDSA treated mice appeared flat, measurable only by discoloration at the tumor site.

Figure 19:
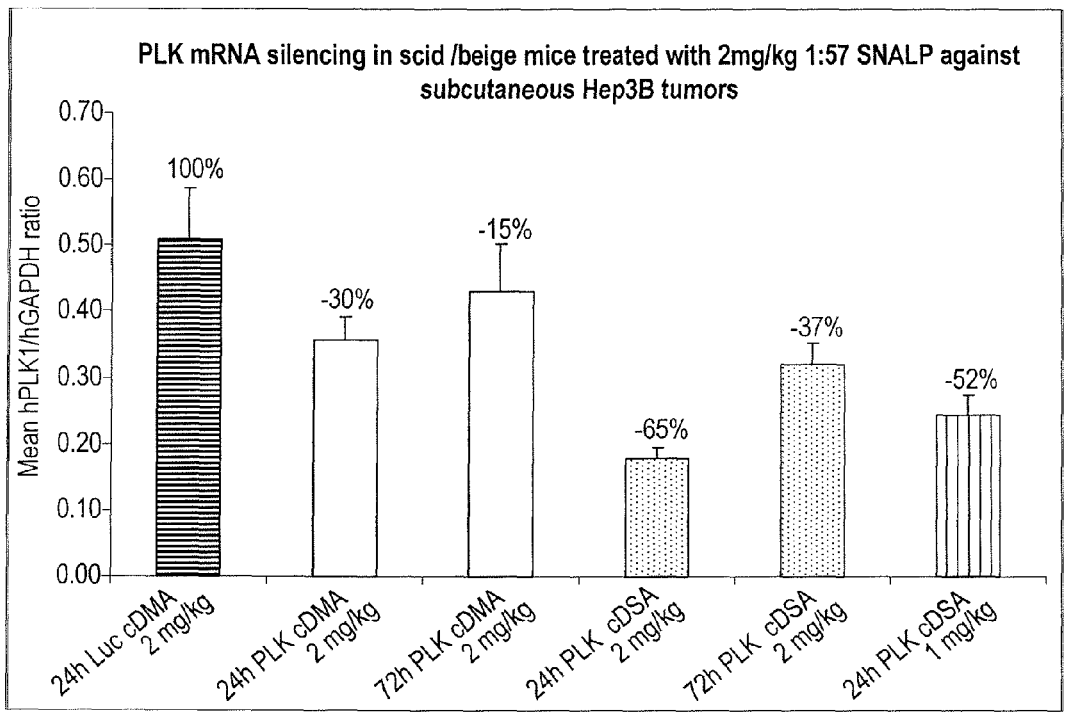
FIG. 19 illustrates data demonstrating PLK-1 mRNA silencing using 1:57 PLK SNALP in S.C. Hep3B tumors following a single intravenous SNALP administration.

FIG. 19 shows the mRNA silencing of 1:57 PLK SNALP in S.C. Hep3B tumors following a single intravenous SNALP administration. The extent of silencing observed with the PLK1-cDSA SNALP correlated with the anti-tumor activity in the multi-dose study shown in FIG. 18.

Figure 20:
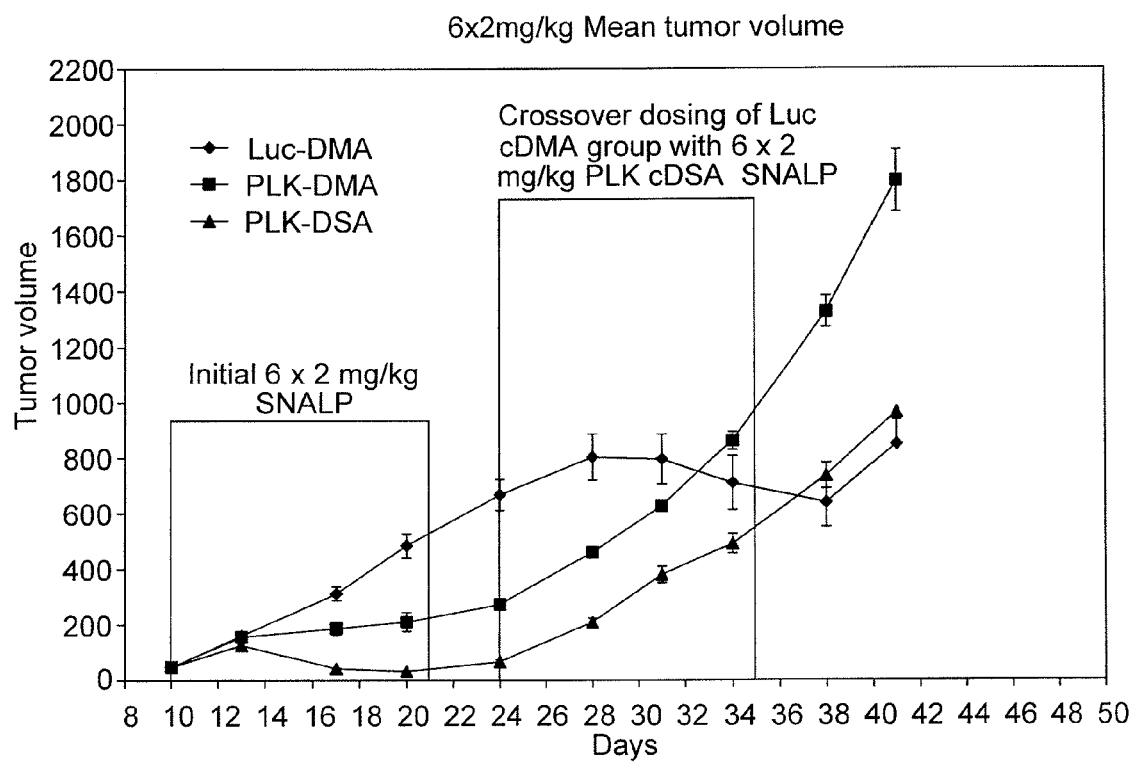
FIG. 20 illustrates data demonstrating that PLK-1 PEG-cDSA SNALP inhibited the growth of large S.C. Hep3B tumors.

The Luc-cDMA SNALP-treated group, which had developed large S.C. tumors at Day 24, were then administered PLK-cDSA SNALP on Days 24, 26, 28, 31, 33, and 35. There was no additional dosing of the original PLK-1 SNALP-treated groups. The results from this crossover dosing study with large established tumors is provided in FIG. 20, which shows that PLK1-cDSA SNALP inhibited the growth of large S.C. Hep3B tumors.

A comparison of the effect of PEG-cDMA and PEG-cDSA 1:57 SNALPs on PLK-1 mRNA silencing was performed using established intrahepatic Hep3B tumors in scid/beige mice. A single 2 mg/kg dose of 1:57 PLK-1 SNALP containing either PEG-cDMA or PEG-cDSA was administered intravenously. Liver/tumor samples were collected at 24 and 96 hours after SNALP treatment. Control=2 mg/kg Luc-cDMA SNALP at 24 hours.

Figure 21:
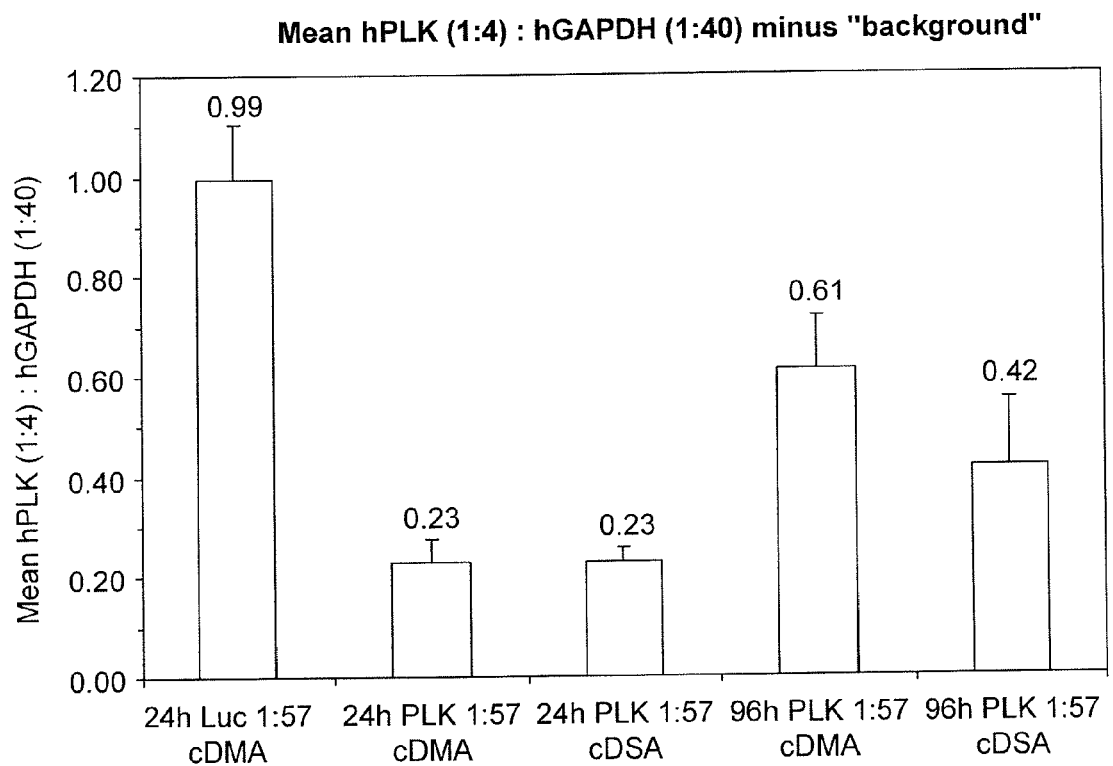
FIG. 21 illustrates data demonstrating tumor-derived PLK-1 mRNA silencing in Hep3B intrahepatic tumors.

FIG. 21 shows that PLK-cDMA SNALP and PLK-cDSA SNALP had similar silencing activities after 24 hours, but that the PLK-cDSA SNALP may increase the duration of mRNA silencing in intrahepatic tumors.

Figure 22:
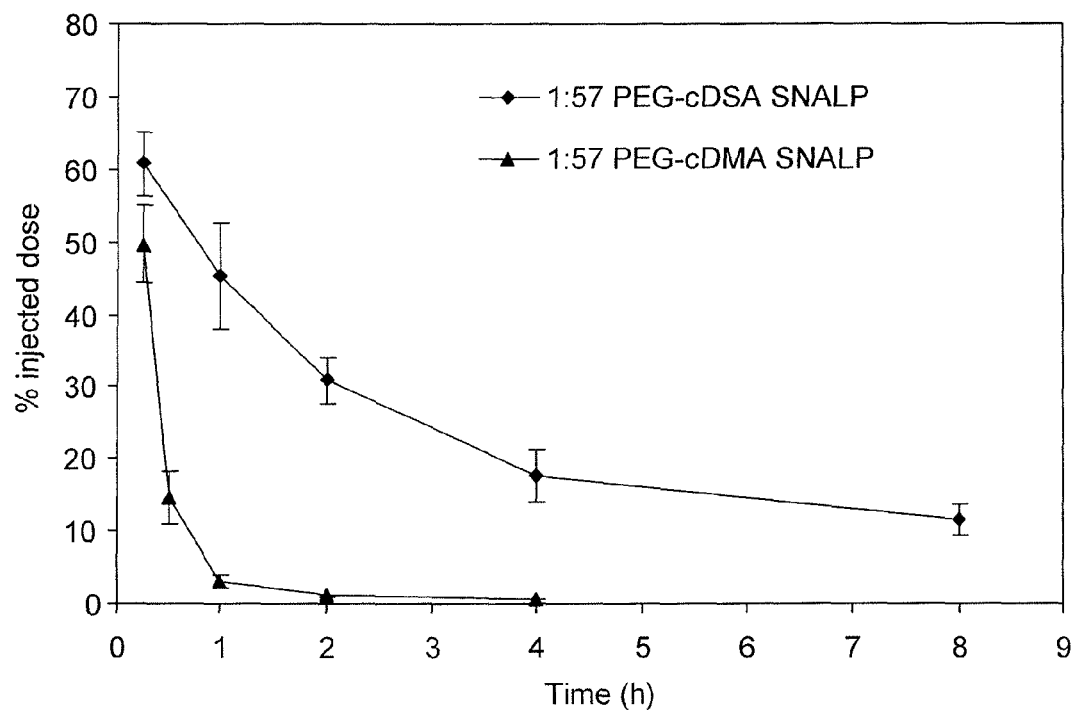
FIG. 22 illustrates data demonstrating the blood clearance profile of 1:57 PLK-1 SNALP containing either PEG-cDMA or PEG-cDSA.

FIG. 22 shows the blood clearance profile of 1:57 PLK-1 SNALP containing either PEG-cDMA or PEG-cDSA. The extended blood circulation times observed for the PLK-cDSA SNALP may enable the increased accumulation and activity at distal (e.g., subcutaneous) tumor sites.

Thus, this study shows that the 1:57 PEG-cDSA SNALP formulation can be used to preferentially target tumors outside of the liver, whereas the 1:57 PEG-cDMA SNALP can be used to preferentially target the liver.

Example 12

Synthesis of Cholesteryl-2'-Hydroxyethyl Ether

Step 1:
A 250 ml round bottom flask containing cholesterol (5.0 g, 12.9 mmol) and a stir bar was sealed and flushed with nitrogen. Toluenesulphonyl chloride (5.0 g, 26.2 mmol) was weighed into a separate 100-mL round bottom flask, also sealed and flushed with nitrogen. Anhydrous pyridine (2×50 ml) was delivered to each flask. The toluenesulphonyl chloride solution was then transferred, via cannula, into the 250 ml flask, and the reaction stirred overnight. The pyridine was removed by rotovap, and methanol (80 ml) added to the residue. This was then stirred for 1 hour until a homogeneous suspension was obtained. The suspension was filtered, washed with acetonitrile (50 ml), and dried under vacuum to yield cholesteryl tosylate as a fluffy white solid (6.0 g, 86%).

Step 2:
Cholesteryl tosylate (2.0 g, 3.7 mmol), 1,4-dioxane (50 mL), and ethylene glycol (4.6 g, 74 mmol) were added to a 100 ml flask containing a stir bar. The flask was fitted with a condenser, and refluxed overnight. The dioxane was then removed by rotovap, and the reaction mixture suspended in water (100 ml). The solution was transferred to a separating funnel and extracted with chloroform (3×100 ml). The organic phases were combined, washed with water (2×150 ml), dried over magnesium sulphate, and the solvent removed. The crude product was purified by column chromatography (5% acetone/hexane) to yield the product as a white solid (1.1 g, 69%).

The structures of the cholesterol derivatives cholesteryl-2'-hydroxyethyl ether and cholesteryl-4'-hydroxybutyl ether are as follows:

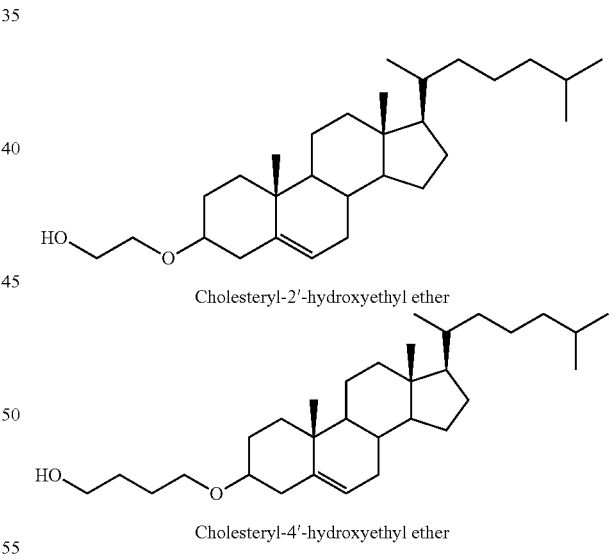

Cholesteryl-2'-hydroxyethyl ether

Cholesteryl-4'-hydroxyethyl ether

It is to be understood that the above description is intended to be illustrative and not restrictive. Many embodiments will be apparent to those of skill in the art upon reading the above description. The scope of the invention should, therefore, be determined not with reference to the above description, but should instead be determined with reference to the appended claims, along with the full scope of equivalents to which such claims are entitled. The disclosures of all articles and references, including patent applications, patents, PCT publications, and Genbank Accession Nos., are incorporated herein by reference for all purposes.

What is claimed is:

1. A nucleic acid-lipid particle comprising:
   (a) a nucleic acid;
   (b) a cationic lipid comprising from 50 mol % to 65 mol % of the total lipid present in the particle;
   (c) a non-cationic lipid comprising a mixture of a phospholipid and cholesterol or a derivative thereof, wherein the phospholipid comprises from 3 mol % to 15 mol % of the total lipid present in the particle and the cholesterol or derivative thereof comprises from 30 mol % to 40 mol % of the total lipid present in the particle; and
   (d) a conjugated lipid that inhibits aggregation of particles comprising from 0.5 mol % to 2 mol % of the total lipid present in the particle.

2. The nucleic acid-lipid particle of claim 1, wherein the nucleic acid comprises a small interfering RNA (siRNA).

3. The nucleic acid-lipid particle of claim 2, wherein the siRNA comprises at least one modified nucleotide.

4. The nucleic acid-lipid particle of claim 2, wherein the siRNA comprises at least one 2'-O-methyl (2'OMe) nucleotide.

5. The nucleic acid-lipid particle of claim 2, wherein the siRNA is about 19 to about 25 base pairs in length.

6. The nucleic acid-lipid particle of claim 2, wherein the siRNA comprises 3' overhangs.

7. The nucleic acid-lipid particle of claim 1, wherein the cationic lipid comprises from 50 mol % to 60 mol % of the total lipid present in the particle.

8. The nucleic acid-lipid particle of claim 1, wherein the phospholipid comprises dipalmitoylphosphatidylcholine (DPPC), distearoylphosphatidylcholine (DSPC), or a mixture thereof.

9. The nucleic acid-lipid particle of claim 1, wherein the phospholipid comprises from 4 mol % to 15 mol % of the total lipid present in the particle.

10. The nucleic acid-lipid particle of claim 1, wherein the phospholipid comprises from 4 mol % to 12 mol % of the total lipid present in the particle.

11. The nucleic acid-lipid particle of claim 1, wherein the phospholipid comprises from 5 mol % to 12 mol % of the total lipid present in the particle.

12. The nucleic acid-lipid particle of claim 1, wherein the phospholipid comprises from 6 mol % to 12 mol % of the total lipid present in the particle.

13. The nucleic acid-lipid particle of claim 1, wherein the cholesterol or derivative thereof comprises from 30 mol % to 35 mol % of the total lipid present in the particle.

14. The nucleic acid-lipid particle of claim 1, wherein the conjugated lipid that inhibits aggregation of particles comprises a polyethyleneglycol (PEG)-lipid conjugate.

15. The nucleic acid-lipid particle of claim 14, wherein the PEG-lipid conjugate comprises a PEG-diacylglycerol (PEG-DAG) conjugate, a PEG-dialkyloxypropyl (PEG-DAA) conjugate, or a mixture thereof.

16. The nucleic acid-lipid particle of claim 15, wherein the PEG-DAA conjugate comprises a PEG-dimyristyloxypropyl (PEG-DMA) conjugate, a PEG-distearyloxypropyl (PEG-DSA) conjugate, or a mixture thereof.

17. The nucleic acid-lipid particle of claim 16, wherein the PEG has an average molecular weight of about 2,000 daltons.

18. The nucleic acid-lipid particle of claim 1, wherein the conjugated lipid that inhibits aggregation of particles comprises from 1 mol % to 2 mol % of the total lipid present in the particle.

19. The nucleic acid-lipid particle of claim 14, wherein the nucleic acid-lipid particle comprises about 55 mol % cationic lipid, about 11 mol % phospholipid, about 33 mol % cholesterol or a derivative thereof, and about 1.6 mol % PEG-lipid conjugate.

20. The nucleic acid-lipid particle of claim 1, wherein the nucleic acid is fully encapsulated in the nucleic acid-lipid particle.

21. A pharmaceutical composition comprising a nucleic acid-lipid particle of claim 1 and a pharmaceutically acceptable carrier.

* * * * *

SEQUENCE LISTING

<160> NUMBER OF SEQ ID NOS: 7

<210> SEQ ID NO 1
<211> LENGTH: 21
<212> TYPE: DNA
<213> ORGANISM: Artificial Sequence
<220> FEATURE:
<223> OTHER INFORMATION: synthetic E5 kinesin-related protein 2263 U/U
      siRNA sense strand of siRNA duplex
<220> FEATURE:
<223> OTHER INFORMATION: Description of Combined DNA/RNA Molecule:
      synthetic E5 kinesin-related protein 2263 U/U siRNA sense strand
      of siRNA duplex
<221> NAME/KEY: modified_base
<222> LOCATION: (2)...(19)
<223> OTHER INFORMATION: n = um
<221> NAME/KEY: modified_base
<222> LOCATION: (20)...(21)
<223> OTHER INFORMATION: n = deoxythimidine (dT)

<400> SEQUENCE: 1
cngaagaccn gaagacaann n                                              21

<210> SEQ ID NO 2
<211> LENGTH: 21
<212> TYPE: DNA
<213> ORGANISM: Artificial Sequence
<220> FEATURE:
<223> OTHER INFORMATION: synthetic E5 kinesin-related protein 2263 U/U
      siRNA antisense strand of siRNA duplex
<220> FEATURE:
<223> OTHER INFORMATION: Description of Combined DNA/RNA Molecule:
      synthetic E5 kinesin-related protein 2263 U/U siRNA antisense
      strand of siRNA duplex
<221> NAME/KEY: modified_base
<222> LOCATION: (8)...(16)
<223> OTHER INFORMATION: n = um
<221> NAME/KEY: modified_base
<222> LOCATION: (20)...(21)
<223> OTHER INFORMATION: n = deoxythimidine (dT)

<400> SEQUENCE: 2
auugucunca ggncuncagn n                                              21

<210> SEQ ID NO 3
<211> LENGTH: 21
<212> TYPE: DNA
<213> ORGANISM: Artificial Sequence
<220> FEATURE:
<223> OTHER INFORMATION: synthetic apolipoprotein B (ApoB) 10048 U2/2
      G1/2 siRNA sense strand of siRNA duplex
<221> NAME/KEY: modified_base
<222> LOCATION: (4)...(4)
<223> OTHER INFORMATION: n = gm
<221> NAME/KEY: modified_base
<222> LOCATION: (8)...(14)
<223> OTHER INFORMATION: n = um

<400> SEQUENCE: 3
agunucanca cacngaauac c                                              21

<210> SEQ ID NO 4
<211> LENGTH: 21
<212> TYPE: DNA
<213> ORGANISM: Artificial Sequence
<220> FEATURE:
<223> OTHER INFORMATION: synthetic apolipoprotein B (ApoB) 10048 U2/2
      G1/2 siRNA antisense strand of siRNA duplex
<221> NAME/KEY: modified_base
<222> LOCATION: (4)...(4)
<223> OTHER INFORMATION: n = um

```
<221> NAME/KEY: modified_base
<222> LOCATION: (7)...(9)
<223> OTHER INFORMATION: n = gm
<221> NAME/KEY: modified_base
<222> LOCATION: (19)...(19)
<223> OTHER INFORMATION: n = um

<400> SEQUENCE: 4
uauncanunu gaugacacnu g                                              21

<210> SEQ ID NO 5
<211> LENGTH: 21
<212> TYPE: DNA
<213> ORGANISM: Artificial Sequence
<220> FEATURE:
<223> OTHER INFORMATION: synthetic polo-like kinase 1 (PLK-1) PLK1424
      U4/GU and PLK1424 U4/G siRNA sense strand of siRNA duplex
<220> FEATURE:
<223> OTHER INFORMATION: Description of Combined DNA/RNA Molecule:
      synthetic polo-like kinase 1 (PLK-1) PLK1424 U4/GU and PLK1424
      U4/G siRNA sense strand of siRNA duplex
<221> NAME/KEY: modified_base
<222> LOCATION: (4)...(18)
<223> OTHER INFORMATION: n = um
<221> NAME/KEY: modified_base
<222> LOCATION: (20)...(21)
<223> OTHER INFORMATION: n = deoxythimidine (dT), u or a ribonucleotide
      complementary to target complementary sequence

<400> SEQUENCE: 5
agancacccn ccunaaanan n                                              21

<210> SEQ ID NO 6
<211> LENGTH: 21
<212> TYPE: DNA
<213> ORGANISM: Artificial Sequence
<220> FEATURE:
<223> OTHER INFORMATION: synthetic polo-like kinase 1 (PLK-1) PLK1424
      U4/GU siRNA antisense strand of siRNA duplex
<220> FEATURE:
<223> OTHER INFORMATION: Description of Combined DNA/RNA Molecule:
      synthetic polo-like kinase 1 (PLK-1) PLK1424 U4/GU siRNA
      antisense strand of siRNA duplex
<221> NAME/KEY: modified_base
<222> LOCATION: (8)...(8)
<223> OTHER INFORMATION: n = gm
<221> NAME/KEY: modified_base
<222> LOCATION: (17)...(17)
<223> OTHER INFORMATION: n = um
<221> NAME/KEY: modified_base
<222> LOCATION: (20)...(21)
<223> OTHER INFORMATION: n = deoxythimidine (dT), u or a ribonucleotide
      complementary to target sequence

<400> SEQUENCE: 6
uauuuaanga gggugancun n                                              21

<210> SEQ ID NO 7
<211> LENGTH: 21
<212> TYPE: DNA
<213> ORGANISM: Artificial Sequence
<220> FEATURE:
<223> OTHER INFORMATION: synthetic polo-like kinase 1 (PLK-1) PLK1424
      U4/G siRNA antisense strand of siRNA duplex
<220> FEATURE:
<223> OTHER INFORMATION: Description of Combined DNA/RNA Molecule:
      synthetic polo-like kinase 1 (PLK-1) PLK1424 U4/G siRNA
      antisense strand of siRNA duplex
<221> NAME/KEY: modified_base
<222> LOCATION: (9)...(15)
```

```
<223> OTHER INFORMATION: n = gm
<221> NAME/KEY: modified_base
<222> LOCATION: (20)...(21)
<223> OTHER INFORMATION: n = deoxythimidine (dT), u or a ribonucleotide
      complementary to target sequence

<400> SEQUENCE: 7
uauuuaagna gngunaucun n                                                  21
```